(12) United States Patent
Iwata et al.

(10) Patent No.: US 6,586,394 B1
(45) Date of Patent: Jul. 1, 2003

(54) TISSUE-DERIVED TUMOR GROWTH INHIBITOR

(75) Inventors: Kenneth K. Iwata, Westbury, NY (US); John R. Stephenson, Santa Cruz, CA (US); Leslie I. Gold, New York, NY (US)

(73) Assignee: OSI Pharmaceuticals, Inc., Uniondale, NY (US)

( * ) Notice: Subject to any disclaimer, the term of this patent is extended or adjusted under 35 U.S.C. 154(b) by 0 days.

(21) Appl. No.: 08/188,197

(22) Filed: Jan. 27, 1994

Related U.S. Application Data

(63) Continuation-in-part of application No. 08/147,904, filed on Nov. 4, 1993, now abandoned, which is a continuation of application No. 07/768,100, filed on Sep. 30, 1991, now abandoned, which is a continuation of application No. 07/111,022, filed on Oct. 20, 1987, now abandoned, which is a continuation-in-part of application No. 06/922,121, filed on Oct. 20, 1986, now abandoned, which is a continuation-in-part of application No. 06/847,931, filed on Apr. 7, 1986, now abandoned, which is a continuation-in-part of application No. 06/725,003, filed on Apr. 19, 1985, now abandoned.

(51) Int. Cl.[7] .................... A61K 38/18; C07K 14/475
(52) U.S. Cl. .................. 514/12; 530/350; 530/351; 530/399; 530/412; 530/413; 530/416; 530/417
(58) Field of Search ............... 435/69.4, 69.9, 435/172.1, 240.2, 325; 530/350, 351, 412, 413, 416, 417, 399; 424/94.1; 514/12

(56) References Cited

U.S. PATENT DOCUMENTS

| | | | |
|---|---|---|---|
| 4,434,094 A | 2/1984 | Seyedin et al. | 530/416 |
| 4,708,948 A | 11/1987 | Iwata et al. | 514/2 |
| 4,774,228 A | 9/1988 | Seyedin et al. | 514/21 |
| 4,774,322 A | 9/1988 | Seyedin et al. | 530/353 |
| 4,886,747 A | * 12/1989 | Derynck et al. | 435/69.4 |
| 5,104,977 A | 4/1992 | Sporn et al. | 530/399 |

FOREIGN PATENT DOCUMENTS

| | | |
|---|---|---|
| EP | 136093 | 4/1985 |
| EP | 159289 | 10/1985 |
| EP | 271211 | 6/1986 |
| JP | 86298432 | 12/1986 |
| WO | 8404924 | 12/1984 |

OTHER PUBLICATIONS

Derynck et al. (Nature) vol. 316: pp 701–705, Aug. 22, 1985.*
Stewart et al. (1996) Umbilical Cord Transforming Growth Factor–β3: Isolation, Comparison with Recombinant TGF–β3 and Cellular Localization, Growth Factors 13;87–98.
Bhown, A.S. and Bennett, J.C. (1983) High–sensitivity Sequence Analysis of Proteins Recovered from Sodium Dodecyl Sulfate Gels, Methods in Enzymology 91:450–455.
A.B. Roberts, et al. (1985) Proc. Natl. Acad. Sci.; 82: 119.
Frolik C. et al., (1983) PNAS, 80: 3676–3680.
Roberts A. et al., (1980) PNAS, 77: 3494–3498.
Iwata K., (1983) Fed. Proc. Am. Soc. Exp. Biol., 42: 1833 Abst. 442.
Davoren P., (1983) Biochemical Biophysical Acta, 63: 150–153.

* cited by examiner

*Primary Examiner*—Marianne P. Allen
(74) *Attorney, Agent, or Firm*—John P. White; Cooper & Dunham LLP

(57) ABSTRACT

This invention is directed to a chromatographically recovered polypeptide having the N-terminal amino acid sequence Ala-Leu-Asp-Thr-Asn-Tyr-Cys-Phe-Arg-Asn-Leu-Clu-Asn-Cys-Cys-Val. This polypeptide is known as TGI, TGI-1 and TGI-2. It is also referred to as TGF-β3. The invention is also directed to a compositions which comprises the chromatographically recovered polypeptide. The invention also provides a pharmaceutical compositions to inhibit the growth of epithelial cells or heal a wound or treat a burn consisting of the chromatographically recovered polypeptide. The invention is also directed to methods which comprise administering to a subject an effective amount of the chromatographically recovered so as to thereby inhibit the growth of epithelial cells, or heal the wound or treat the burn.

1 Claim, 38 Drawing Sheets

FIGURE 15

N-TERMINAL SEQUENCES OF TGI AND TGFβs

TGFβ1: Ala Leu Asp Thr Asn Tyr Cys Phe Ser Ser Thr Glu Lys Asn Cys Cys Val Arg Gln Leu Tyr

TGFβ2: Ala Leu Asp Ala Ala Tyr Cys Phe Arg Asn Val Gln Asp Asn Cys Cys Leu Arg Pro Leu Tyr

TGFβ3: Ala Leu Asp Thr Asn Tyr Cys Phe Arg Asn Leu Glu Glu Asn Cys Cys Val Arg Pro Leu Tyr

TGI: Ala Leu Asp Thr Asn Tyr Cys Phe Arg Asn Leu Glu Glu Asn Cys Cys Val Xxx Pro Leu Tyr

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:

```
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Ala Leu Asp Thr Asn Tyr Cys Phe Ser Ser Thr Glu Lys Asn Cys Cys
1               5                  10                  15

Val Arg Gln Leu Thr
            20

(2) INFORMATION FOR SEQ ID NO:2:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Ala Leu Asp Ala Ala Tyr Cys Phe Arg Asn Val Gln Asp Asn Cys Cys
1               5                  10                  15

Leu Arg Pro Leu Tyr
            20

(2) INFORMATION FOR SEQ ID NO:3:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Ala Leu Asp Thr Asn Tyr Cys Phe Arg Asn Leu Glu Glu Asn Cys Cys
1               5                  10                  15

Val Arg Pro Leu Tyr
            20

(2) INFORMATION FOR SEQ ID NO:4:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Ala Leu Asp Thr Asn Tyr Cys Phe Arg Asn Leu Glu Glu Asn Cys Cys
1               5                  10                  15

Val Xaa Pro Leu Tyr
            20

(2) INFORMATION FOR SEQ ID NO:5:

(i) SEQUENCE CHARACTERISTICS:
            (A) LENGTH: 17 amino acids
            (B) TYPE: amino acid
            (C) STRANDEDNESS: single
```

-continued

```
    (D) TOPOLOGY: linear (ii) MOLECULE TYPE: peptide (xi) SEQUENCE DESCRIPTION: SEQ ID NO:5:

Ala Leu Asp Thr Asn Tyr Cys Phe Arg Asn Leu Glu Glu Asn Cys Cys
1               5                   10                  15
Val
```

TISSUE-DERIVED TUMOR GROWTH INHIBITOR

This application is a continuation-in-part of U.S. Ser. No. 08/147,904, filed Nov. 4, 1993 now abandoned, which is a continuation of U.S. Ser. No. 07/768,100, filed Sep. 30, 1991, now abandoned, which was a continuation of U.S. Ser. No. 07/111,022, filed Oct. 20, 1987, now abandoned, which was a continuation-in-part of U.S. Ser. No. 06/922,121, filed Oct. 20, 1986, now abandoned, which was a continuation-in-part of U.S. Ser. No. 06/847,931, filed Apr. 7, 1986, now abandoned, which was a continuation-in-part of U.S. Ser. No. 06/725,003, filed Apr. 19, 1985, now abandoned.

BACKGROUND OF THE INVENTION

Bichel [Bichel, Nature 231: 449–450 (1971)] reported that removing most of the tumor from mice bearing ascites tumors at a plateau of tumor growth was followed by a marked increase in the growth of the remaining tumor cells. Injection of cell-free ascites, obtained from mice bearing fully developed ascites tumors, into mice with growing ascites tumors resulted in a pronounced inhibition of ascites growth. Bichel, supra, also observed that two surgically joined mice (parabiotic), one mouse with an advanced tumor and the other with an early tumor, resulted in a pronounced inhibition of growth of the early tumor. Based upon these observations, [Bichel, Europ. J. Cancer 6: 291–296 (1970) and Bichel, supra] the existence of a diffusible inhibitory principle which circulated through the peritoneum of the parabiotic mice and was present in the cell-free ascites fluid produced by the fully developed ascites tumors was postulated. The nature of this inhibiting principle was not characterized, but it was speculated that the rate of growth of the ascites tumors was dependent upon the amount of tumor tissue and was determined by the amount of inhibitory principle produced.

Substances having tumor growth inhibitory activity have been described. [Holley, et al., Proc. Natl. Acad. Sci. USA 77:5989 (1980) and Holley, et al., Cell Biol. Int. Reports 7: 525–526 (1983)]. These publications report the isolation from African green monkey BSC-1 cells of a growth inhibitory substance which inhibited the growth of BSC-1 cells, human mammary tumor cells and normal human mammary cells. This substance has recently [Tucker, et al., Science 226: 705–707 (1984): Roberts, et al. Proc. Natl. Acad. Sci. 82 (Jan): 119–123 (1985)] been shown to be identical, or highly related, to a 25,000 dalton two chain human platelet-derived polypeptide designated β-TGF (Assoian, et al., J. Biol. Chem. 258: 7155–7160 (1983)]. Independently, McMahon, et al. [Proc. Natl. Acad. Sci. USA 79, 456–460 (1982)] have purified from rat liver a 26,000 dalton substance which inhibits the proliferation of nonmalignant rat liver cells, but does not inhibit the proliferation of malignant rat liver cells. Other growth inhibitory substances have been identified in cultured chick spinal cord cells [Kagen, et al., Experimental Neurology 58: 347–360 (1970); Harrington, et al., Proc. Natl. Acad. Sci. USA 77: 423–427 (1980) and Steck, et al. J. Cell Biol. 83: 562–575 (1979)].

Iwata, et al., [J. Cellular Biochem. Supp. 5: 401 (1982)] previously described a microtiter plate system for assaying growth stimulation and growth inhibition activity. Todaro, et al. [Todaro, et al., in *Tumor Cell Heterogeneity; Origins and Implications,* Bristol-Myers Cancer Symposia, Volume 4, Owens, A. H., Coffey, D. S., and Baylin, S. B., Eds. (Academic Press, 1982), pp. 205–224)] and Iwata, et al. [Fed. Proc. Fed. AM. Soc. Exp. Biol. 42: 1833 (1983)] previously reported the isolation of tumor inhibitory activity from tissue culture fluids of human tumor cells propagated in culture. The observations described in these reports were preliminary and little detail was provided.

On Apr. 20, 1984, a patent application was filed with the United States Patent and Trademark Office under U.S. Ser. No. 602,520, entitled "Substantially Purified Tumor Growth Inhibitory Factor (TIF)" on which one of us, Kenneth K. Iwata, is named as coinventor. This application concerns the preliminary identification of a not well-defined substance or substances present in, and derived from, human tumor cells propagated in culture. This substance or substances resembles the tumor inhibitory activity previously reported. [Todaro, et al., in *Tumor Cell Heterogeneity; Origins and Implications,* Bristol-Myers Cancer Symposia, Volume 4, Owens A. H., Coffey, D. S., and Baylin, S. B., Eds. (Academic Press, 1982), pp. 205–224); Iwata, et al., Fed. Proc. Fed. Am. Soc. Exp. Biol. 42: 1833 (1983].

Todaro [Todaro, G. J. in *Epigenetic Regulation of Cancer,* Terry Fox Cancer Research Conference (University of British Columbia; Vancouver, B.C., Canada) Abs. 13 (1984)] recently reported two factors with tumor cell growth inhibitory properties which were reportedly sequenced and shown to consist of 70 and 90 amino acid residues, respectively. Neither the source, i.e. cell, tissue type of species, or the method of purification of the factors were disclosed.

SUMMARY OF THE INVENTION

This invention is directed to a chromatographically recovered polypeptide having the N-terminal amino acid sequence Ala-Leu-Asp-Thr-Asn-Tyr-Cys-Phe-Arg-Asn-Leu-Glu-Glu-Asn-Cys-Cys-Val. This polypeptide is known as TGI, TGI-1 and TGI-2. It is also referred to as TGF-β3. The invention is also directed to a compositions which comprises the chromatographically recovered polypeptide. The invention also provides a pharmaceutical compositions to inhibit the growth of epithelial cells or heal a wound or treat a burn consisting of the chromatographically recovered polypeptide. The invention is also directed to methods which comprise administering to a subject an effective amount of the chromatographically recovered so as to thereby inhibit the growth of epithelial cells, or heal the wound or treat the burn.

Elution pattern of gel filtration chromatography at 23° C. of crude acidified, ethanol extract from human umbilical cords. Two grams of acidified, ethanol extract in 150 ml of 1.0 M acetic acid was applied to a 14×100 cm column (Amicon; #86012) containing Bio-Gel P-10 and eluted at a flow rate of 7 ml/min. One liter fractions were collected on a SuperRac (LKB 2211) equipped with a type C collection rack (LKB). One ml aliquots of each fraction (1 liter/fraction) were transferred to 12×75 mm sterile snap top tubes (Falcon 2058). TGI activity was determined as described in Materials and Methods. Inhibition of A549 human lung carcinoma cells is shown by open triangles and mink lung (CCL64) cells by open circles. Absorbance at 280 nm (———) was detected by a Uvicord S (LKB 2138) with a full scale absorbance range of 1.0 AUFS and a single chart recorder (LKB 2210) with a chart speed of 1 mm/min.

Figure 2:
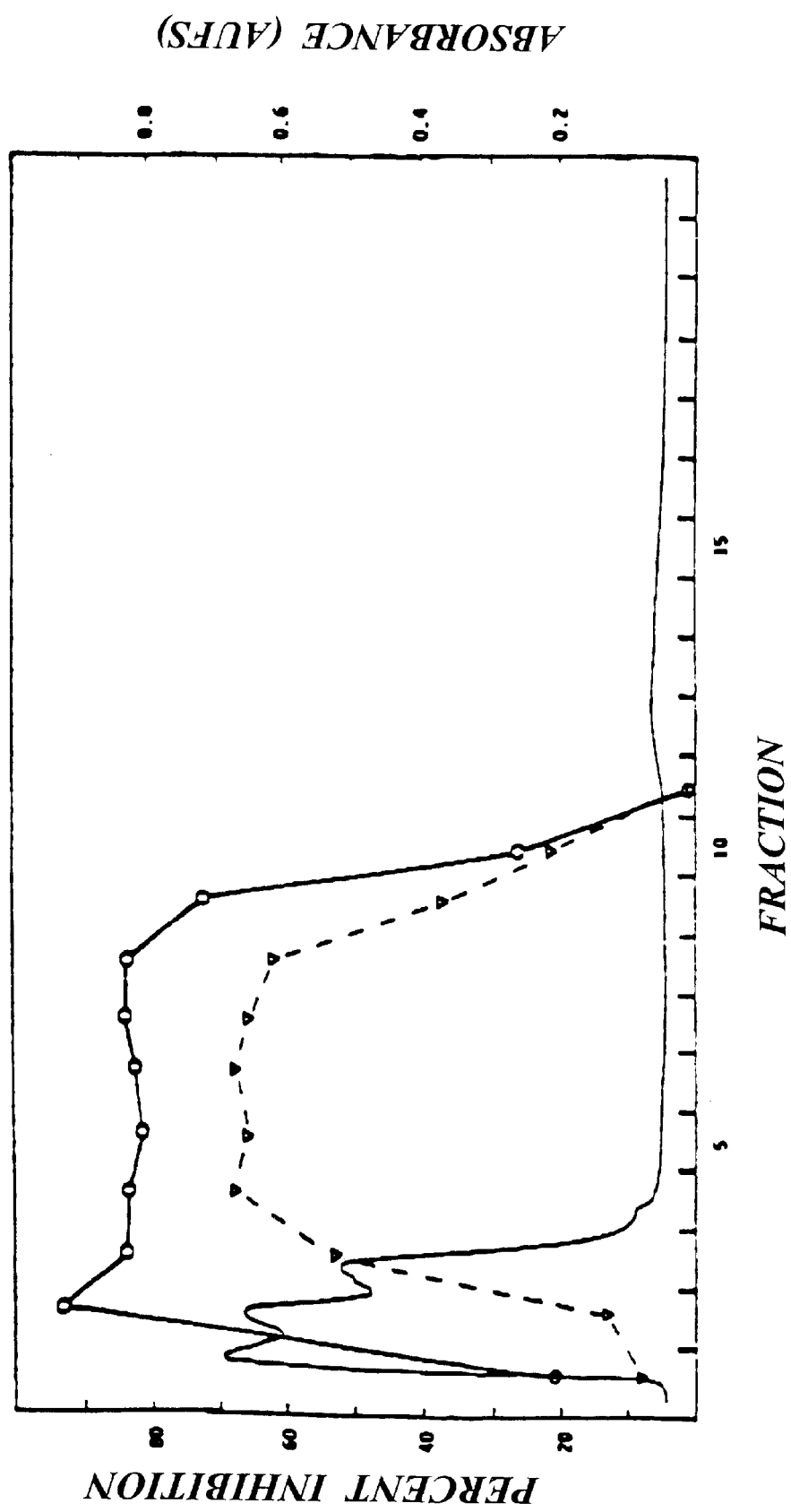

FIG. 2. Gel filtration chromatography at 4° C.

Elution of gel filtration chromatography at 4° C. of crude acidified, ethanol extract from human umbilical cords. Two grams of acidified, ethanol extract in 150 ml of 1.0 M acetic acid were applied to a 14×100 cm column (Amicon; #86012) containing Bio-Gel P-10 and eluted at a flow rate of 7 ml/min. One liter fractions were collected on a SuperRac (LKB 2211) equipped with a type C collection rack (LKB). One ml aliquots of each fraction (1 liter/fraction) were transferred to 12×75 mm sterile snap top tubes (Falcon 1058). TGI activity was determined as described in Materials and Methods. Inhibition of A549 human lung carcinoma cells is shown by open triangles and mink lung (CCL64) cells by open circles. Absorbance at 280 nm (_____) was detected by a Uvicord S (LKB 2138) with a full scale absorbance range of 1.0 AUFS and a single chart recorder (LKB 2210) with a chart speed of 1 mm/min.

Figure 3:
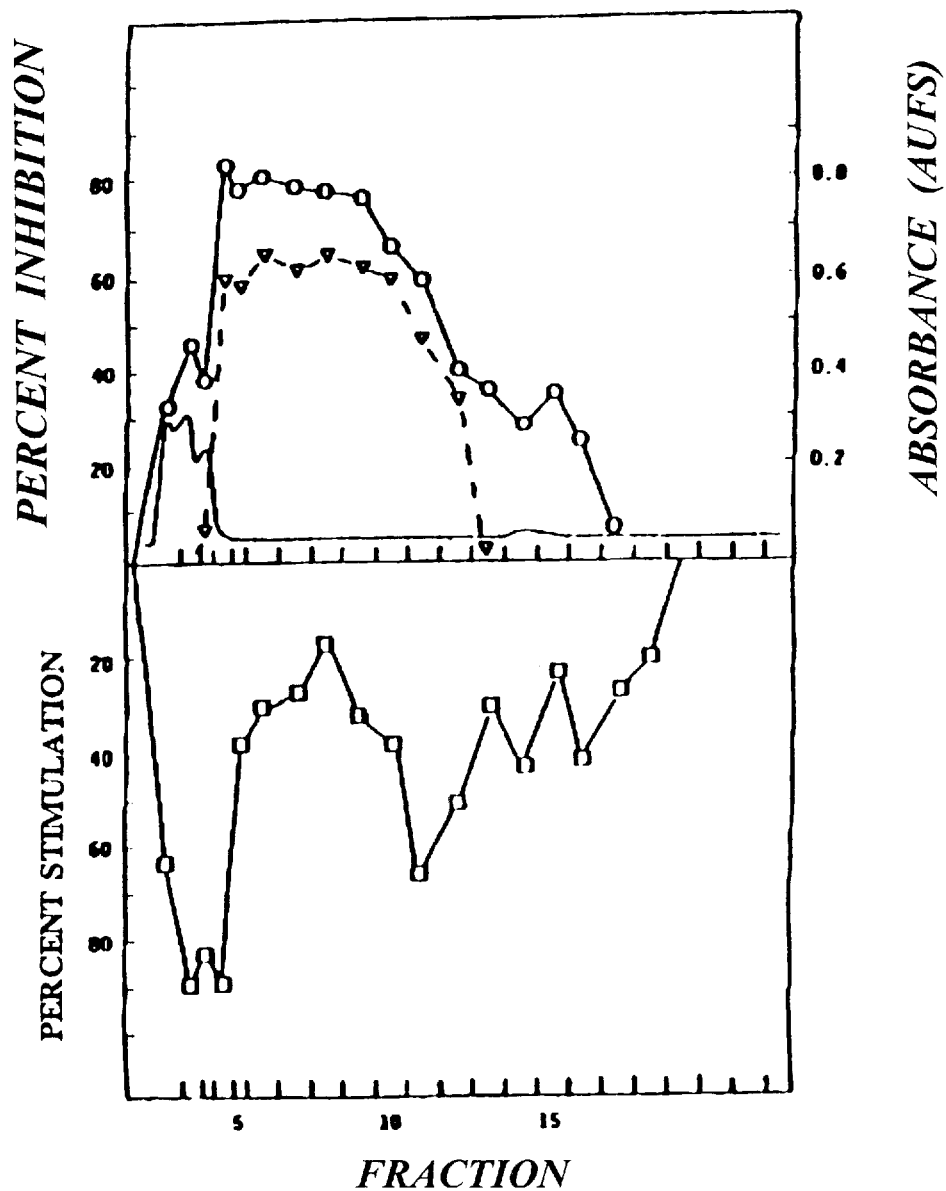

FIG. 3. Cell growth inhibition and normal human cell stimulation by fractions from gel filtration chromatography at 4° C.

Elution pattern of gel filtration chromatography at 4° C. of crude acidified, ethanol extract in 150 ml of 1.0 M acetic acid was applied to a 14×100 cm column (Amicon; #86012) containing Bio-Gel P-10 and eluted at a flow rate of 7 ml/min. One liter fractions were collected on a SuperRac (LKB 2211) equipped with a type C collection rack (LKB). One ml aliquots of each fraction (1 liter/fraction) were transferred to 12×75 mm sterile snap top tubes (Falcon 2058). TGI activity was determined as described in Materials and Methods. Inhibition of A549 human lung carcinoma cells is shown by open triangles and mink lung (CCL64) cells by open circles. Stimulation of normal human fibroblasts is shown by open squares. Absorbance at 280 nm (_____) was detected by a Uvicord S (LKB 2138) with a full scale absorbance range of 1.0 AUFS and a single chart recorder (LKB 2210) with a chart speed of 1 mm/min.

Figure 4:
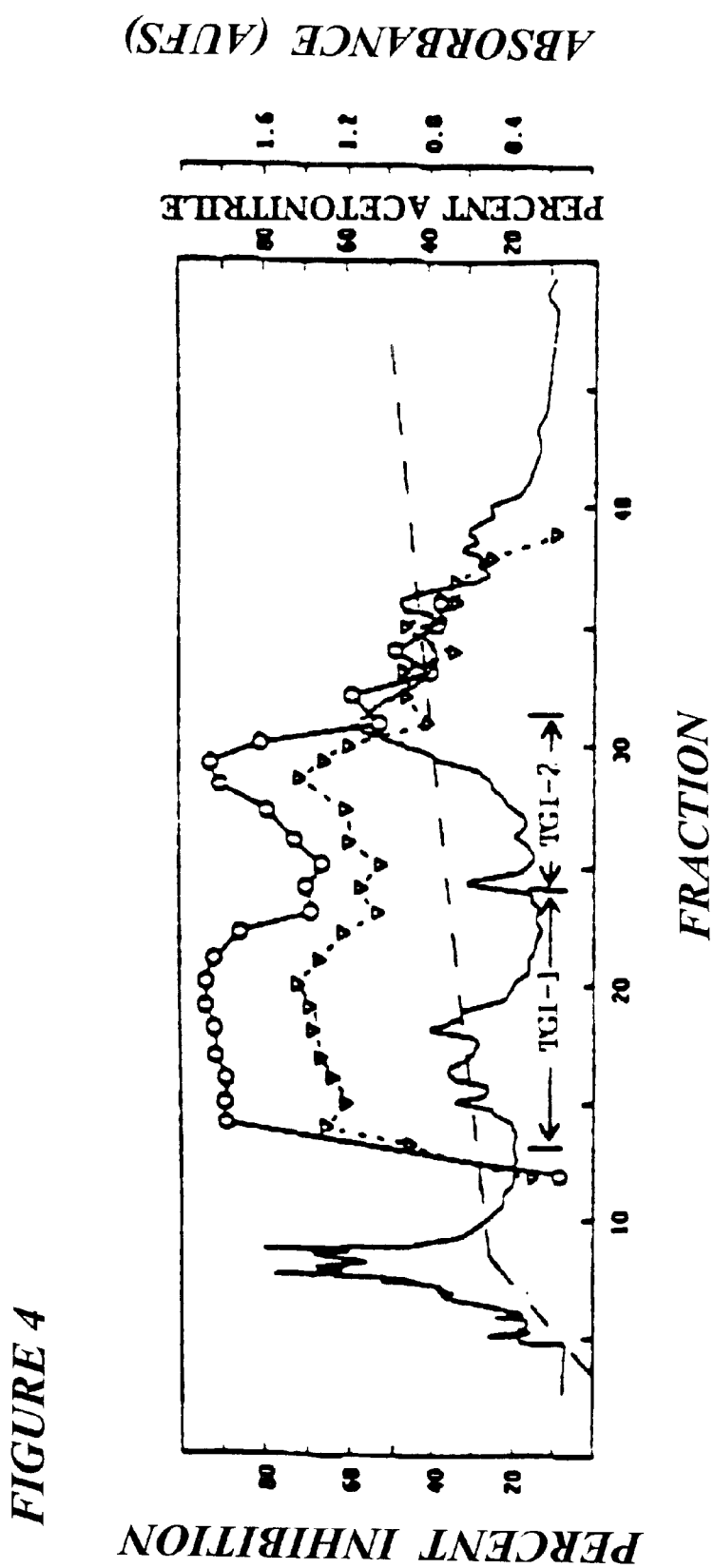

FIG. 4. Reverse phase high performance liquid chromatography (HPLC) of an active fraction from gel filtration chromatography Fraction 4 derived from gel filtration chromatography on Bio-Gel P-10 of human umbilical cord acidified, ethanol extract (65.8 mg protein) was lyophilized and resuspended in 10 ml of 0.05% trifluoroacetic acid (TFA). Fraction 4 was the first fraction following the major peaks of absorbance at 280 nm. (FIG. 2) The sample was centrifuged on a Beckman table top centrifuge (Beckman TJ-6) at 3000 rpm for 20 minutes to remove insoluble material. Three separate injections of the supernatant were made through a Water's U6K injector equipped with a 2 ml sample loop. The sample was then loaded onto a uBONDAPAK $C_{18}$ column (0.78×30 cm) (Waters # 84176). The flow rate was 2 ml/min and the effluent monitored at 206 nm (_____) with a Waters u.v. detector (Waters Model 481) at a sensitivity of 2.0 AUFS. Elution was achieved with a linear 30-min. gradient from 0.25% of increasing concentrations of acetonitrile containing 0.05% TFA, followed by a linear 240-min gradient of 25–45% acetonitrile containing 0.05% TFA, followed by a linear 30-min gradient of 45–100% acetonitrile containing 0.05% TFA. A SuperRac (LKB 2211) was used to collect 12 ml fractions. One ml aliquots of each fraction were transferred to 12×75 mm polystyrene tubes (Falcon 2058) containing 50 µl of 1.0 M acetic acid and 50 µg of bovine serum albumin (Sigma B) and assayed for TGI activity as described in Materials and Methods. Inhibition of A549 human lung carcinoma cells is shown by open triangles and of mink lung (CCL64) by open circles. The solvent gradient is shown by large dashes (— — —).

Figure 5:
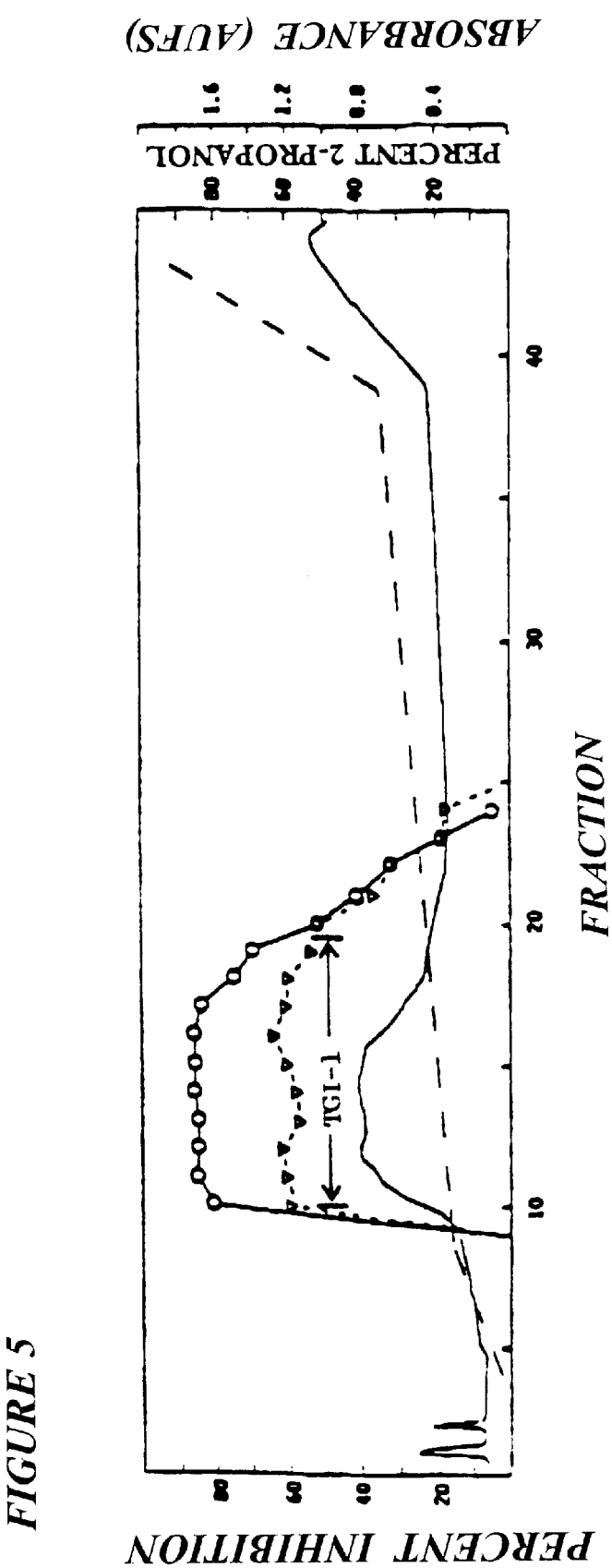

FIG. 5. HPLC rechromatography of pooled TGI activity from HPLC (TGI-1)

Pooled fractions of TGI activity (1.5 mg) eluting between 28–34% acetonitrile (fractions 13–22) by HPLC chromatography (FIG. 4) was lyophilized and resuspended in 2 ml of 0.05% TFA. The sample was centrifuged on a Beckman table top centrifuge (Beckman TJ-6) at 3000 rpm for 20 minutes to remove insoluble material. Two separate injections of the supernatant were made through a Water's U6K injector equipped with a 2 ml sample loop. The sample was loaded onto a uBondapak $C_{18}$ column (0.39×30 cm) (Waters #27324). The flow rate was 1 ml/min and the effluent monitored at 206 nm (_____) with a Waters u.v. detector (Waters Model 481) at a sensitivity of 2.0 AUFS. Elution was achieved with a linear 20-min. gradient from 0–15% of increasing concentrations of 2-propanol containing 0.05% TFA, followed by a linear 120-min gradient of 15–35% 2-propanol containing 0.05% TFA. A SuperRac (LKB 2211) was used to collect 4 ml fractions. One ml aliquots of each fraction were transferred to 12×75 mm polystyrene tubes (Falcon 2058) containing 50 µl of 1.0 M acetic acid and 50 µg of bovine serum albumin (Sigma A-6003) and assayed for TGI activity as described in Materials and Methods. Inhibition of A549 human lung carcinoma cells is shown by open triangles and of mink lung (CCL64) by open circles. The solvent gradient is shown by large dashes (— — —).

Figure 6:
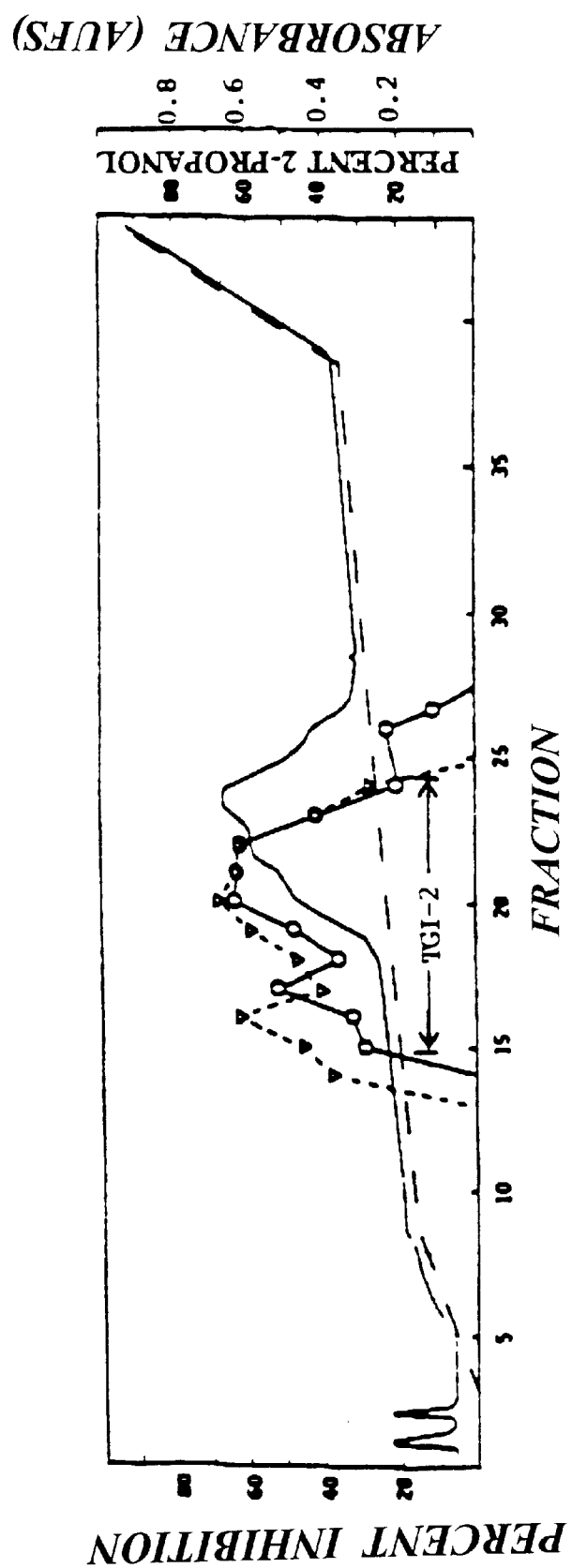

FIG. 6. Reverse phase HPLC rechromatography of pooled activity from HPLC (TGI-2)

Pooled fractions of TGI activity (0.8 mg) eluting between 35–39% acetonitrile (fractions 25–31) by HPLC chromatography (FIG. 4) was lyophilized and resuspended in 2 ml of 0.05% TFA. The sample was centrifuged on a Beckman table top centrifuge (Beckman TJ-6) at 3000 rpm for 30 minutes to remove insoluble material. Two separate injections of the supernatant were made through a Water's U6K injector equipped with a 2 ml sample loop. The sample was loaded onto a uBondapak $C_{18}$ column (0.39×30 cm) (Waters #27324). The flow rate was 1 ml/min and the effluent monitored at 206 nm (_____) with a Waters u.v. detector (Waters Model 481) at a sensitivity of 1.0 AUFS. Elution was achieved with a linear 20-min gradient from 0.15% of increasing concentrations of 2-propanol containing 0.05% TFA, followed by a linear 120-min gradient of 15–35% 2-propanol containing 0.05% TFA. A SuperRac (LKB 2211) was used to collect 4 ml fractions. One ml aliquots of each fraction were transferred to 12×75 mm polystyrene tubes (Falcon 2058) containing 50 µl of 1.0 M acetic acid and 50 µg of bovine serum albumin (Sigma A-6003) and assayed for TGI activity as described in Materials and Methods. Inhibition of A549 human lung carcinoma cells is shown by open triangles and of mink lung (CCL64) by open circles. The solvent gradient is shown by large dashes (— — —).

Figure 7:
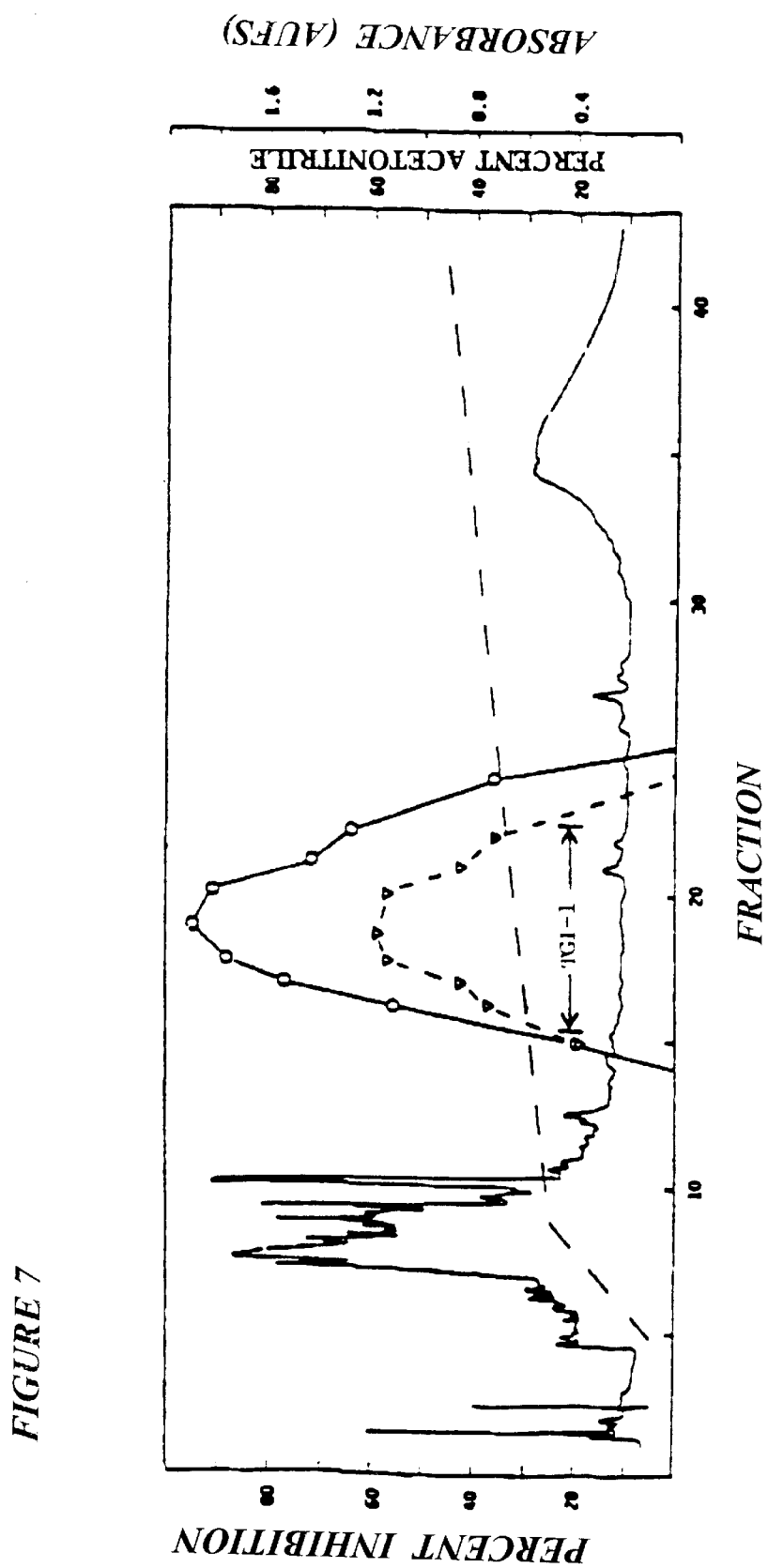

FIG. 7. Reverse phase HPLC of an active fraction from gel filtration chromatography Fraction 5 derived from gel filtration chromatography on Bio-Gel P-10 of human umbilical cord acidified, ethanol extract was lyophilized and resuspended in 4 ml of 0.05% trifluoroacetic acid (TFA). Fraction #5 was the second fraction following the major peaks of absorbance at 280 nm. (FIG. 2) The sample was centrifuged on a Beckman table top centrifuge (Beckman TJ-6) at 3000 rpm for 20 minutes to remove insoluble material. Two separate injections of the supernatant were made through a Water's U6K injector equipped with a 2 ml sample loop. The sample (1.3 ml total) was then loaded onto a uBondapak $C_{18}$ column (0.78×30 cm) (Water # 84176). The flow rate was 2 ml/min and the effluent monitored at 206 nm (_____) with a Waters u.v. detector (Waters Model 481) at a sensitivity of 2.0 AUFS. Elution was achieved with a linear 30-min. gradient from 0.25% of increasing concentrations of acetonitrile containing 0.05% TFA, followed by a linear 240-min gradient of 25–45% acetonitrile containing 0.05% TFA, followed by a linear 30-min gradient of 45–100% acetonitrile containing 0.05% TFA. A SuperRac (LKB 2211) was used to collect 12 ml fractions. One ml aliquots of each fraction were transferred to 12×87 mm polystyrene tubes (Falcon 2058) containing 50 µl of 1.0 M acetic acid and 50 µg of bovine serum albumin (Sigma A6003) and assayed for TGI activity as described in Materials and Methods. Inhibition of A549 human lung carcinoma cells is shown by open triangles and of mink lung (CCL64) by open circles. The solvent gradient is shown by large dashes (— — —).

Figure 8:
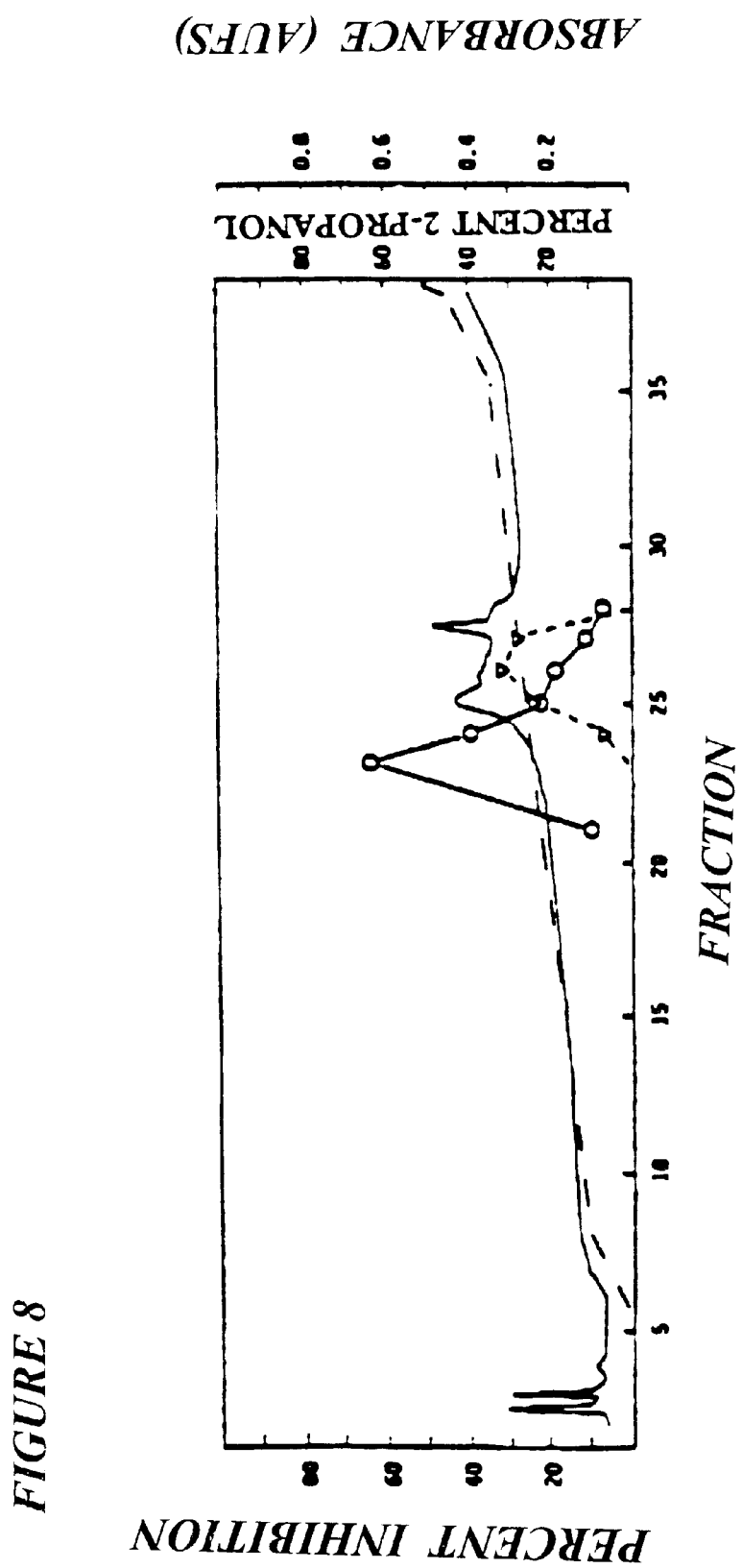

FIG. 8. Reverse phase HPLC rechromatography of pooled TGI activity from HPLC (TGI-1)

Pooled fractions of TGI activity (1.1 mg) eluting between 29–34% acetonitrile (FIG. 7; fractions 14–25) were lyophilized and resuspended in 2 ml of 0.05% TFA. The samples were centrifuged on a Beckman table top centrifuge (Beckman TJ-6) at 3000 rpm for 20 minutes to remove insoluble material. Two separate injections of the supernatant (1.6 ml) were made through a Water's U6K injector equipped with a 2 ml sample loop. The sample was loaded onto a uBondapak $C_{18}$ column (0.78×30 cm) (Waters #84174). The flow rate was 1 ml/min and the effluent monitored at 206 nm (———) with a Waters u.v. detector (Waters Model 481) at a sensitivity of 1.0 AUFS. Elution was achieved with a linear gradient for 20-min. from 0–10% of increasing concentrations of 2-propanol containing 0.05% TFA, followed by a linear 220-min gradient of 10–35% 2-propanol containing 0.05% TFA, followed by a linear 20-min gradient of 35–45% 2-propanol containing 0.05% TFA, followed by a linear 20-min gradient of 45–100% 2-propanol containing 0.05% TFA. A SuperRac (LKB 2211) was used to collect 8 ml fractions. One ml aliquots of each fraction were transferred to 12×75 mm polystyrene tubes (Falcon 2058) containing 50 µl of 1.0 M acetic acid and 50 µg of bovine serum albumin (Sigma 6003) and assayed for TGI activity as previously described. Inhibition of A549 human lung carcinoma cells is shown by open triangles and of mink lung (CCL64) by open circles. The solvent gradient is shown by large dashes (— — —).

Figure 9:
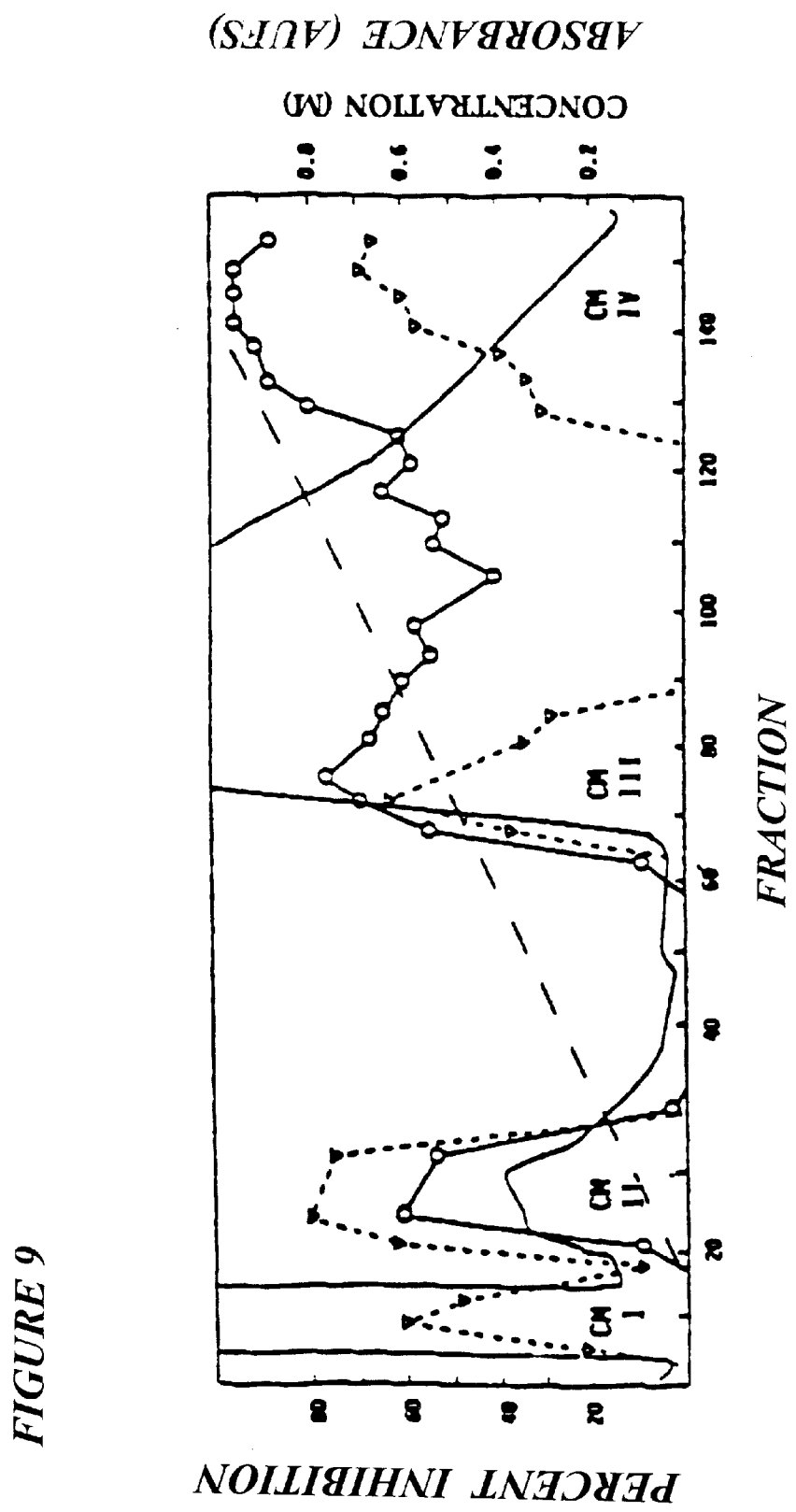

FIG. 9. Cation exchange chromatography of human umbilical cord extracts

CM-TRISACRYL was resuspended in an equal volume of 0.1 M ammonium acetate, pH 4.0, containing 1.0 M NaCl. The resin was allowed to equilibrate for 3 hours and degassed at 4° C. Twenty ml of resin was packed into a 1.6×40 cm column (Pharmacia; #19-0362-01) and washed with 2 column volumes of 1.0 M ammonium acetate. The column was washed until the effluent matched the conductivity and the pH of the equilibrating buffer (0.01 M ammonium acetate pH 4.0) One gram of human umbilical cord acidified, ethanol extract was resuspended in 50 ml of 1.0 M acetic acid and dialyzed against the column equilibration buffer at 4° C. until the pH and the conductivity matched that of the equilibration buffer. The dialyzed acidified, ethanol extract was applied to the column at a flow rate of 1 ml/min at 4° C. and the column was washed with the equilibrating buffer until the absorbance (———), A280, as monitored by a Uvicord S (LKB 2138) with a sensitivity of 1.0 AUFS, was at its lowest point. This was followed by 200 ml of an ascending molarity linear gradient from 0.01 to 1.0 M ammonium acetate, pH 4.0, which was applied using a gradient mixer (Pharmacia GM-1, #19-0495-01). At the end of the gradient, an additional 30 ml of 1.0 M ammonium acetate, pH 4.0, were passed through the column. Two ml fractions were collected in 12×100 mm polystyrene tubes (Columbia Diagnostics B-2564) in a SuperRac fraction collector (LKB 2211). One ml aliquots from each fraction were transferred to 12×75 mm tubes (Falcon 2058) containing 50 µl of 1.0 M acetic acid and 50 µg bovine serum albumin (Sigma A6003), lyophilized, and assayed for TGI activity as described in Materials and Methods. Inhibition of A549 human lung carcinoma cells is shown by open triangles and of mink lung (CCL64) by open circles. The solvent gradient is shown by large dashes (— — —).

Figure 10:
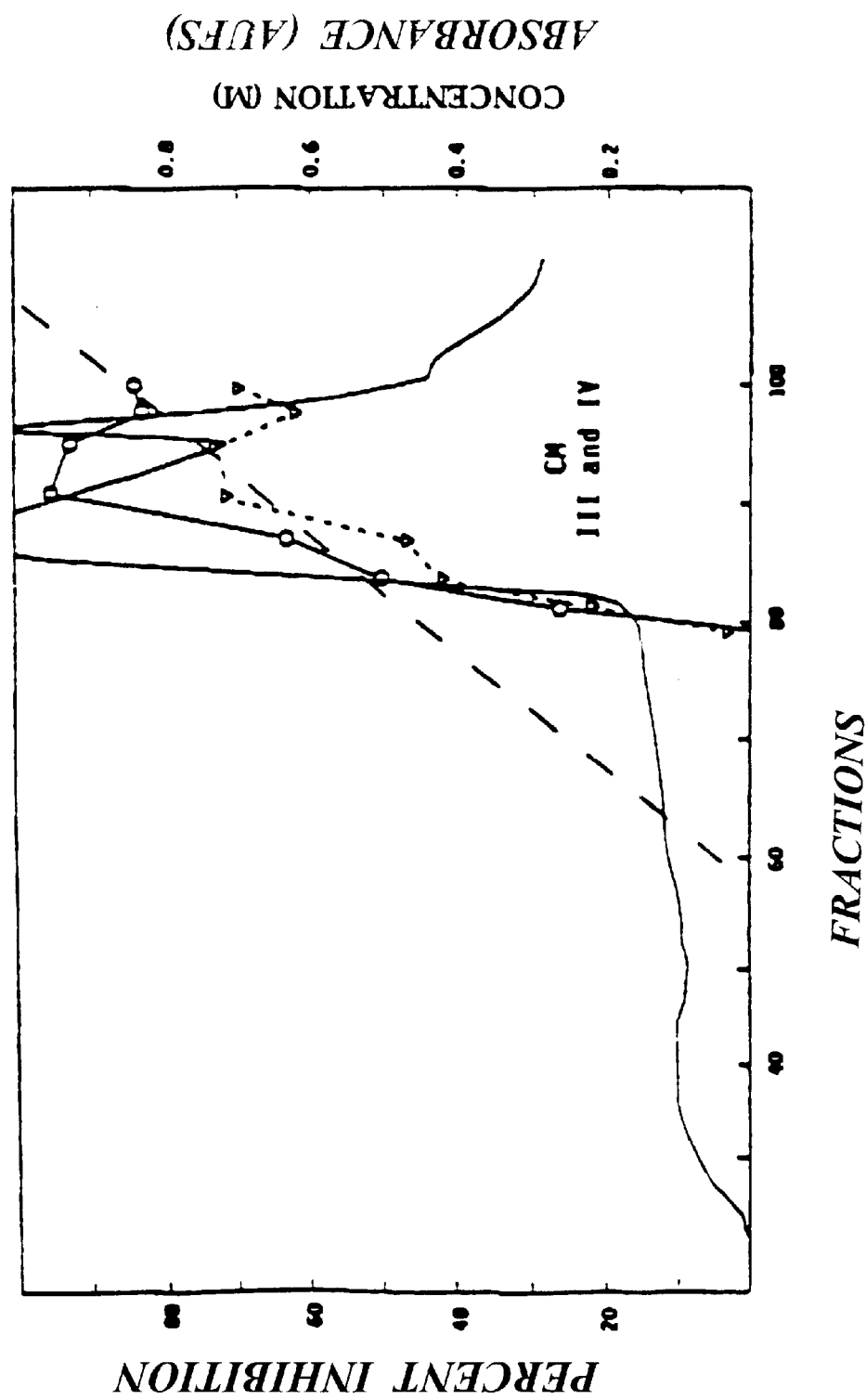

FIG. 10. Rechromatography of a pooled fraction from cation exchange chromatography CM-TRISACRYL was prepared as described in FIG. 9. The material from fractions containing CM-III and CM-IV was pooled, lyphilized, resuspended in 50 ml of 1.0 M acetic acid and dialyzed against the column equilibration buffer at 4° C. until the pH and the conductivity matched that of the equilibration buffer. The sample was applied to the column at a flow rate of 1 ml/min at 4° C. and the column was washed with 120 ml of the equilibrating buffer. Absorbance (———) A280 was monitored by a Uvicord S (LKB 2138) with a sensitivity of 1.0 AUFS. One hundred ml of an ascending molarity linear gradient from 0.01 to 1.0 M ammonium acetate, pH 4.0, was applied using a gradient mixer (Pharmacia; GM-1, #19-0495-01). At the end of the gradient, an additional 30 ml of 1.0 M ammonium acetate, pH 4.0, was passed through the column. Two ml fractions were collected in 12×100 mm polystyrene tubes (Columbia Diagnostics B-2564) in a SuperRac fraction collector (LKB 2211). One ml aliquots from each fraction were transferred to 12×75 mm tubes (Falcon 2058) containing 50 µl of 1.0 M acetic acid and 50 µg bovine serum albumin (Sigma A-6003), lyophilized, and assayed for TGI activity as described in Materials and Methods. Inhibition of A549 human lung carcinoma is shown by open triangles and of mink lung (CCL64) by open circles. The solvent gradient is shown by large dashes (— — —).

Figure 11:
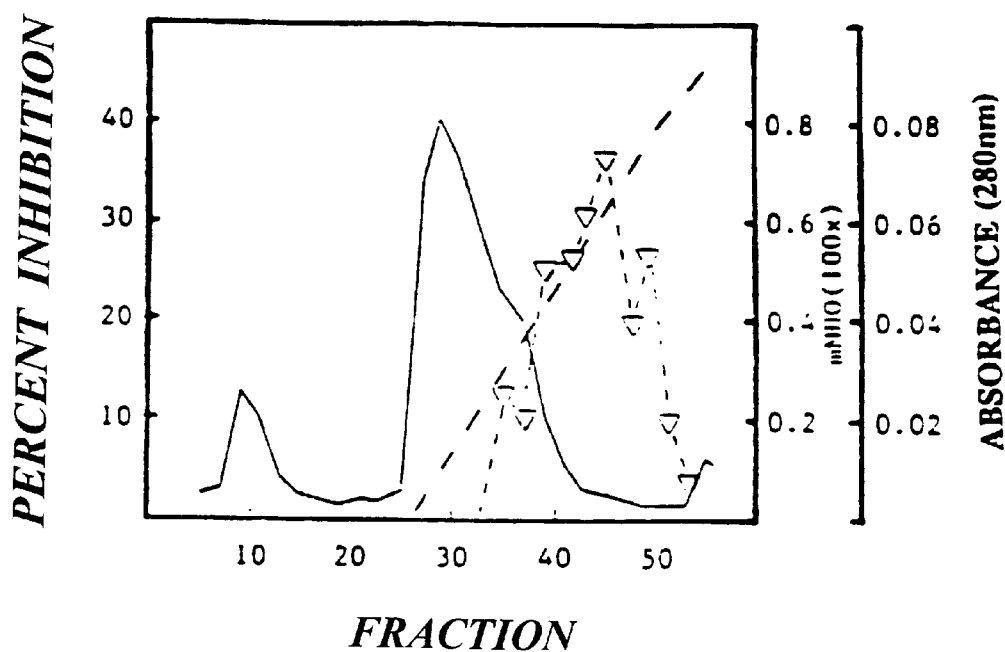

FIG. 11. Fractionation of TGI by cation exchange chromatography at 4° C.

1.65 mg of protein extract prepared as described in the Second Series of Experiments was dialyzed extensively against 20 mM ammonium acetate (pH 4.5) and applied to a 5 ml (1×6.3 cm) column of CM-TRISACRYL previously equilibrated in 20 mM ammonium acetate (pH 4.5) and 1.65 ml fractions (12×100 mm polystrene tubes) were collected. Following sample application, the column was washed with 20 mM ammonium acetate, pH 4.5, until the absorbance at 280 nm (0—0) returned to baseline values (less than 0.003) as determined with a Bausch and Lomb 1001 spectrophotometer using a 1 cm light path quartz cuvette. A linear salt gradient (0–1.0 M NaCl in 20 mM ammonium acetate, pH 4.5) was applied and the absorbance at 280 nm of the 1.65 ml fractions was determined as described above. 10 µl aliquots of the indicated fractions were transferred to 12×75 mm tubes containing 50 µl 1.0 M acetic acid and 50 µg bovine serum albumin (Sigma A-6003), lyophilized, and assayed for inhibitory activity ($^\triangledown$- - -$^\triangledown$) against A549 human lung carcinoma cells as described under Materials and Methods. The NaCl gradient (- - -) was determined by measuring the conductivity (YSI Model 32 Conductance Meter) of suitable samples diluted 100-fold in $H_2O$.

Figure 12:
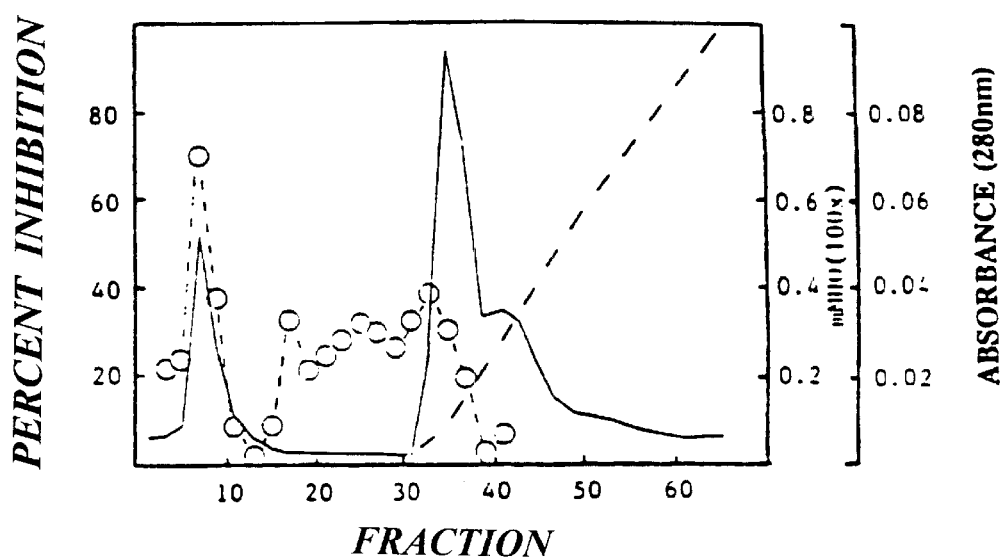

FIG. 12. Fractionation of TGI by Anion Exchange Chromatography at 4° C.

1.65 mg of protein extract prepared as described in the Second Series of Experiments was dialyzed extensively against 20 mM Tris-HCL (pH 8.0) and clarified by centrifugation at 3,000×g for 15 minutes. DEAE-TRISACRYL was prepared by suspending the resin first in 20 mM Tris, HCL (pH 8.0) containing 1.0 M NaCl for 3 hours and secondly in 0.5 M Tris, HCL (pH 8.0) for 1 hour. The sedimented resin was washed on a buchner funnel with 1000 ml H$_2$O and finally resuspended in 20 mM Tris, HCL (pH 8.0), degassed and poured into a 5 ml column (1×6.3 cm) and the resin equilibrated with 20 mM Tris, HCL (pH 8.0). The clarified sample was applied to the column and absorbance at 280 nm (———), inhibitory activity against mink lung cells (0—0), and the NaCl gradient (- - -) was determined as described in FIG. 11 and under Materials and Methods. The linear NaCl gradient in 20 mm Tris, HCL (pH 8.0) ranged from 0 to 1.0 M NaCl.

Figure 13:
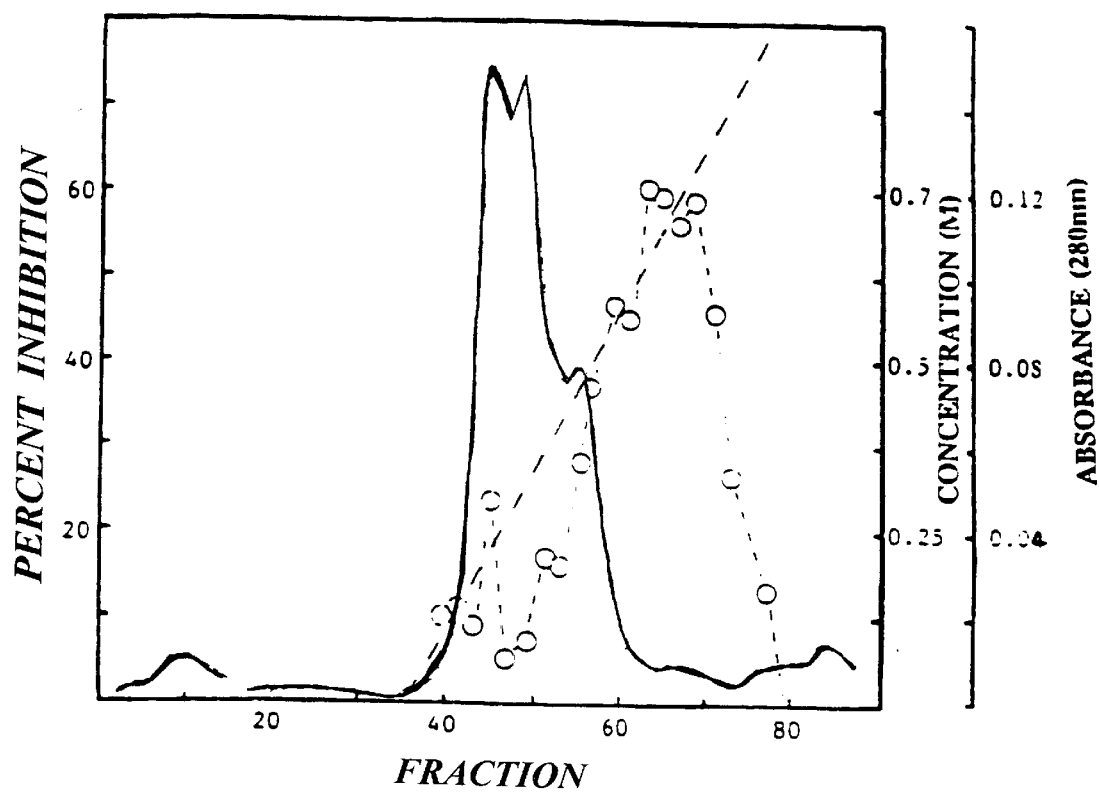

FIG. 13. Fractionation of TGI by cation exchange chromatography of 4° C.

CM-TRISACRYL was prepared as described in FIG. 9. with the exception that the final equilibration buffer was 20 mM ammonium acetate, pH 4.5. Protein extract (9.9 mg) prepared as above was dialyzed extensively against 20 mM ammonium acetate (pH 4.5) and applied to a 15 ml (1.5×8.5 cm) column of CM-TRISACRYL in 20 mM ammonium acetate (pH 4.5). Absorbance at 280 nM (–) and inhibitory activity ($^\triangledown$- -$^\triangledown$- -$^\triangledown$) against A549 human lung carcinoma cells were determined as described in FIG. 11. The volume of the linear 0–1.0 M NaCl gradient was 150 ml. Fraction volume was 3.7 ml.

Figure 14:
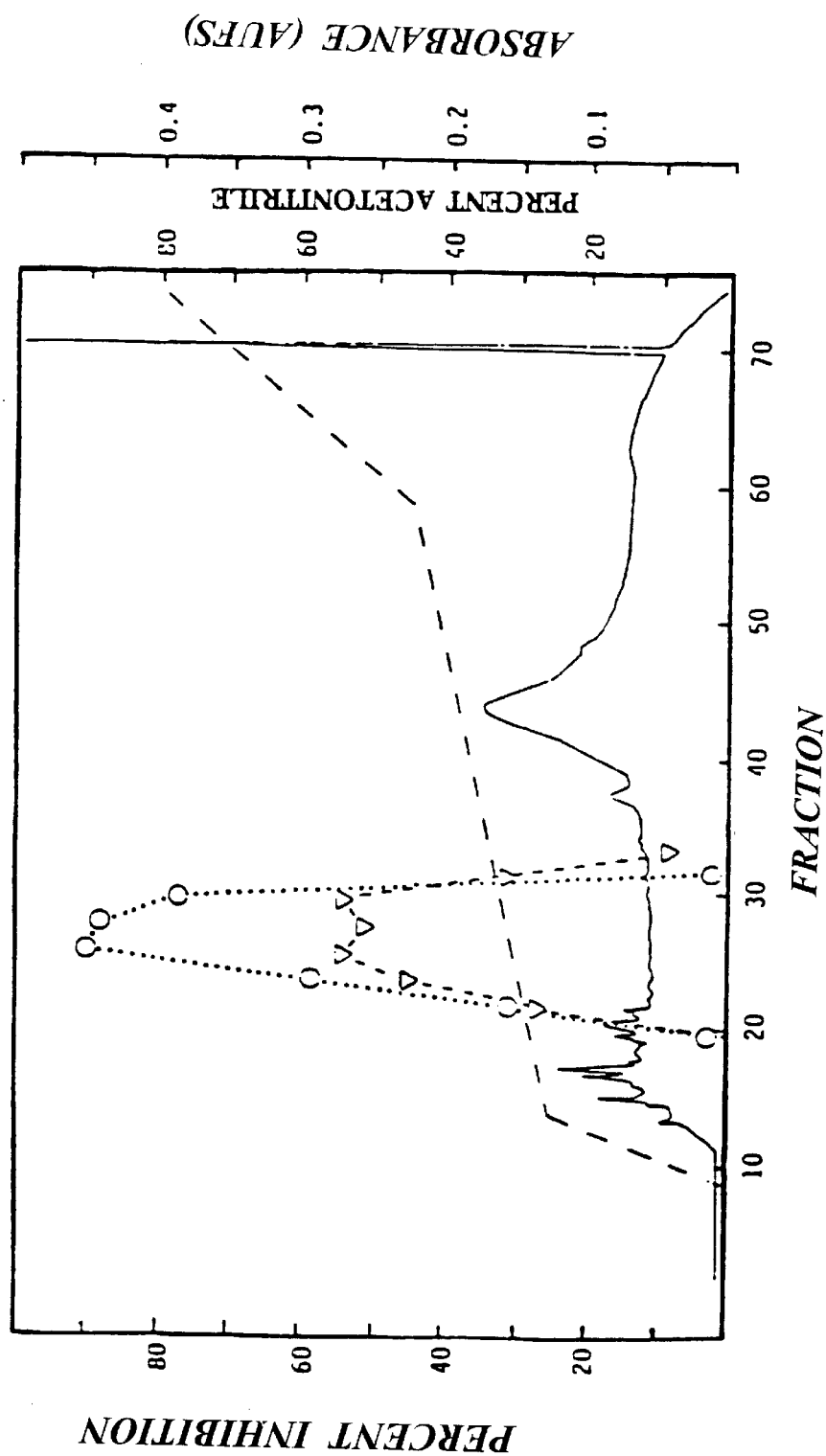

FIG. 14. Reverse phase high performance liquid chromatography (HPLC) of active fractions from cation exchange chromatography Fractions 59 through 78 derived from cation exchange chromatography on CM-TRISACRYL of human umbilical cord described in FIG. 13 were pooled, lyophilized, and resuspended in 10 ml of 0.05% trifluoroacetic acid (TFA). A total of twenty percent of dialyzed material containing 240 μg protein was injected in three separate injections through a Water's U6K injector equipped with a 2 ml sample loop. The sample was then loaded onto a uBondapak C$_{18}$ column (0.39×30 cm) (Waters #27324). The flow rate was 1 ml/min and the effluent monitored at 206 nm (———) with a Waters u.v. detector (Waters Model 481) at a sensitivity of 0.5 AUFS. Elution was achieved with a linear 5-min gradient from 0–25% of increasing concentrations of acetonitrile containing 0.05% TFA, followed by a linear 15-min gradient of 25–45% acetonitrile containing 0.05% TFA, followed by a linear 15-min gradient of 45–80% acetonitrile containing 0.05% TFA, followed by a linear 5-min gradient of 80–100% acetonitrile containing 0.05% TFA. A SuperRac (LKB 2211) was used to collect 1 ml fractions. Five hundred microliter aliquots of every other fraction were transferred to 12×75 mm polystyrene tubes (Falcon 2058) containing 50 μl of 1.0 M acetic acid and 50 μg of bovine serum albumin (Sigma A0281) and assayed for TGI activity as described under Materials and Methods. Inhibition of A549 human lung carcinoma cells is shown by open triangles and of mink lung (CCL64) by open circles. The solvent gradient is shown by large dashes (— — —).

FIG. 15. A comparison of the N-terminal sequences of TGI, TGF-β1, -2 and -3. Only the first twenty-one amino acids are shown. Underlined amino acids show the observed differences between TGF-β1 and TGF-β2, and TGI.

Figure 16:
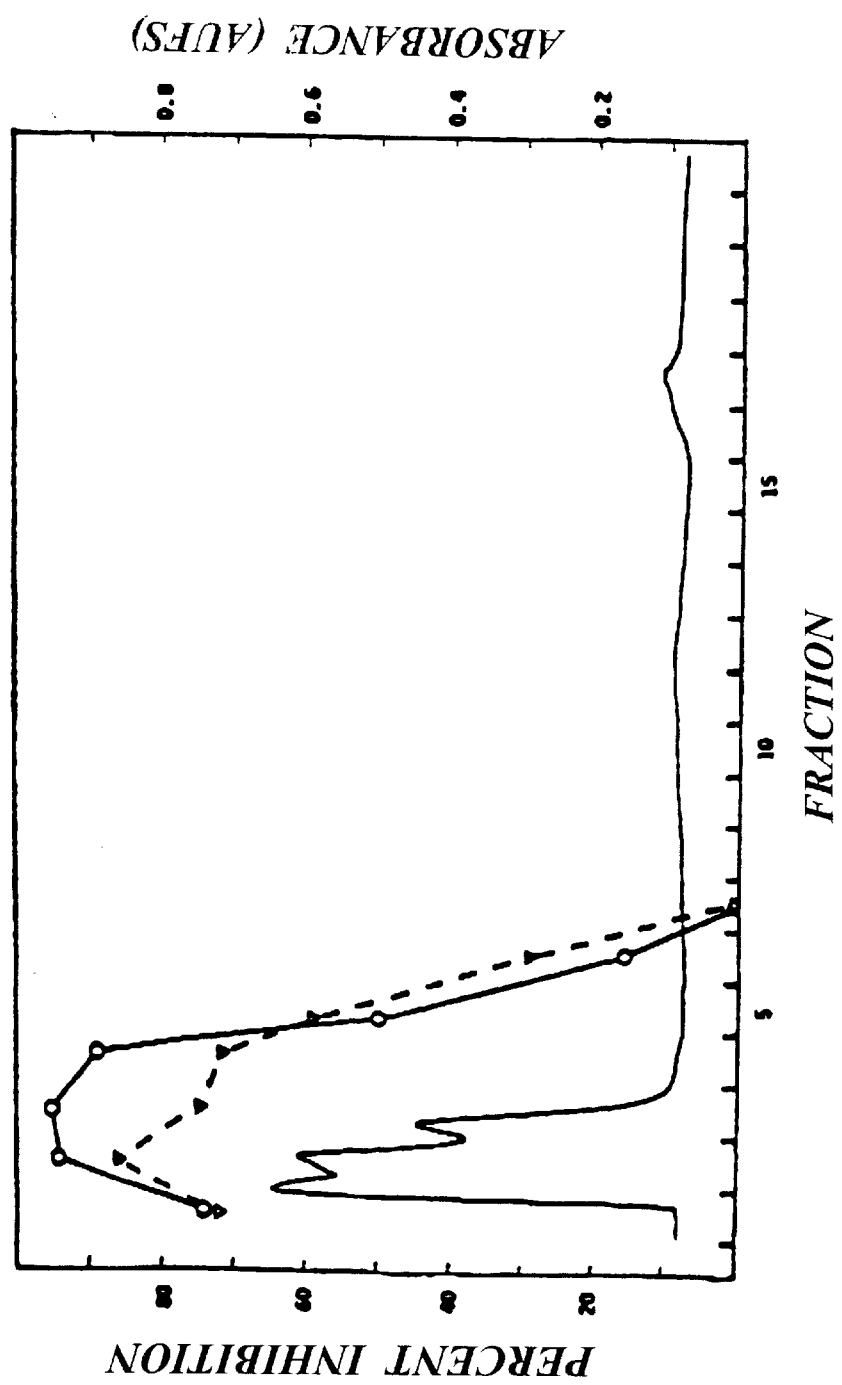

FIG. 16. Gel filtration chromatography at 23° C.

Elution pattern of gel filtration chromatography at 23° C. of crude acidified, ethanol extract from human umbilical cords. Two grams of acidified, ethanol extract in 150 ml of 1.0 M acetic acid was applied to a 14×100 cm column (Amicon; #86012) containing Bio-Gel® P10 and eluted at a flow rate of 7 ml/min. One liter fractions were collected on a SuperRac® (LKB 2211) equipped with a type C collection rack (LKB). One ml aliquots of each fraction (1 liter/fraction) were transferred to 12×75 mm sterile snap top tubes (Falcon 2058). TGI activity was determined as described in Materials and Methods. Inhibition of A549 human lung carcinoma cells is shown by open triangles and mink lung (CCL64) cells by open circles. Absorbance at 280 nm (———) was detected by a Uvicord S (LKB 2138) with a full scale absorbance range of 1.0 AUFS and a single channel chart recorder (LKB 2210) with a chart speed of 1 mm/min.

Figure 17:
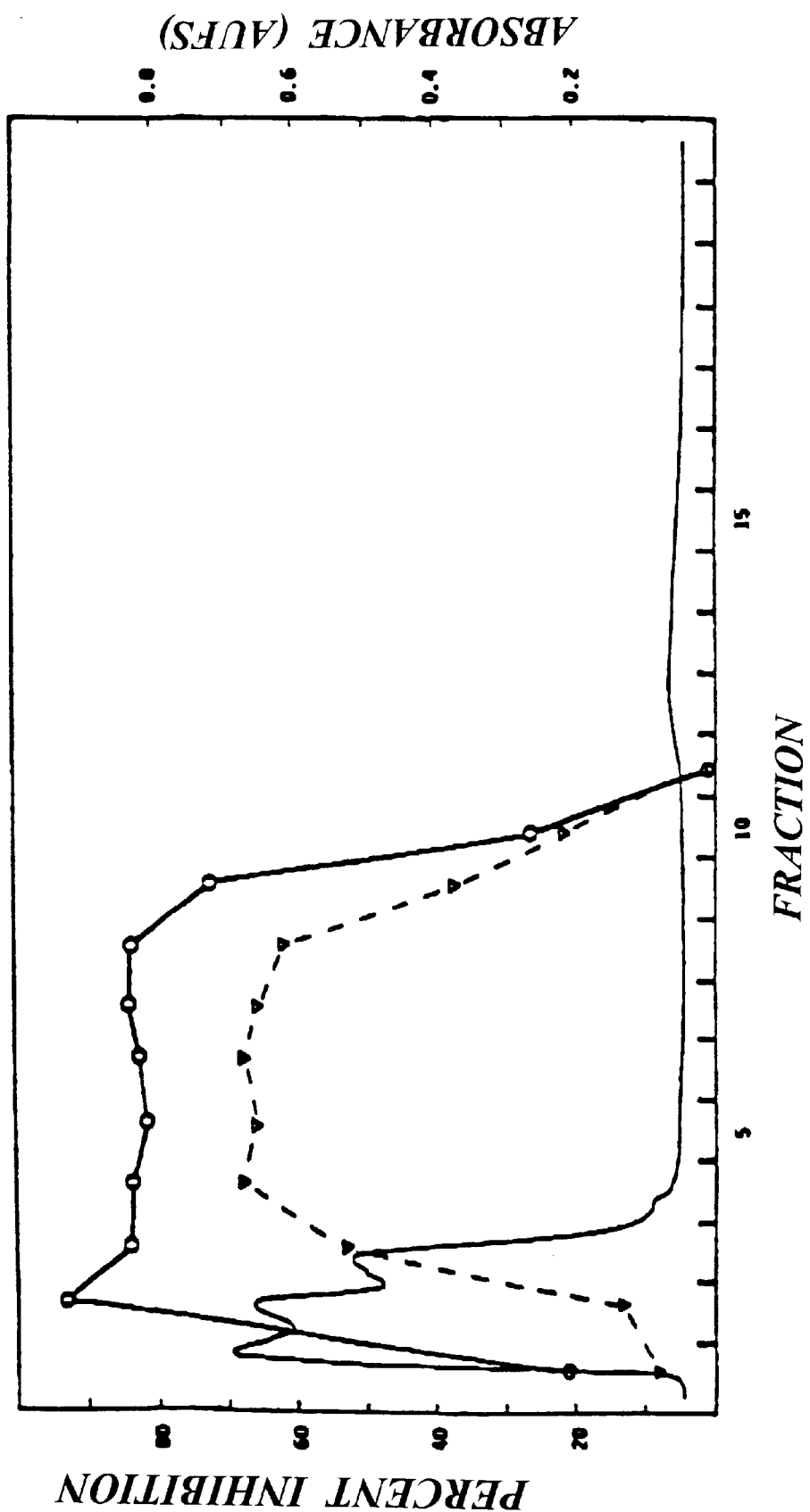

FIG. 17. Gel filtration Chromatography at 4° C.

Elution pattern of gel filtration chromatography at 4° C. of crude acidified, ethanol extract from human umbilical cords. Two grams of acidified, ethanol extract in 150 ml of 1.0 M acetic acid was applied to a 14×100 cm column (Amicon; #86012) containing Bio-Gel® P10 and eluted at a flow rate of 7 ml/min. One liter fractions were collected on a Super-Rac® (LKB 2211) equipped with a type C collection rack (LKB). One ml aliquots of each fraction (1 liter/fraction) were transferred to 12×75 mm sterile snap top tubes (Falcon 1058). Tumor growth inhibitory activity was determined as described in Materials and Methods. Inhibition of A549 human lung carcinoma cells is shown by open triangles and mink lung (CCL64) cells by open circles. Absorbance of 280 nm (———) was detected by a Uvicord® S (LKB 2138) with a full scale absorbance range of 1.0 AUFS and a single channel chart recorder (LKB 2210) with a chart speed of 1 mm/min.

Figure 18:
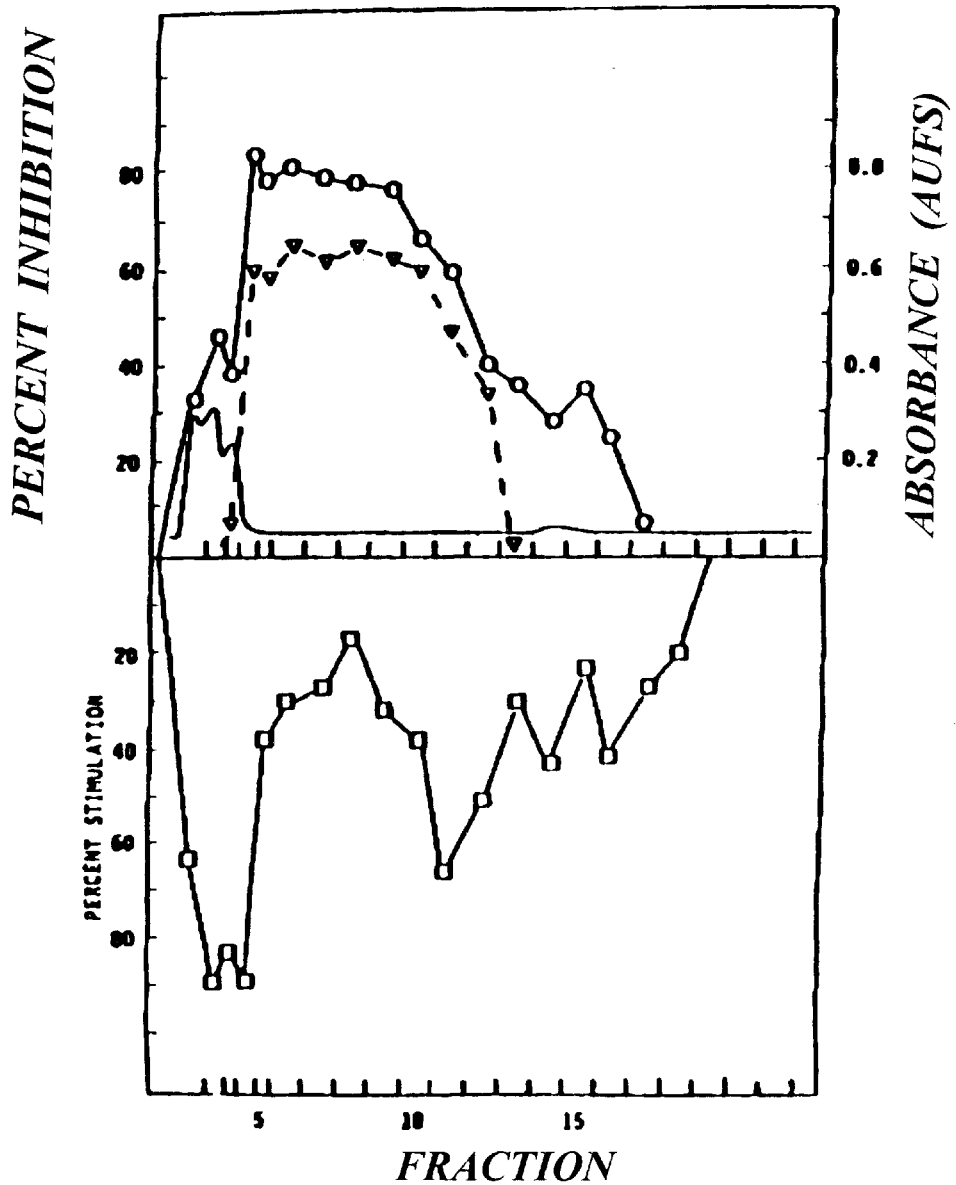

FIG. 18. Cell growth inhibition and normal human cell stimulation by fractions from gel filtration chromatography at 4° C.

Elution pattern of gel filtration chromatography at 4° C. of crude acidified, ethanol extract in 150 ml of 1.0 M acetic acid was applied to a 14×100 cm column (Amicon; #86012) containing Bio-Gel® P10 and eluted at a flow rate of 7 ml/min. One liter fractions were collected on a SuperRac® (LKB 2211) equipped with a type C collection rack (LKB). One ml aliquots of each fraction (1 liter/fraction) were transferred to 12×75 mm sterile snap top tubes (Falcon 2058). Tumor growth inhibitory activity was determined as described in Materials and Methods. Inhibition of A549 human lung carcinoma cells is shown by open triangles and mink lung (CCL64) cells by open circles. Stimulation of normal human fibroblasts is shown by open squares. Absorbance of 280 nm (———) was detected by Uvicord S® (LKB 2138) with a full scale absorbance range of 1.0 AUFS and a single channel chart recorder (LKB 2210) with a chart speed of 1 mm/min.

Figure 19:
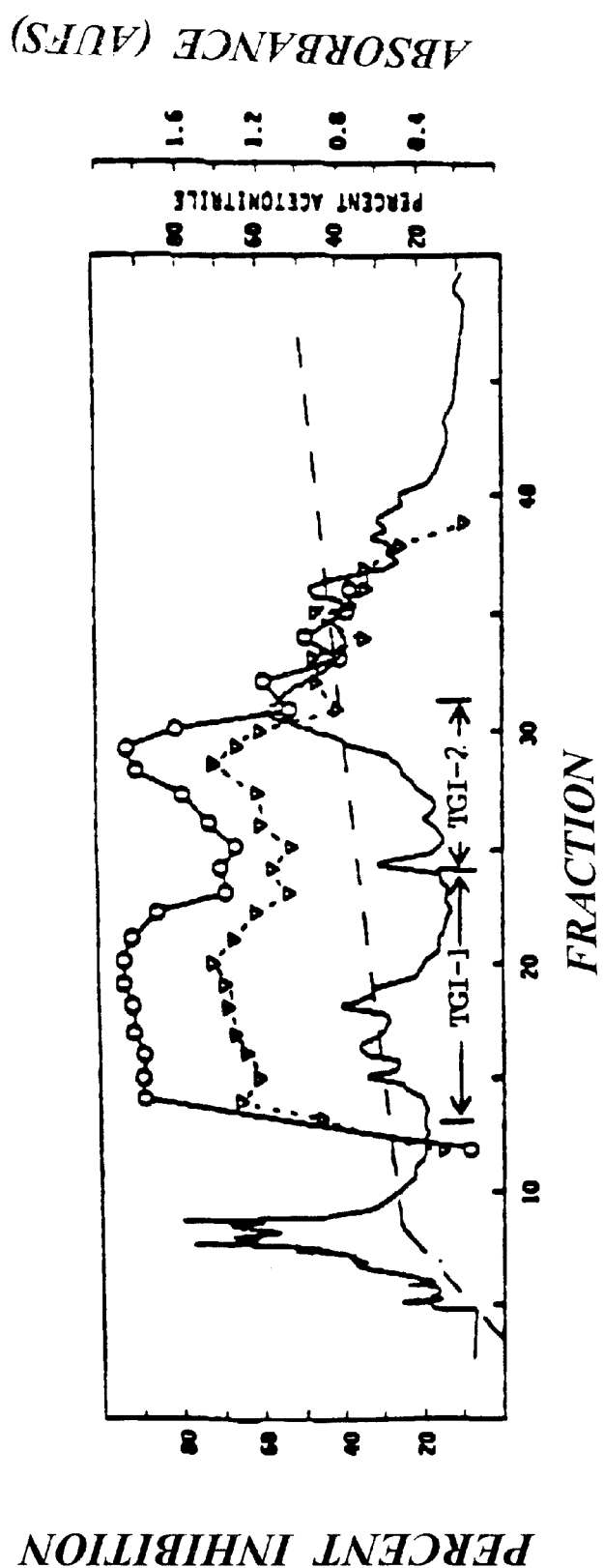

FIG. 19. Reverse phase high performance liquid chromatography (HPLC) of an active fraction from gel filtration chromatography Fraction 4 derived from gel filtration chromatography on Bio-Gel® P10 of human umbilical cord acidified, ethanol extract (65.8 mg protein) was lyophilized and resuspended in 10 ml of 0.05% trifluoroacetic acid (TFA). Fraction 4 was the first fraction following the major peaks of absorbance at 280 nm. (FIG. 2) The sample was centrifuged on a Beckman table top centrifuge (Beckman TJ-6) at 3000 rpm for 20 minutes to remove insoluble material. Three separate injections of the supernatant were made through a Water's U6K injector equipped with a 2 ml sample loop. The sample was then loaded onto a uBONDAPAK® C$_{18}$ column (0.78×30 cm) (Waters #84176). The flow rate was 2 ml/min. and the effluent monitored at 206 nm (_____) with a Waters u.v. detector (Waters Model 481) at a sensitivity of 2.0 AUFS. Elution was achieved with a linear 30-min gradient from 0.25% of increasing concentrations of acetonitrile containing 0.05% trifluoroacetic acid (TFA), followed by a linear 240-min gradient of 25–45% acetonitrile containing 0.05% TFA, followed by a linear 30-min gradient of 45–100% acetonitrile containing 0.05% TFA. A SuperRac® (LKB 2211) was used to collect 12 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma B) and assayed for tumor growth inhibitory activity as described in Materials and Methods. Inhibition of A549 human lung carcinoma cells is shown by open triangles and of mink lung (CCL 64) by open circles. The solvent gradient is shown by large dashes (— — —).

Figure 20:
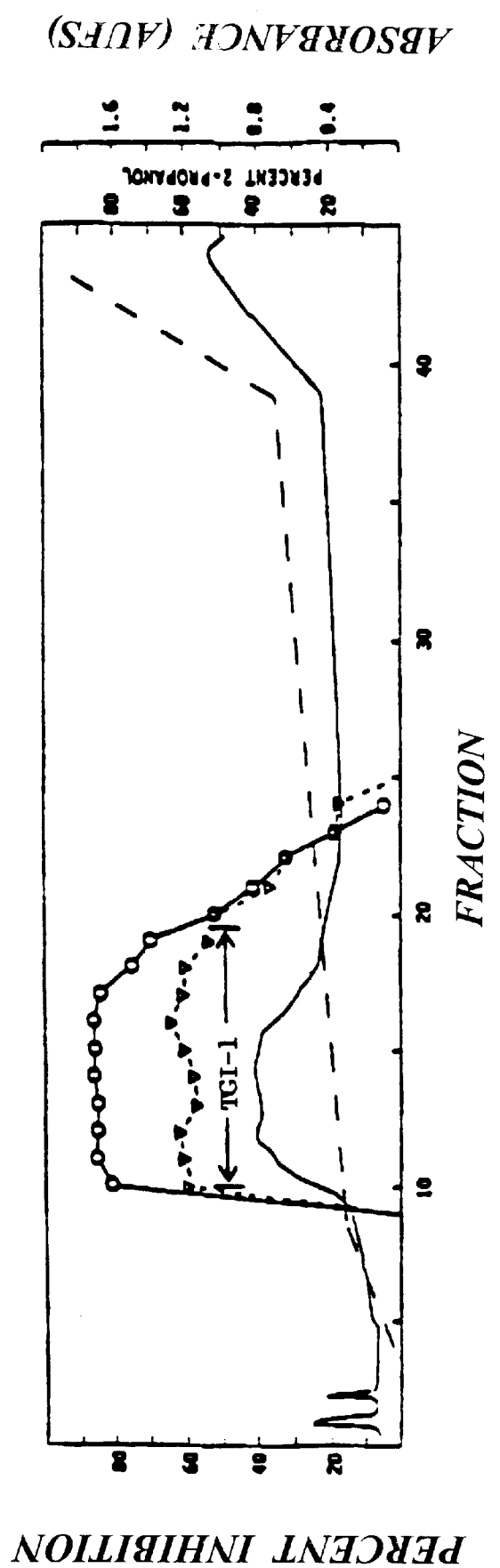

FIG. 20. HPLC rechromatography of pooled TGI activity from HPLC (TGI-1)

Pooled fractions of tumor growth inhibitory activity (1.5 mg) eluting between 28–34% acetonitrile (fractions 13–22) by HPLC chromatography (FIG. 4) were lyophilized and resuspended in 2 ml of 0.05% trifluoroacetic acid (TFA). The sample was centrifuged on a Beckman table top centrifuge (Beckman TJ-6) at 3000 rpm for 20 minutes to remove insoluble material. Two separate injections of the supernatant were made through a Water's U6K injector equipped with a 2 ml sample loop. The sample was loaded onto a uBONDAPAK® $C_{18}$ column (0.39×30 cm) (Waters #27324). The flow rate was 1 ml/min. and the effluent monitored at 206 nm (_____) with a Waters u.v. detector (Waters Model 481) at a sensitivity of 2.0 AUFS. Elution was achieved with a linear 20-min gradient from 0–15% of increasing concentrations of 2-propanol containing 0.05% TFA, followed by a linear 120-min gradient of 15–35% 2-propanol containing 0.05% TFA. A SuperRac® (LKB 2211) was used to collect 4 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma A-6003) and assayed for tumor growth inhibitory activity as described in Materials and Methods. Inhibition of A549 human lung carcinoma cells is shown by open triangles and of mink lung (CCL64) by open circles. The solvent gradient is shown by large dashes (— — —).

Figure 21:
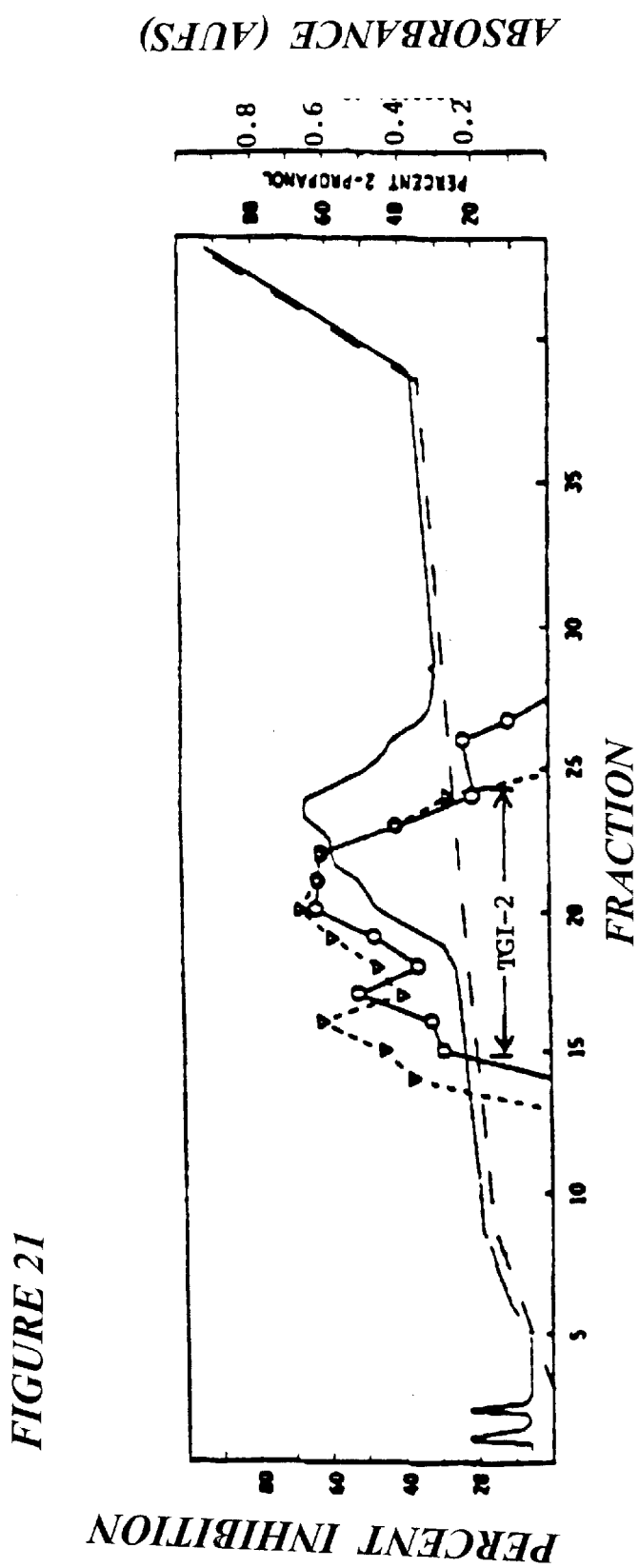

FIG. 21. Reverse phase HPLC rechromatography of pooled activity from HPLC (TGI-2)

Pooled fractions of tumor growth inhibitory activity (0.8 mg) eluting between 35–39% acetonitrile (fractions 25–31) by HPLC chromatography (FIG. 4) were lyophilized and resuspended in 2 ml of 0.05% trifluoroacetic acid (TFA). The sample was centrifuged on a Beckman table top centrifuge (Beckman TJ-6) at 3000 rpm for 30 minutes to remove insoluble material. Two separate injections of the supernatant were made through a Water's U6K injector equipped with a 2 ml sample loop. The sample was loaded onto a uBONDAPAK® $C_{18}$ column (0.39×30 cm) (Waters #27324). The flow rate was 1 ml/min and the effluent monitored at 206 nm (_____) with a Waters u.v. detector (Waters Model 481) at a sensitivity of 1.0 AUFS. Elution was achieved with a linear 20-min gradient from 0.15% of increasing concentrations of 2-propanol containing 0.05% TFA, followed by a linear 120-min gradient of 15–35% 2-propanol containing 0.05% TFA. A SuperRac® (LKB 2211) was used to collect 4 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma A-6003) and assayed for tumor growth inhibitory activity as described in Materials and Methods. Inhibition of A549 human lung carcinoma cells is shown by open triangles and of mink lung (CCL64) by open circles. The solvent gradient is shown by large dashes (— — —).

Figure 22:
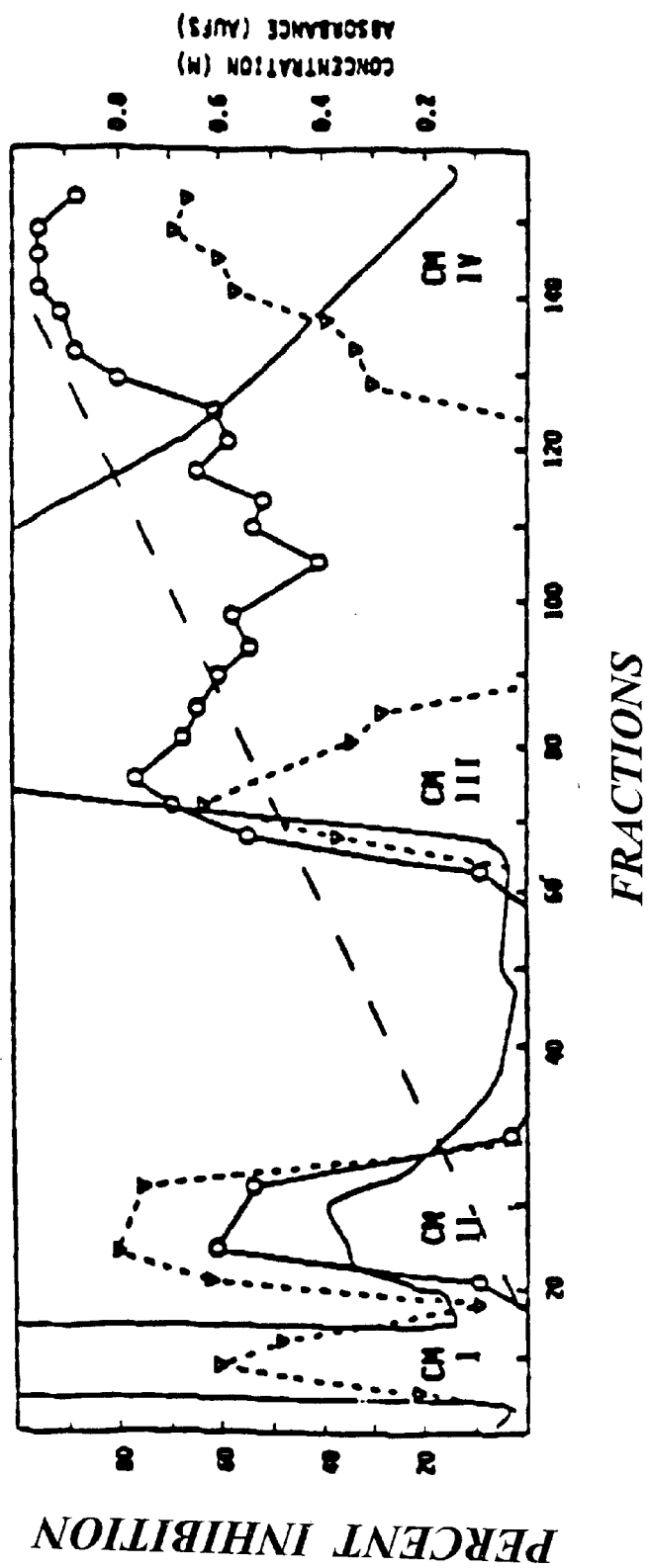

FIG. 22. Cation exchange chromatography of human umbilical cord extracts

CM-TRISACRYL was resuspended in an equal volume of 0.1 M ammonium acetate, pH 4.0, containing 1.0 M NaCl. The resin was allowed to equilibrate for 3 hours and degassed at 4° C. Twenty ml of resin was packed into a 1.6×40 cm column (Pharmacia; #19-0362-01) and washed with 2 column volumes of 1.0 M ammonium acetate pH 4.0, followed by 0.01 M ammonium acetate. The column was washed until the effluent matched the conductivity and the pH of the equilibrating buffer (0.01 M ammonium acetate pH 4.0). One gram of human umbilical cord acidified, ethanol extract was resuspended in 50 ml of 1.0 M acetic acid and dialyzed against the column equilibration buffer at 4° C. until the pH and the conductivity matched that of the equilibration buffer. The dialyzed acidified, ethanol extract was applied to the column at a flow rate of 1 ml/min at 4° C. and the column was washed with the equilibrating buffer until the absorbance (_____), A280, as monitored by a Uvicord® S (LKB 2138) with a sensitivity of 1.0 AUFS, was at its lowest point. This was followed by 200 ml of an ascending molarity linear gradient from 0.01 to 1.0 M ammonium acetate, pH 4.0, which was applied using a gradient mixer (Pharmacia GM-1, #19-0495-01). At the end of the gradient, an additional 30 ml of 1.0 M ammonium acetate, pH 4.0, were passed through the column. Two ml fractions were collected in 12×100 mm polystyrene tubes (Columbia Diagnostics B-2564) in a SuperRac fraction collector (LKB 2211). One ml aliquots from each fraction were transferred to 12×75 mm tubes (Falcon 2058) containing 50 microliters 1.0 M acetic acid and 50 micrograms bovine serum albumin (Sigma A6003), lyophilized, and assayed for tumor growth inhibitory activity as described in Materials and Methods. Inhibition of A549 human lung carcinoma cells is shown by open triangles and of mink lung (CCL64) cells by open circles. The solvent gradient is shown by large dashes (— — —).

Figure 23:
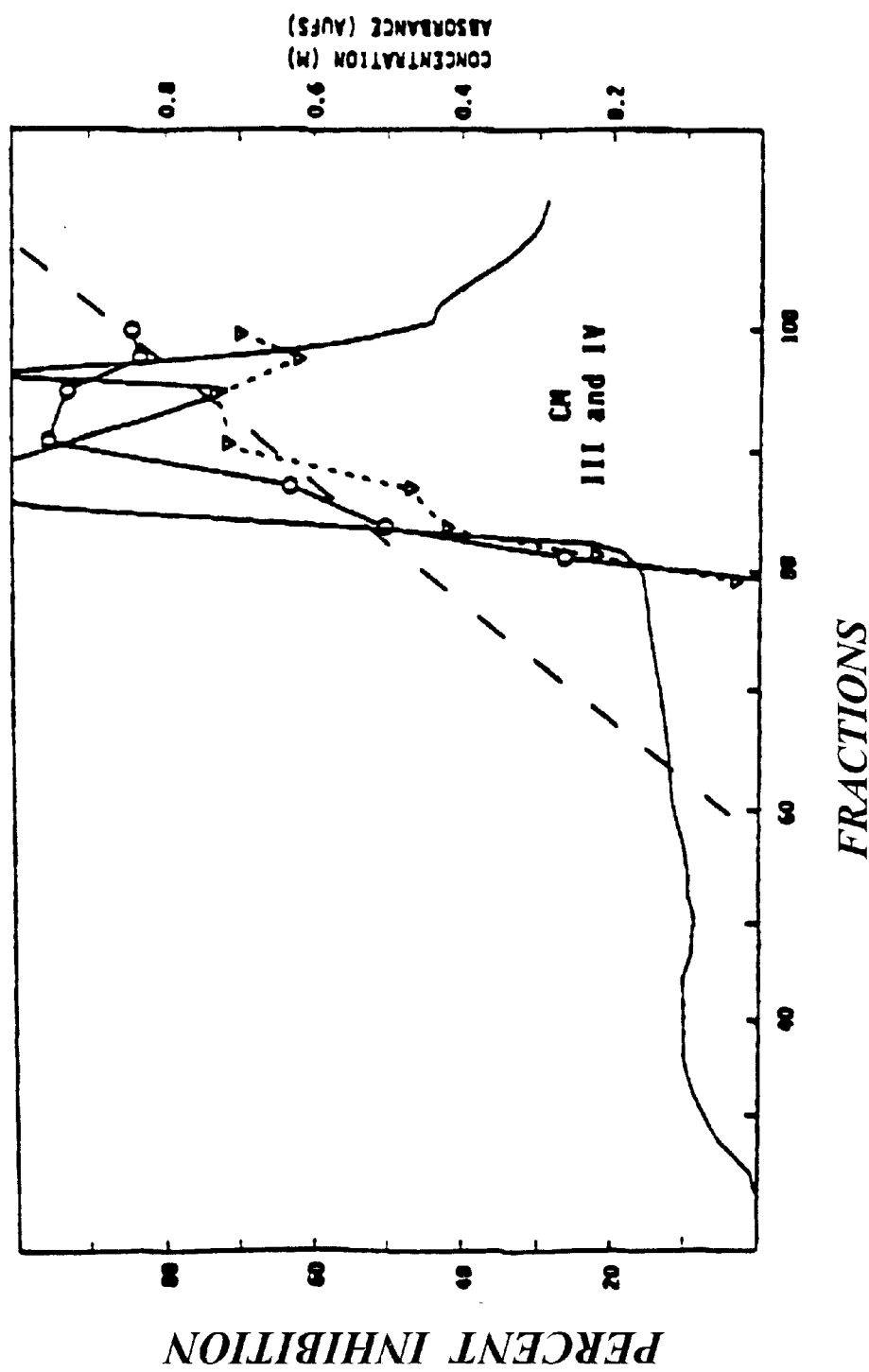

FIG. 23. Rechromatography of a pooled fraction from cation exchange chromatography CM-TRISACRYL was prepared as described in FIG. 9. The material from fractions containing CM III and CM IV were pooled, lyophilized, resuspended in 50 ml of 0.1 M acetic acid and dialyzed against the column equilibration buffer at 4° C. until the pH and the conductivity matched that of the equilibration buffer. The sample was applied to the column at a flow rate of 1 ml/min at 4° C. and the column was washed with 120 ml of the equilibrating buffer. Absorbance (_____) (280 nm) was monitored by a Uvicord S (LKB 2138) with a sensitivity of 1.0 AUFS. One hundred ml of an ascending molarity linear gradient from 0.01 to 1.0 M ammonium acetate, pH 4.0, was applied using a gradient mixer (Pharmacia; GM-1, #19-0495-01). At the end of the gradient, an additional 30 ml of 1.0 M ammonium acetate, pH 4.0, was passed through the column. Two ml fractions were collected in 12×100 mm polystyrene tubes (Columbia Diagnostics B-2564) in a SuperRac® fraction collector (LKB 2211). One ml aliquots from each fraction were transferred to 12×75 mm tubes (Falcon 2058) containing 50 microliters 1.0 M acetic acid and 50 micrograms bovine serum albumin (Sigma A6003), lyophilized, and assayed for tumor growth inhibitory activity as described in Materials and Methods. Inhibition of A549 human lung carcinoma cells is shown by open triangles and mink lung (CCL64) cells by open circles. The salt gradient is shown by large dashes (— — —).

Figure 24:
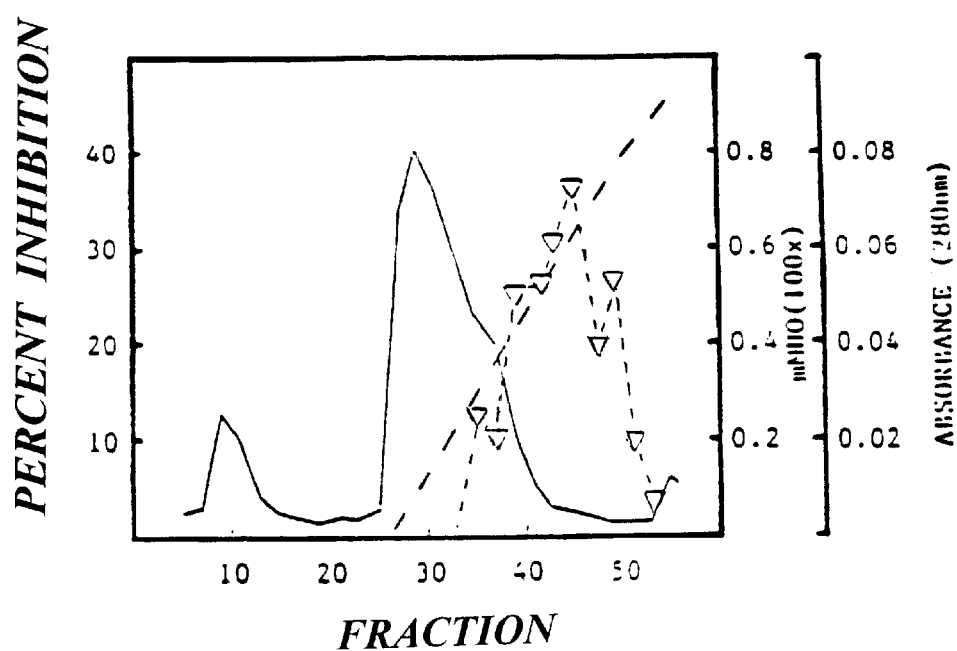

FIG. 24. Fractionation of TGI by Cation Exchange Chromatography at 4°-C 1.65 mg of protein extract prepared as described in the Second Series of Experiments was dialyzed extensively against 20 mM ammonium acetate (pH 4.5) and applied to a 5 ml (1×6.3 cm) column of CM-TRISACRYL previously equilibrated in 20 mM ammonium acetate (pH 4.5) and 1.65 ml fractions (12×100 mm polystyrene tubes) were collected. Following sample application, the column was washed with 20 mM ammonium acetate, pH 4.5, until the absorbance at 280 nm (0—0) returned to baseline values (less than 0.003) as determined with a Bausch and Lomb 1001 spectrophotometer using a 1 cm light path quartz cuvet. A linear salt gradient (0–1.0 M NaCl in 20 mM ammonium acetate, pH 4.5) was applied and the absorbance at 280 nm of the 1.65 ml fractions was determined as described above. 10 microliters aliquots of the indicated fractions were transferred to 12×75 mm tubes containing 50 ul 1.0 M acetic acid and 50 micrograms bovine serum albumin (Sigma A6003), lyophilized, and assayed for inhibitory activity ($\triangledown$- - -$\triangledown$) against A549 human lung carcinoma cells as described under Materials and Methods. The NaCl gradient (— — —) was determined by measuring the conductivity (YSI Model 32 Conductance Meter) of suitable samples diluted 100-fold in $H_2O$.

Figure 25:
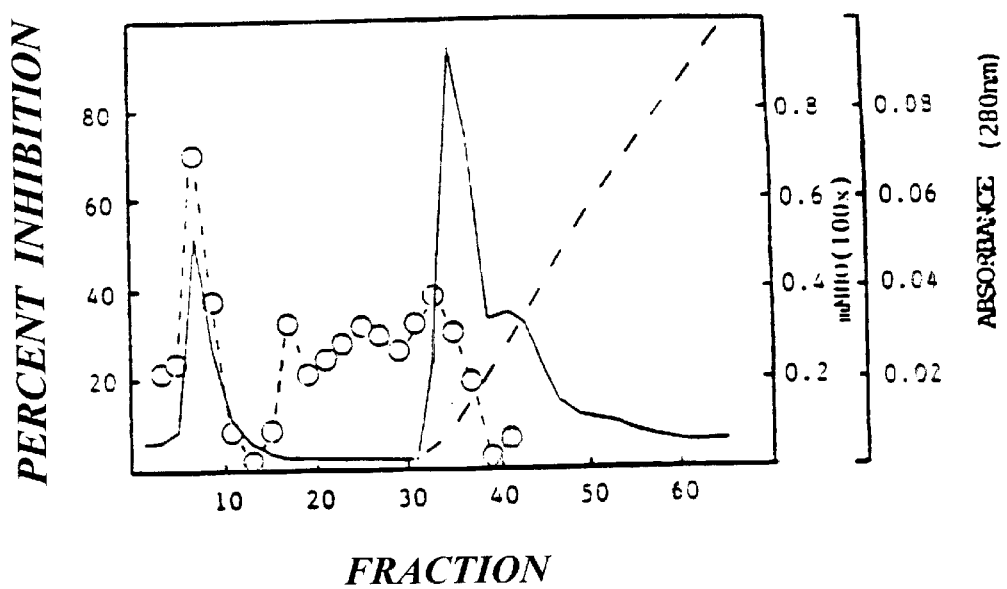

FIG. 25. Fractionation of TGI by Anion Exchange Chromatography at 4° C.

1.65 mg of protein extract prepared as described in the Second Series of Experiments was dialyzed extensively against 20 mM Tris-HCl (pH 8.0) and clarified by centrifugation at 3,000×g for 15 minutes. DEAE-TRISACRYL CRYL was prepared by suspending the resin first in 20 mM Tris, Hcl (pH 8.0) containing 1.0 M NaCl for 3 hours and secondly in 0.5 M Tris, HCl (pH 8.0) for 1 hour. The sedimented resin was washed on a buchner funnel with 1000 ml $H_2O$ and finally resuspended in 20 mM Tris, HCl (pH 8.0), degassed and poured into a 5 ml column (1×6.3 cm) and the resin equilibrated with 20 mM Tris, HCl (pH 8.0). The clarified sample was applied to the column and absorbance at 280 nm(_____), inhibitory activity against mink lung cells (0—0), and the NaCl gradient (— — —) was determined as described in FIG. 24 and under Materials and Methods. The linear NaCl gradient in 20 mm Tris, HCl (pH 8.0) ranged from 0 to 1.0 M NaCl.

Figure 26:
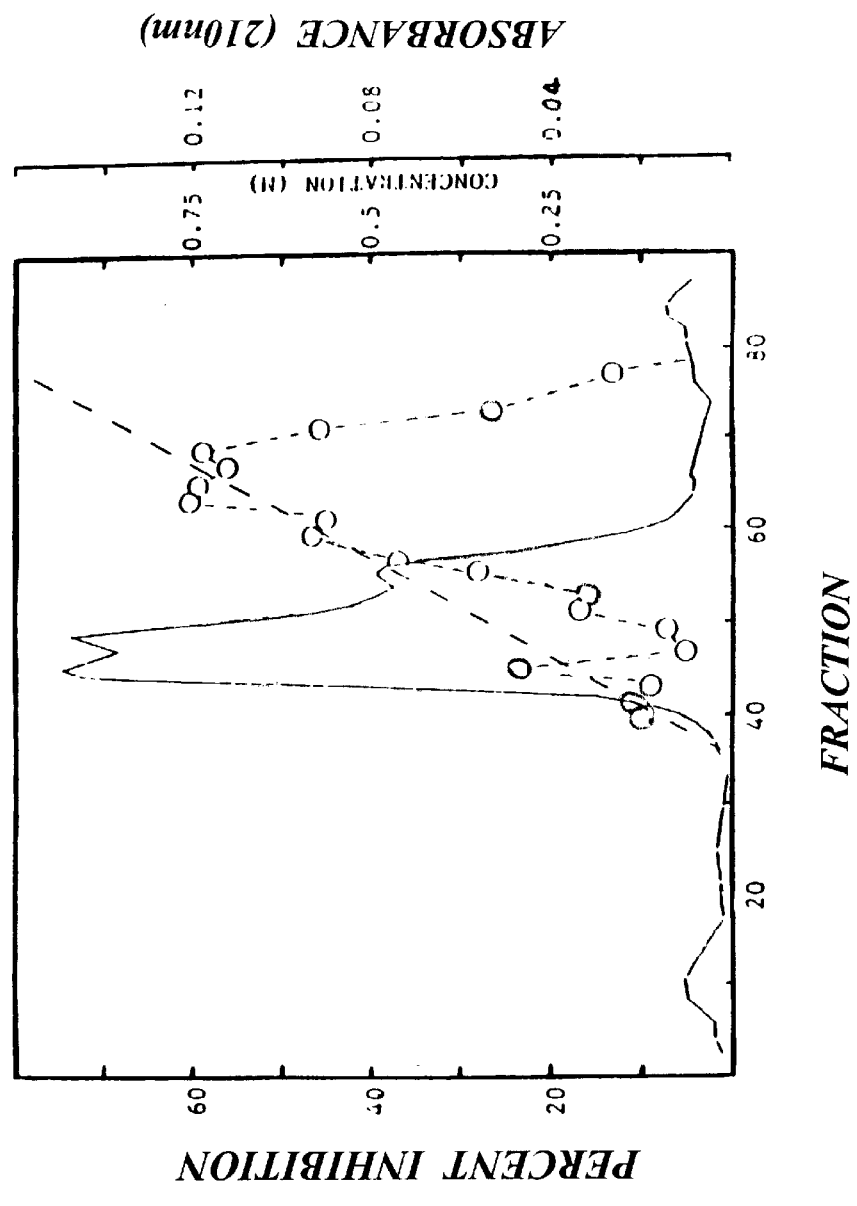

FIG. 26. Fractionation of TGI by Cation Exchange Chromatography at 4° C.

CM-TRISACRYL® was prepared as described in FIG. 7 with the exception that the final equilibration buffer was 20 mM ammonium acetate, pH 4.5. Protein extract (9.9 mg) prepared as above was dialyzed extensively against 20 mM ammonium acetate (pH 4.5) and applied to a 15 ml (1.5×8.5 cm) column of CM-TRISACRYL in 20 mM ammonium acetate (pH 4.5). Absorbance at 280 nM (–) and inhibitory activity ($\triangledown$-$\triangledown$-$\triangledown$) against A549 human lung carcinoma cells were determined as described in FIG. 22. The volume of the linear 0–1.0 M NaCl gradient was 150 ml. Volume of each fraction was 3.7 ml.

Figure 27:
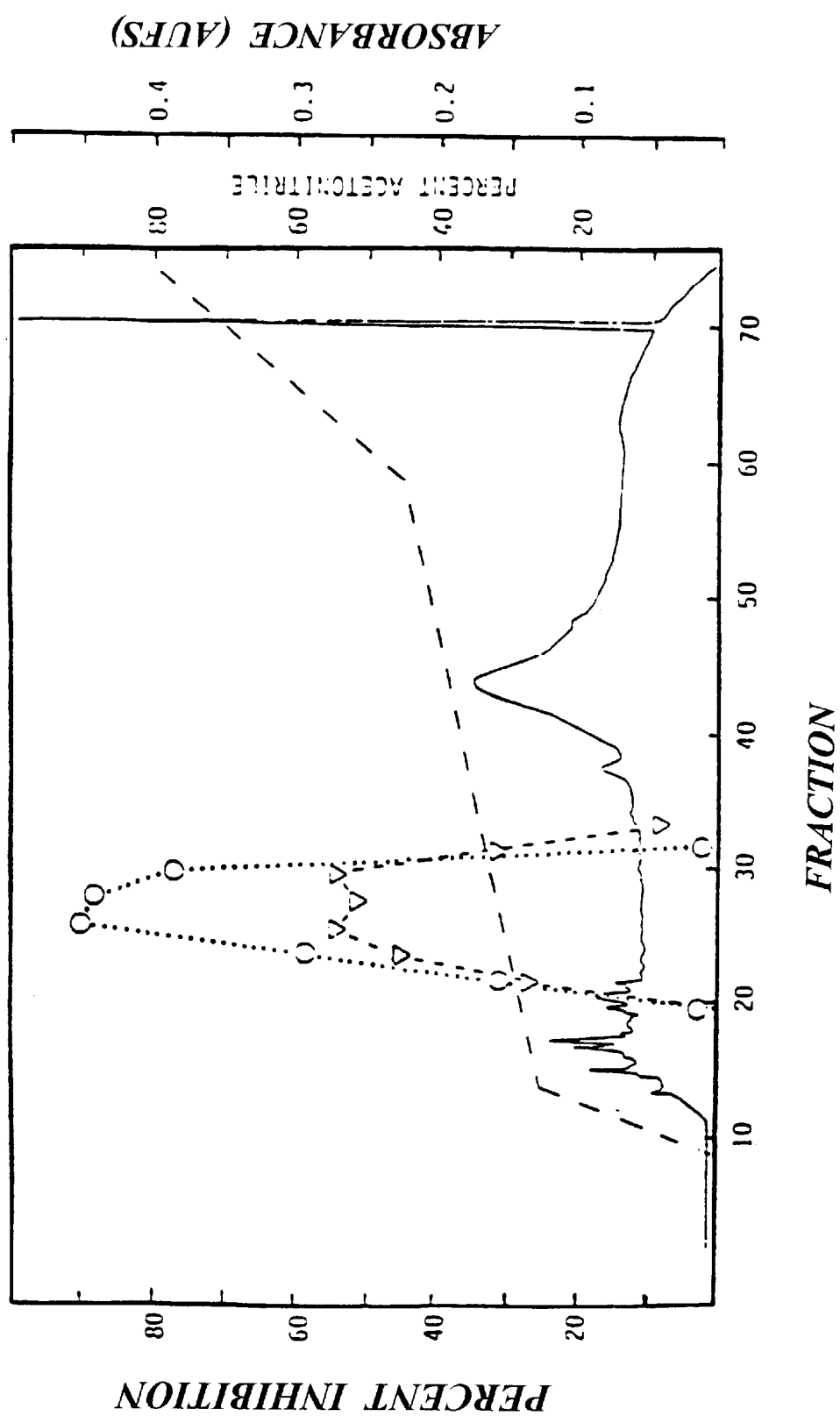

FIG. 27. Reverse phase high performance liquid chromatography (HPCL) of active fractions from cation exchange chromatography Fractions 59 thru 78 derived from cation exchange chromatography on CM-TRISACRYL of human umbilical cord described in FIG. 13 were pooled, lyophilized, and resuspended in 10 ml of 0.05% trifluoracetic acid (TFA). A total of twenty percent of dialyzed material containing 240 micrograms protein was injected in three separate injections through a Water's U6K injector equipped with a 2 ml sample loop. The sample was then applied onto a uBONDAPAK® $C_{18}$ column (0.39×30 cm) (Waters 27324). The flow rate was 1 ml/min and the effluent was monitored at 206 nm (_____) with a Waters u.v. detector (Waters Model 481) at a sensitivity of 0.5 AUFS. Elution was achieved with a linear 5-min gradient from 0–25% of increasing concentrations of acetonitrile containing 0.05% TFA, followed by a linear 15-min gradient of 25–45% acetonitrile containing 0.05% TFA, followed by a linear 15-min gradient of 45–80% acetonitrile containing 0.05% TFA, followed by a linear 5-min gradient of 80–100% acetonitrile containing 0.05% TFA. A Super-Rac® (LKB 2211) was used to collect 1 ml fractions. Five hundred microliter aliquots of every other fraction were transferred to 12×75 mm polystyrene tubes (Falcon 2058) containing 50 microliters of 1.0 M acetic acid and 50 micrograms of bovine serum albumin (Sigma A0281) and assayed for tumor growth inhibitory activity as described under Materials and Methods. Inhibition of A549 human lung carcinoma cells is shown by open triangles and of mink lung (CCL64) cells by open circles. The solvent gradient is shown by large dashes (— — —).

Figure 28:
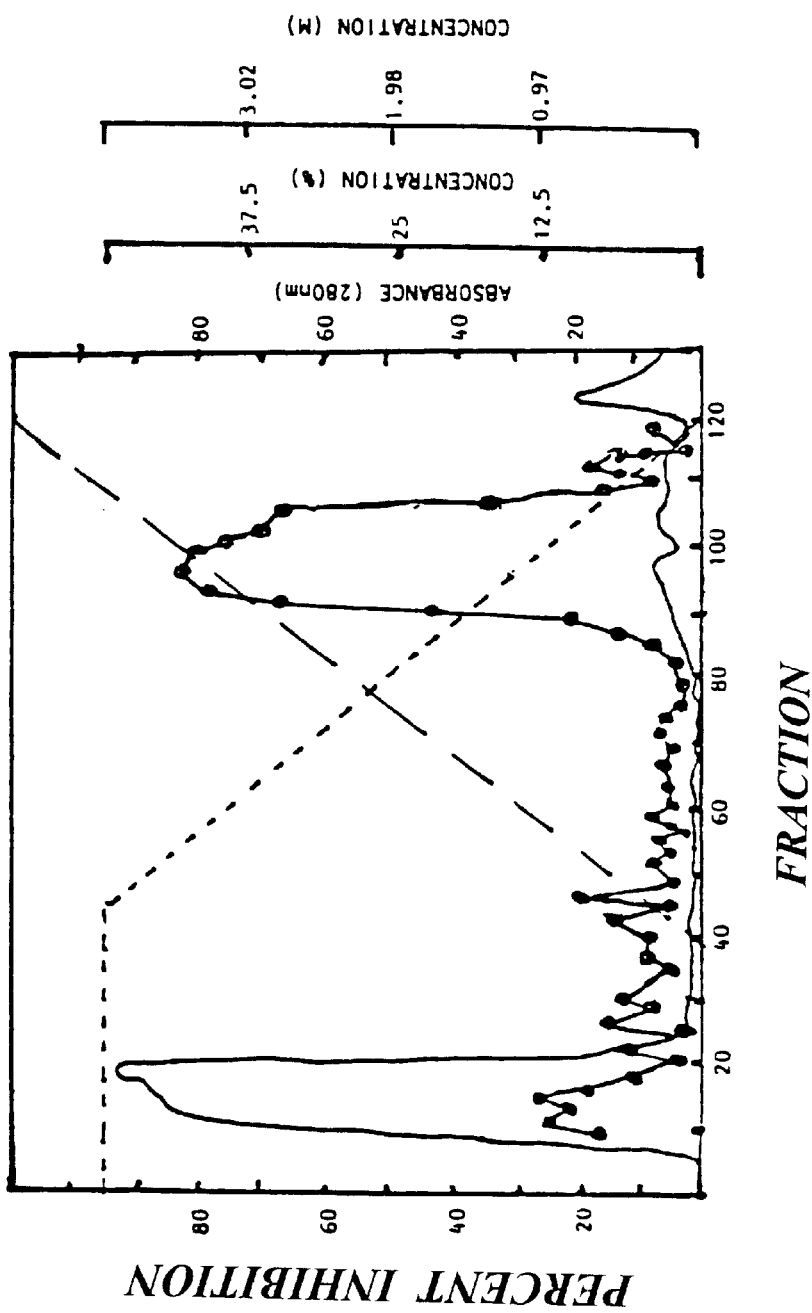

FIG. 28. Hydrophobic Interaction Chromatography—phenyl Sepharose.

Phenyl-Sepharose™ (Pharmacia) was equilibrated with 4.0 M ammonium acetate, pH 4.5 and 15 ml of resin poured into a 1.5×20 cm column (Pharmacia). Thirty-one mg of ether, ethanol precipitated TGI in 36.0 ml which was equilibrated by dialysis in Spectropor 3 (molecular weight cutoff 3,500) in 4.0 M ammonium acetate, was applied to the column at a flow rate of 1.0 ml/min. After the $OD_{280}$ of element reached zero, a gradient containing a descending concentration of 4.0 M to 0.04 M ammonium acetate (short broken lines) and an ascending concentraction of ethylene glycol (Mallinkrodt) from 0–50% (long broken lines), pH 4.5 was applied through a flow adaptor (Pharmacia AC16). The total volume of the gradient was 150 ml and 1.9 ml fractions were collected by a Redirac® fraction collector (LKB). Thirty microliters of every other fraction was transferred to a sterile plastic 12×75 mm snap-top tubes (Falcon) containing 50 micrograms of bovine serum albumin (BSA-Sigma) in 1.0 M acetic acid. Tumor growth inhibitory activity was determined for both CCL 64 mink lung cells and A549 cells as described in the initial procedure. Activity against A549 cells is not shown because the activity (profiles were similar). Tumor growth inhibitory activity is plotted as percent inhibition and is illustrated by closed circles. The peak of growth inhibitory activity was eluted at 1.18 M ammonium acetate, 42% ethylene glycol. Protein concentration is indicated as absorbance at 280 nm and was determined using a spectrophotometer (Baush & Lomb, Spectronic® 1001). Biologically active fractions 90–100 were pooled and dialyzed against 0.1 M acetic acid. The protein concentration of the pooled fractions was determined by absorbance at $OD_{280}$. The recovered protein was 1.4 mg (see Table 7). The quantity of inhibitory units applied was $1.56 \times 10^6$ in 30.9 mg and the amount recovered was $1.5 \times 10^6$ in 1.4 mg.

Figure 29A:
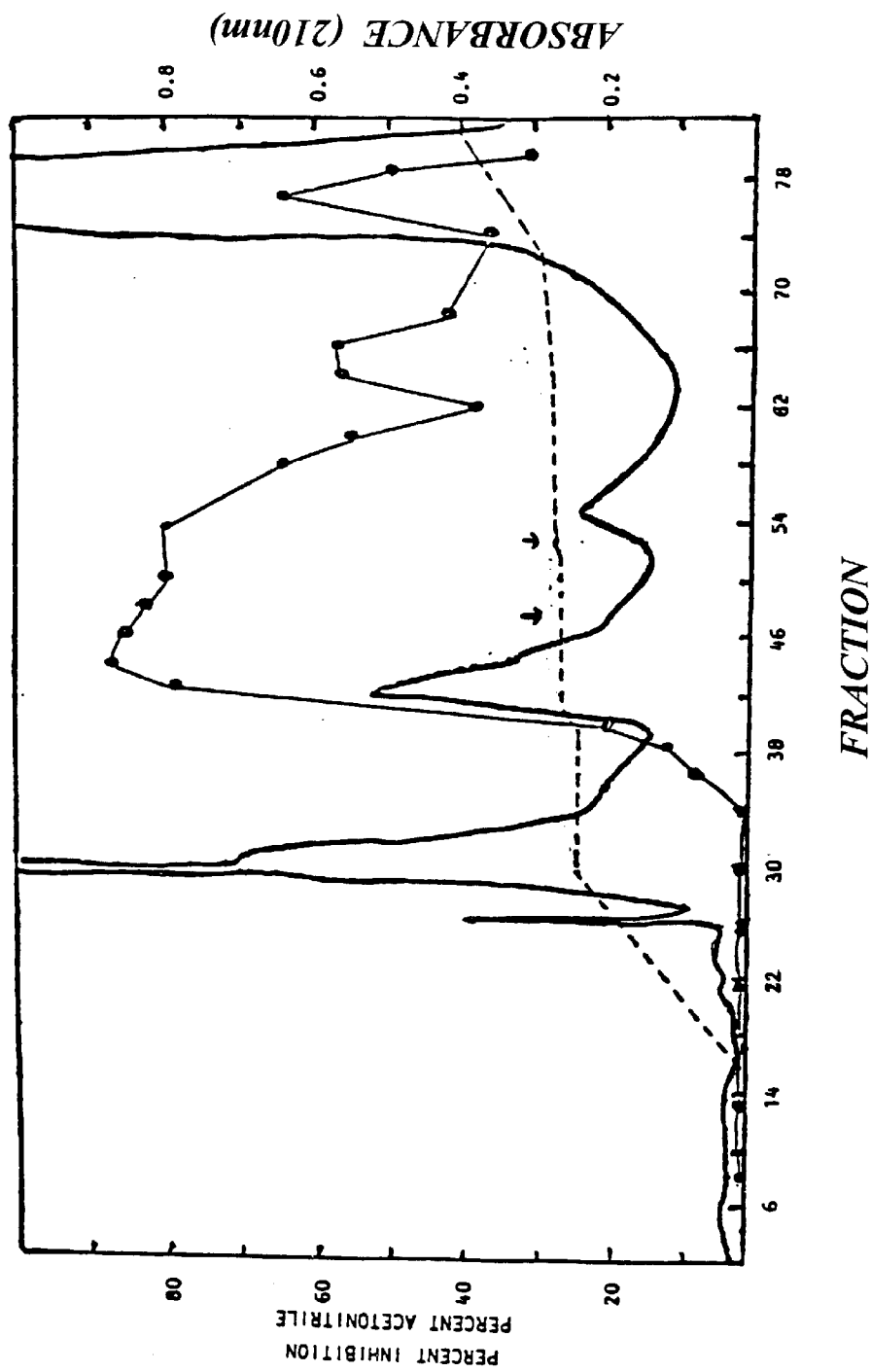

FIG. 29A. Reverse Phase High Pressure Liquid Chromatography (HPLC) (Microbondapak® C18)

One mg of lyophilized TGI derived from the stromal component of umbilical cord tissues (dissected) obtained from the pooled biologically active fractions resulting from phenyl-Sepharose chromatography was diluted in 2.0 ml of 0.05% trifluoroacetic acid (TFA) containing 10% acetonitrile. The amount of protein used for RPHPLC at this step represents 50% of the total biologically active proteins obtained following chromatography using phenyl Sepharose. The protein solution was sonicated for two minutes (Branson B-220 Sonicator) and particulate matter removed by centrifugation (Beckman Model TJ6) at 3,000 rpm for 5 minutes prior to injection into a Microbondapak® C18 column (0.39×30 cm). The protein was eluted flow rate of 1.0 ml per minute using a stepwise gradient. The concentration of acetonitrile was initially increased at 25% in fifteen minutes elution was continued at 25% for 10 minutes; the concentration was then increased to 27% in two minutes and elution was continued at 27% for ten minutes; then concentration increased to 28% in 2 minutes continued at 28% for 10 minutes, and finally the concentration was to 100% in 10 minutes. The fractions were collected into silienized glass tubes. The solvent gradient is illustrated by short dashes. Absorbance of protein was monitored at 210 nm (z,900). Each fraction volume contained 1.0 ml. The equipment used for RPHPLC was exactly as described in FIG. 12. Five microliter aliquots from every other tube were removed to assess tumor growth inhibitory activity against CCL 64 and A549 as previously described. Activity against the CCL 64 cell line is indicated by closed circles (●—●—●). Fractions 47–51 were pooled separately for electrophoresis by SDS-PAGE® (marked by arrows). 350,000 inhibitory units were applied in this chromagtographic procedure and the recovered units in the pooled fractions were: 150,000 in fractions 39–58; 14,850 in fractions 59–71 (Total 159,450). The growth inhibitory activity eluted at 27% and 28–30% acetonitrile.

Figure 29B:
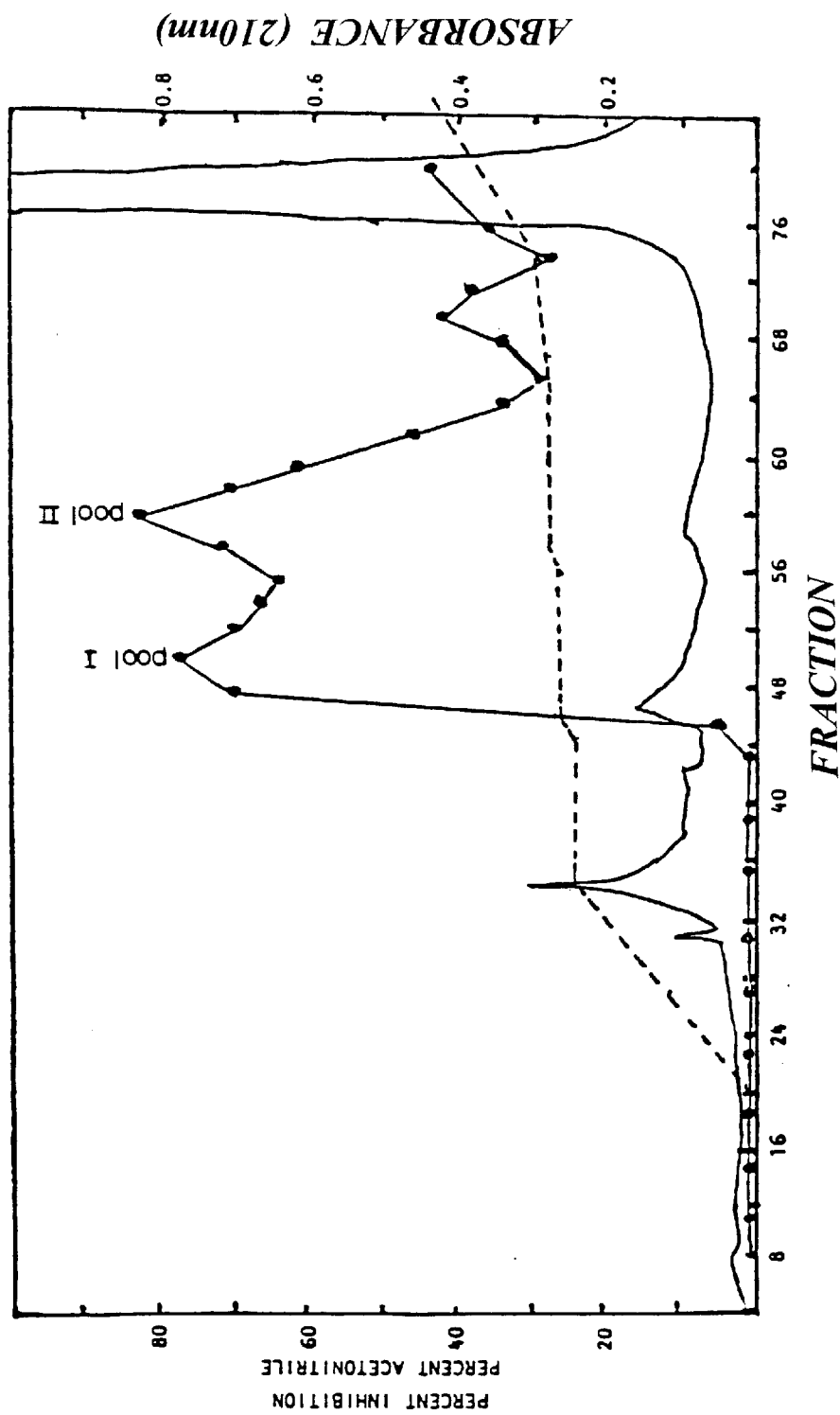

FIG. 29B. Reverse High Pressure Liquid Chromatography (HPLC) (Microbondapak C18)

Three hundred forty-five micrograms of TGI derived from the stromal component of umbilical cord tissues dissected, obtained from pooled biologically active fractions resulting from phenyl-Sepharose chromatography were diluted in 2.0 ml of 0.05% trifuoracetic acid (TFA) and 10% acetonitrile. The protein was prepared and chromatographed exactly as described in FIG. 29A. Ten microliters from each 1.0 ml sample was used to test for inhibitory activity. This sample represented 30% of the total biologically active pooled fractions derived from phenyl-Sepharose chromatography. The number of inhibitory units applied to the column was 312,500. The recovered units were 62,500 infractions 46–50, and 51–55, 50,000 units, and 90,000 units in fractions 56–72 (Total 202,500 units recovered).

FIG. 30. Sodium Dodecyl Sulfate Polyacrylamide Slab Gel Electrophoresis (SDS-PAGE)

The lyophilized pool of biologically active protein, as marked by arrows, in FIG. 16A from chromatography by Microbondapak® C18 from two identical chromatographic procedures were pooled and prepared for gel electrophoresis. Samples were diluted in 100 microliter sample buffer containing 0.1 M Tris HCl, pH 6.8 (Sigma), 15% glycerol (Kodak), and 2% sodium dodecyl sulfate (SDS). The samples were boiled for two minutes to remove protein which may have adhered to the glass (silicosized) and 50 microliters transferred to 50 microliters of sample buffer containing 10% S-mercaptoethanol (BioRad®) for reduction of disulfide bonds. These samples were boiled for 2 minutes and both the unreduced and reduced samples were applied to two separate 1.5 mm wide slab gels (marked as lane 1) and electrophoresed through a 10–20% acrylamide gradient in a vertical electrophoresis cell (BioRad, Model 155) under constant current at 30 milliamps (ma) per gel for 4.5 hours (Hoeffer power supply PS 1200 DC). Molecular weight standards (Pharmacia) both reduced by 5% β-mercaptoethanol and non-reduced are marked with their corresponding molecular weights. They are as follows, phosphorylase A, 96kDa; bovine serum albumin, 68 kDa; ovalbumin, 43 kDa; carbonic anhydrase, 30 kDa; soybean trypsin inhibitor, 21 kDa; and lysozyme 14.4 kDa. Fifty nanograms (50 ng) of a purified platelet derived TGF-β supplied by Dr. Bruce Magun was diluted in sample buffer and electrophoresed under non-reducing conditions (a) and reducing conditions(b) shown in lane 2. The gels were stained with 0.125% Coomassie Blue R-250 (BioRad) in 5.7% acetic acid 47% methanol for ten minutes (to fix the protein in the gel), and destained overnight in the same solution without Coomassie Blue. The gels were restained by a silver technique as described by Merril (BioRad silver staining kit #161-0443) Lane 1 (TGF- ) contains approximately 1,000–1,500 (50 ng) units of growth inhibitory activity, and lane 2 contains approximately 8,000–20,000 units of growth inhibitory activity.

Figure 31:
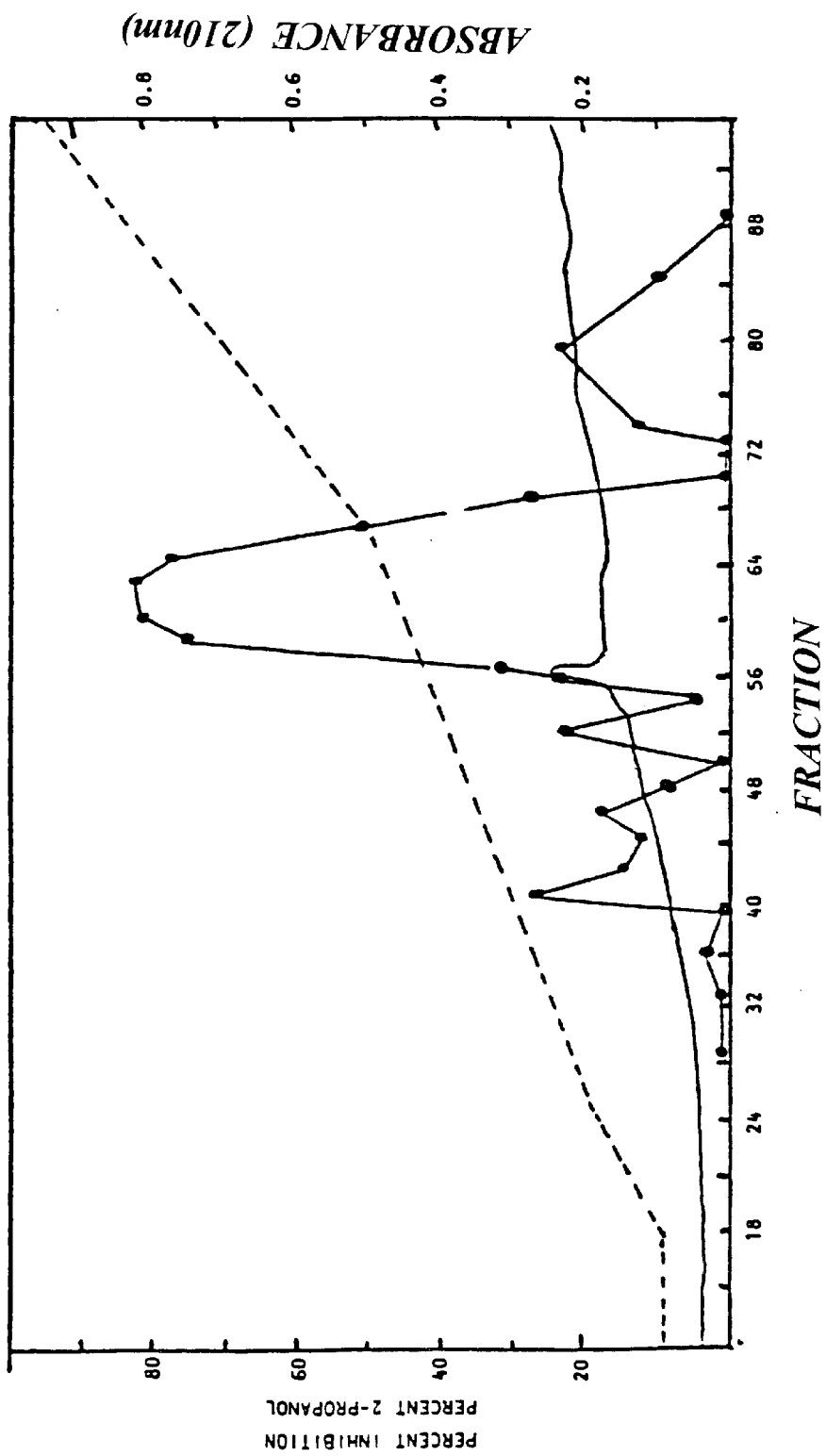

FIG. 31. Reverse Phase High Pressure Liquid Chromatography (HPOLC) (Microbondapak® CN)

Active fractions from the previous HPLC procedure (14B) were combined from two separate chromatographic runs. The lyophilized material from individual tubes (siliconized glass 13×10 mm tubes) was suspended in 4.0 ml of 0.1% trifluoracetic acid (TFA) containing 10% propanol, sonicated for two minutes and injected onto a Microbondapak® CN column (0.39×30 cm) at 1.0 ml/minute. Elution of the protein was achieved by increasing the concentration of 2-propanol containing 0.05% trifluoracetic acid (TFA) from 10% to 20% in 10 minutes, the concentraction was then increased to 20–50% in 50 minutes (0.6% per minute), and finally the concentration was increased to 100% in twenty minutes. The solvent gradient is shown as short dashes. Absorbance of the eluted protein was monitored at 210 nm (_____). The equipment used for RPHPLC was exactly as described in FIG. 12. Each fraction volume was 1.0 ml and an aliquot of two hundred microliters was then removed from every other tube to assess biological activity (closed circles). The inhibitory activity eluted from the column between approximately 40–45% 2-propanol. Twelve thousand units (12,000) of activity were applied to this column. The following fractions were lyophilized, iodinated and electrophoresed by SDS-PAGE. The total number of units contained in these fractions were: Fraction 56 (0 units), #58 (488 units), 59–65 (11,750 units), and 66–68 (185 units).

Figure 32:
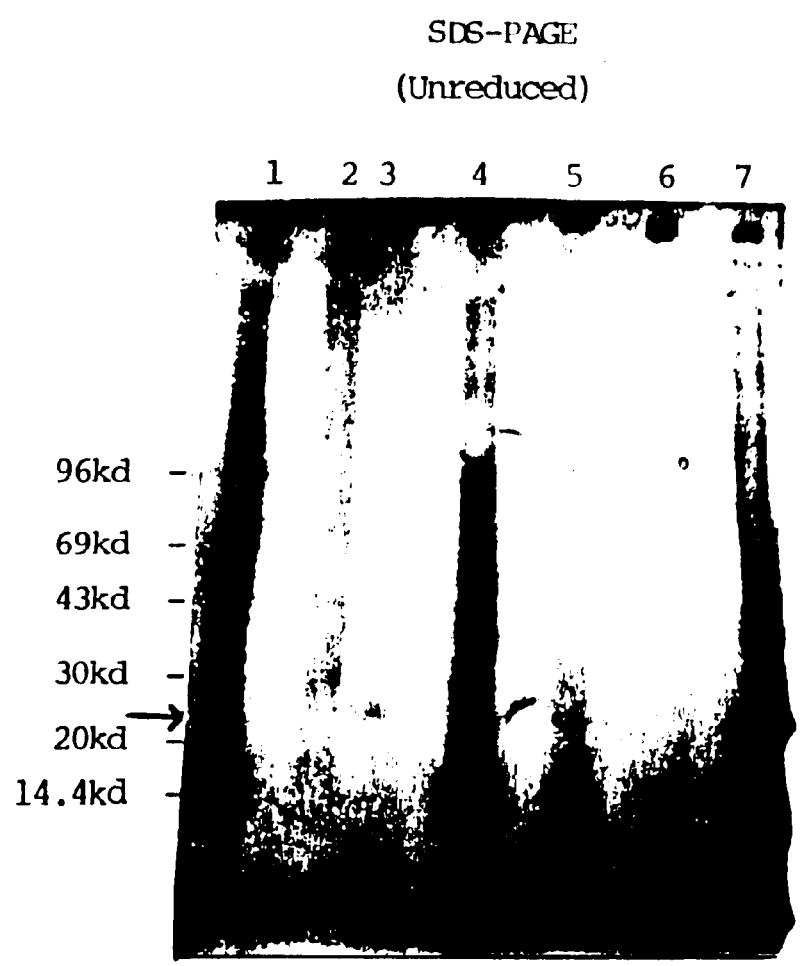

FIG. 32. SDS Polyacrylamide Slab Gel Electrophoresis and Autoradiography

Lyophilized samples from specific active and inactive fractions from chromatography on a Microbondapak® CN column illustrated in FIG. 16 were iodinated as described in text. Samples were dissolved in both non-reducing and reducing sample buffer as described for FIG. 15 and electrophoresed using a 5–20% acrylamide gradient to resolve protein bands and were also removed of free-radioactive iodine. The gels were stained and destained until the radioactive label disappeared from the destain solution. The gels were dried using a gel dryer (Hoeffer) and subjected to autoradiography using type XAR film (Kodak) for 1 week. Non-radioactive standards were also electrophoresed and are marked at the left of the gel. The number of calculated inhibitory units applied to this gel were: From FIG. 16, fraction #58 (189 units), lane 1, #59–65 (2,068 units), lane 2; #66–68 (46 units), lane 3; #56 (0 units), lane 4; active fraction of undissected human umbilical cord following chromatography on a Microbondapak® CN column as described in FIG. 18 chromatogram (not shown), (408 units), lane 5; inactive fractions from same stromal/vascular preparation, lane 6; platelet-derived TGF-β purified by Bruce Magun (256 units, approximately 0.4 ng), lane 7.

Figure 33:
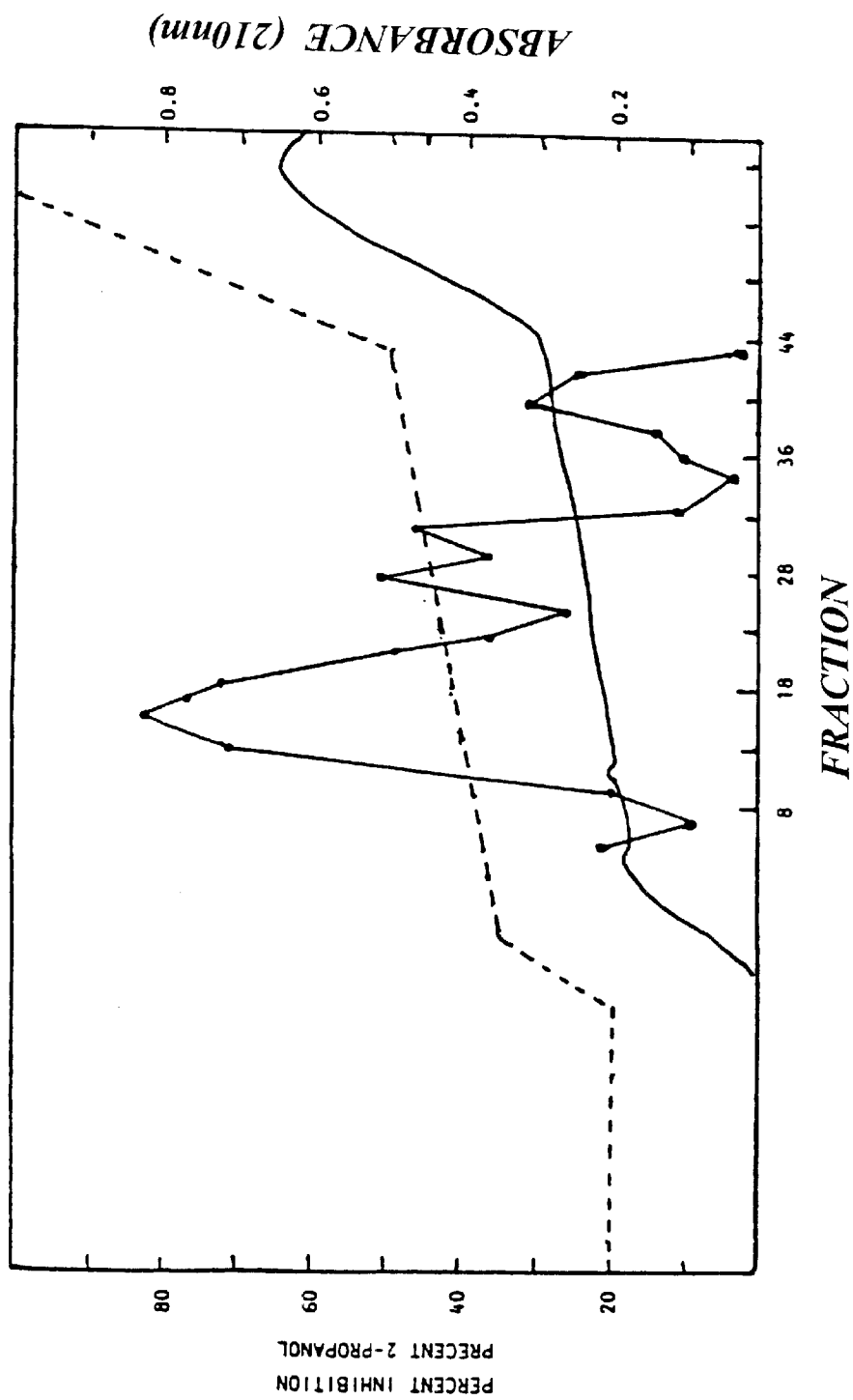

FIG. 33. Reverse Phase High Pressure Liquid Chromatography (HPLC) (Microbondapak® CN)

Active fractions from a previous HPLC procedure of undissected umbilical cord (similar to FIGS. 14A & 14B), which eluted at 27% acetonitrile (Pool I) from a Microbondapak® C18 column were pooled, lyophilized to 1.0 ml volume in a siliconized glass tube (16×100 mm) and diluted to a final concentration of 0.1% trifluoracetic acid (TFA) and 20% 2-propanol. The sample was sonicated for 2 minutes and injected onto a Microbondapak® CN column (0.39×30 cm) at 1 ml per minute. Elution of the protein was achieved by increasing the concentration of 2-propanol containing 0.1% TFA from 20% to 35% in 5 minutes followed by 35 to 50% in 50 minutes (0.375% per minute), and 50% to 100% in 5 minutes. The solvent gradient is shown as short dashes. An aliquot of 10 microliters was removed from each 1.0 ml sample to test for biological activity (closed circles). The equipment used for RPHPLC is as described in FIG. 14. The active fractions eluted between 39 to 43% with the peak of activity eluting at 40–41%. The number of calculated inhibitory units applied to the column was 37,000. Protein concentrations could not be determined.

Figure 34:
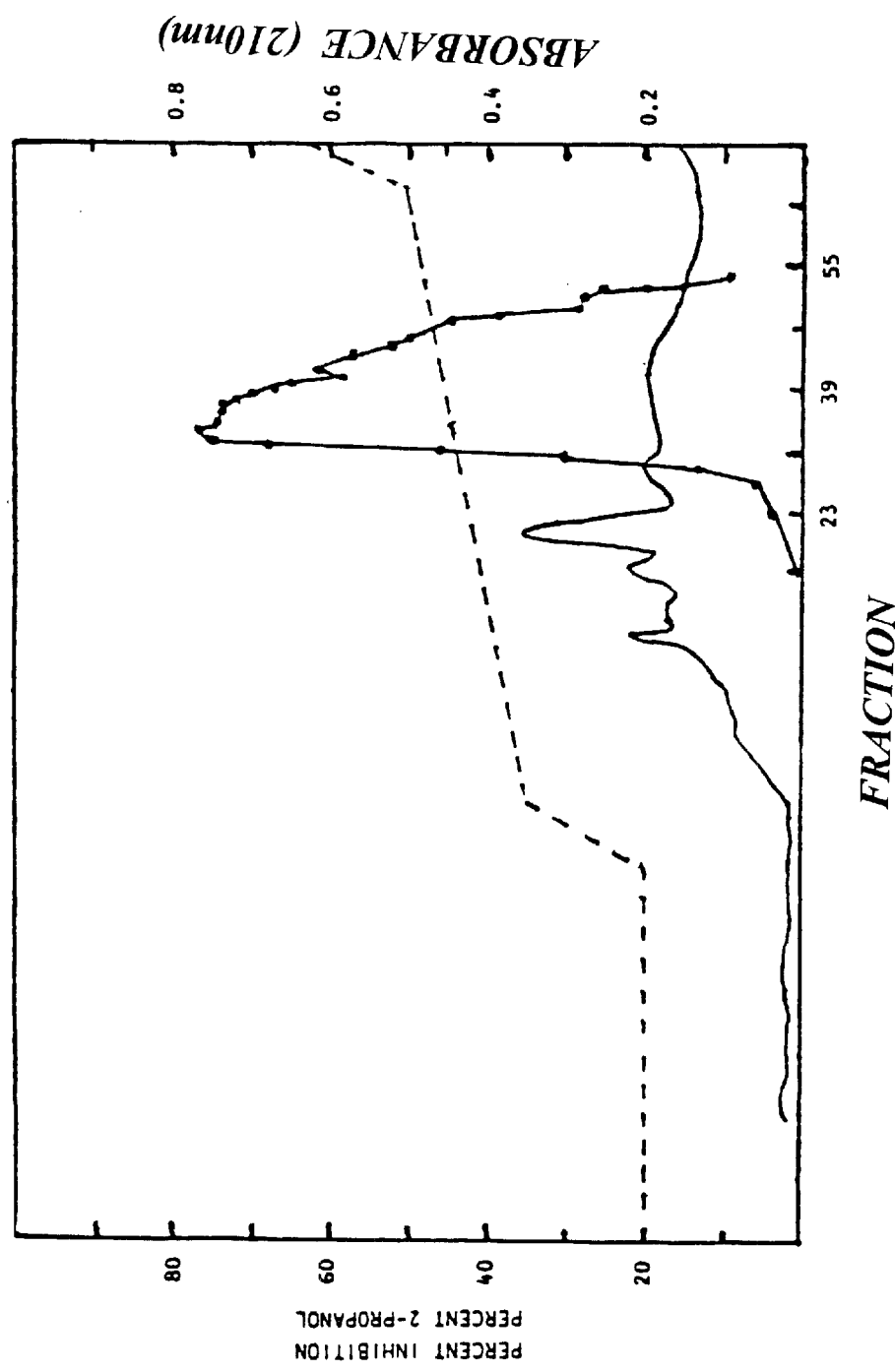

FIG. 34 Reverse Phase High Pressure Liquid Chromatographiy (HPLC) (Microbondapak® CN)

Active fractions from a previous HPLC procedure (the same chromatographic run that FIG. 18 was derived from) which eluted at 28–30% acetonitrile (Pool II) from a C18 resin polled and applied to a Microbondapak® CN column as described in FIG. 20. Gradient elution and equipment is also as described for FIG. 18.

Aliquots of 100 microliters were removed from every tube to test biological activity (closed circles). Biological activity eluted from 44% to 46% with the peak of activity at 44%. The number of growth inhibitory units applied to the column was 21,000. Protein concentration could not be determined.

Figure 35:
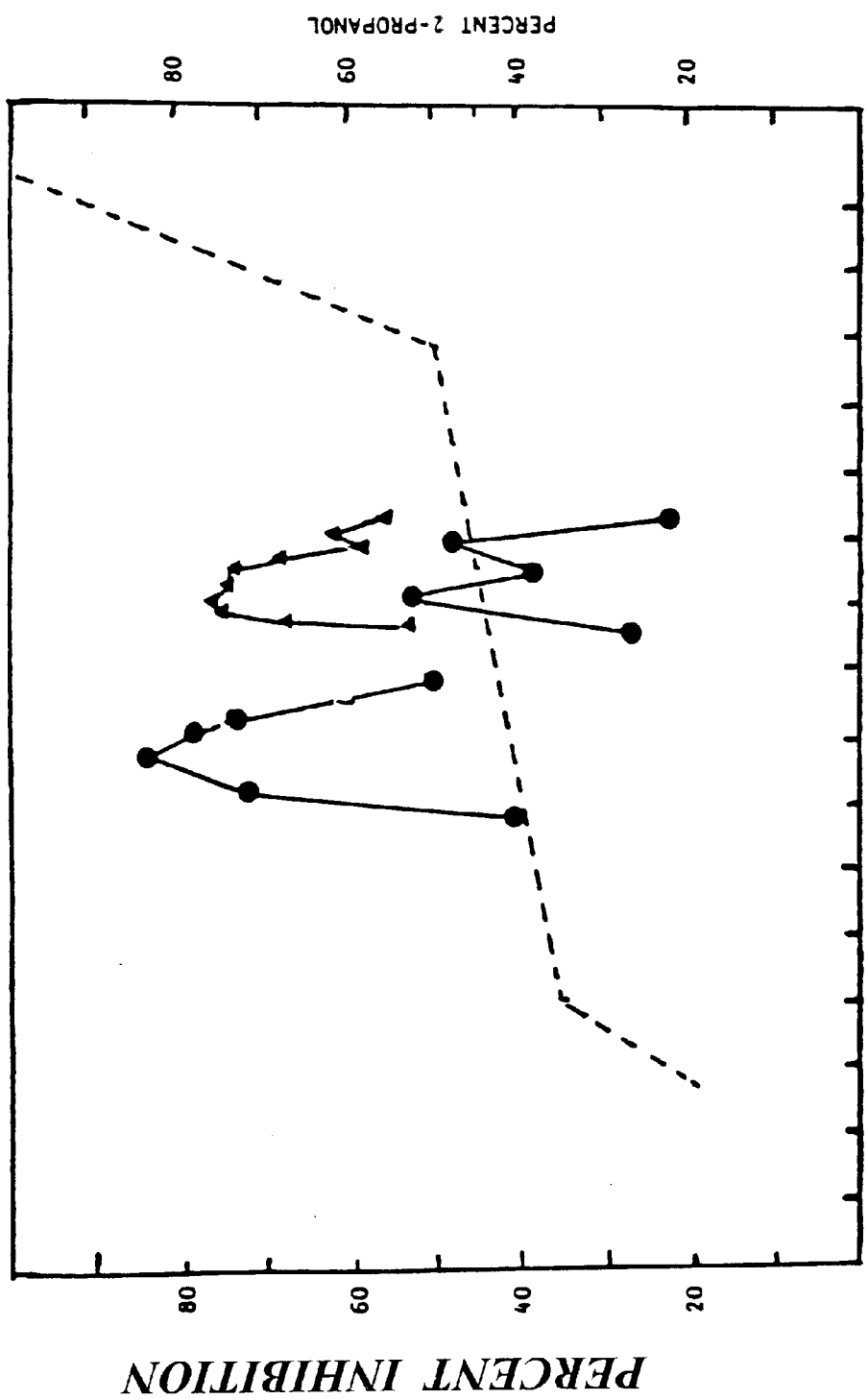

FIG. 35. Reverse Phase High Liquid Chromatography (HPLC) (Microbondapak® CN)

The elution profiles reflecting biological activity (peaks only) from FIG. 18 (Pool I) and FIG. 19 (Pool II) have been traced onto a separate chromatogram for comparison. Pool I eluted at 40–41% and Pool II at 44%.

Figure 36:
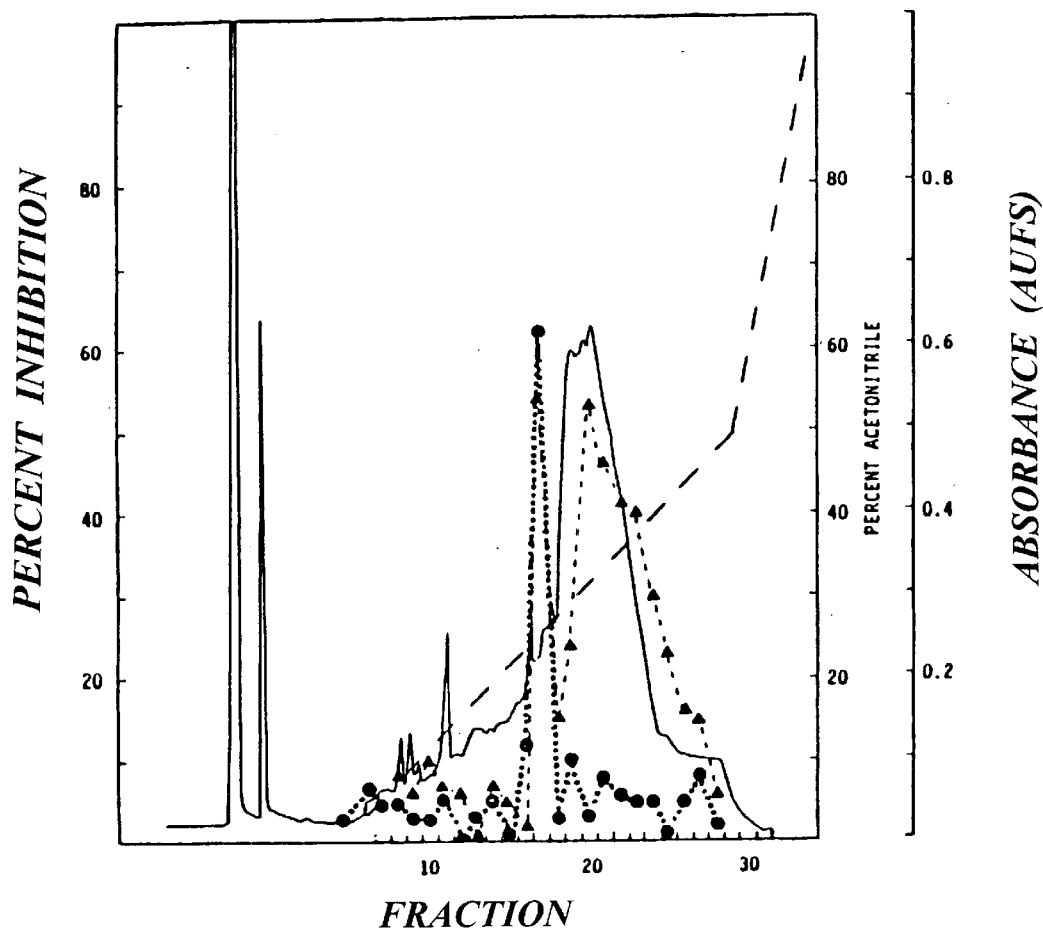

FIG. 36. Reverse Phase HPLC of A431 Conditioned Media

Lyophilized conditioned media from 4×10⁸ A431 cells (110 ml) was processed, as previously described, for the effect of dithiothreitol on tumor growth inhibitory activity derived from tumor cell conditioned media. Lyophilized conditioned media from A431 cells was resuspended in 5 ml 4 mM HCl and centrifuged to remove insoluble material (RC5B-Sorvall® SA600 rotor) for 15 minutes at 3,5000 RPM at 4° C. The supernatant was transferred to 1.5 ml microfuge tubes an centrifuged in an Eppendorf® microfuge for 15 min at 4° C. Protein concentration was determined by absorbance at 280 nm. An aliquot of 0.2 ml containing 680 micrograms protein was added to 1.8 ml 0.1 M ammonium bicarbonate. The samples were incubated at room temperature for 2 hours, lyophilized, and resuspended in 2 ml of 0.05% trifuoracetic acid. The material was injected onto a reverse phase semipreparative Microbondapak® C18 column at 1.0 ml/min, 2.0 ml and fractions were collected at the start of acetonitrile from 0–50% in 50 min. An aliquot of 1.0 ml from each fraction was assayed for tumor growth inhibitory activity against mink cell line (CCL 64) and hyman tumor cell line (A549) as previously described.

Figure 37:
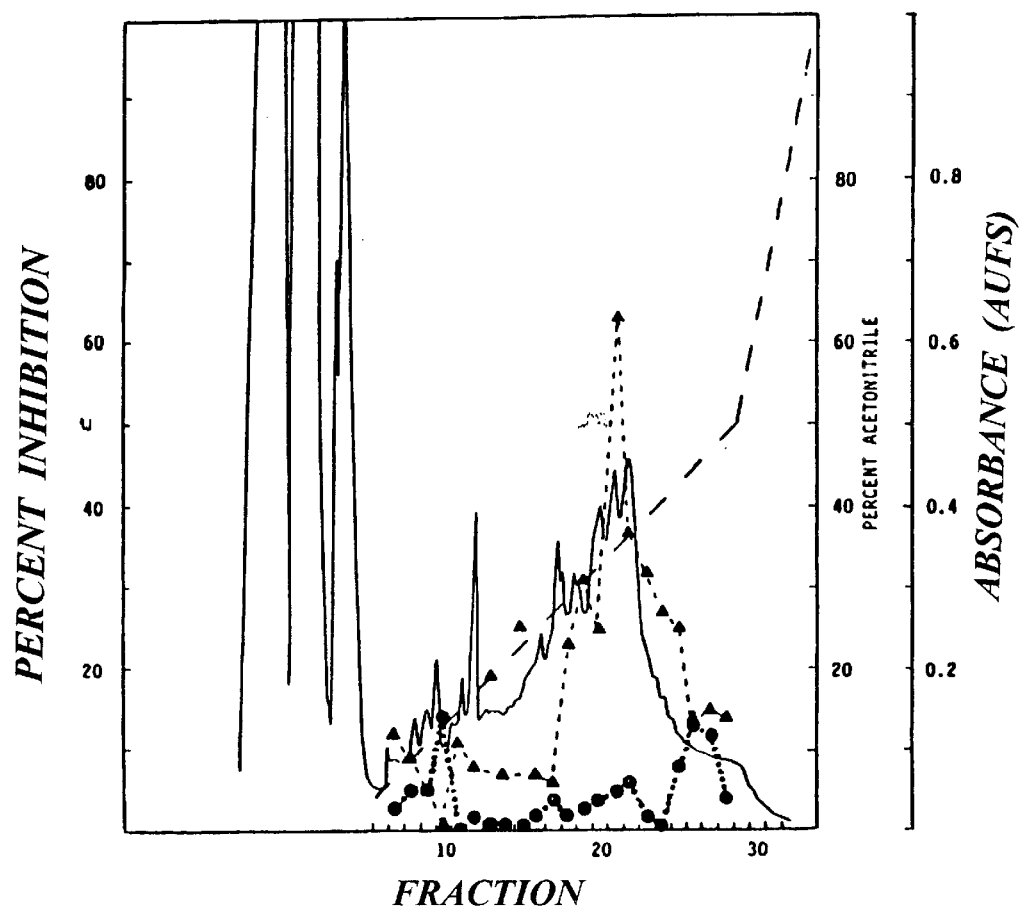

FIG. 37. Reverse-phase HPLC of A431 Conditioned Media Treated with DTT

Lyophilized conditioned media from 4×10⁸ A431 cells (110 ml) was processed, as previously described, for the effect of dithiothreitrol on tumor growth inhibitory activity in tumor cell conditioned media. Lyophilized conditioned media from A431 cells was resuspended in 5 ml 4 mM HCl and centrifuged to removed insoluble material (RC5B-Sorvall® SA 600 rotor) for 15 minutes at 3,500 RPM at 4° C. The supernatant was transferred to 1.5 ml microfuge tubes and centrifuged in an Eppendorf® microfuge for 15 min. at 4° C. Protein concentration was determined by absorbance at 280 nm. An aliquot of 0.2 ml containing 680 micrograms protein was added to 1.8 ml 0.1 M ammonium bicarbonate containing a final concentration of 65 nM DTT. The samples were incubated at room temperature for 2 h., lyophilized, and resuspended in 2 ml of 0.05% trifuoracetic acid. The material was injected onto a reverse phase semi-preparative Microbondapak® C18 column at 1.0 ml, and 2.0 ml fractions were collected at the start of a linear gradient and assayed for growth inhibitory activity against mink lung cell line (CCL 64) and humn tumor cell line (A549) as previously described.

DETAILED DESCRIPTION OF THE INVENTION

This invention is directed to a chromatographically recovered polypeptide having the N-terminal amino acid sequence Ala-Leu-Asp-Thr-Asn-Tyr-Cys-Phe-Arg-Asn-Leu-Glu-Glu-Asn-Cys-Cys-Val. This polypeptide is known as TGI, TGI-1 and TGI-2. It is also referred to as TGF-β3. The invention is also directed to a compositions which comprises the chromatographically recovered polypeptide. The invention also provides a pharmaceutical compositions to inhibit the growth of epithelial cells or heal a wound or treat a burn consisting of the chromatographically recovered polypeptide. The invention is also directed to methods which comprise administering to a subject an effective amount of the chromatographically recovered so as to thereby inhibit the growth of epithelial cells, or heal the wound or treat the burn.

An acidified, ethanol extract derived from human tissue has been produced which comprises a plurality of polypeptides. Each of the polypeptides has a molecular weight less than about 20,000 daltons and each has the property of inhibiting the growth of human tumor cells and of an established mink lung cell line (CCL64) while stimulating the growth of normal human foreskin fibroblasts. The inhibitory activity against human tumor cell growth is not destroyed upon increasing the temperature of the acidified, ethanol extract to about 100° C. for about 3 minutes or upon adding acetic acid until the extract is up to about 1.0 molar in acetic acid. The inhibitory activity of the acidified, ethanol extract is enhanced when it is prepared at about 4° C. rather than about 23° C. In a preferred embodiment the human tissue is human umbilical cord, although other tissues, e.g. human placenta, may be used.

An acidified, ethanol extract derived from human umbilical cord which has been treated to remove substantially all blood, all extracellular soluble components and all intracellular soluble components has also been produced which comprises at least one acidic polypeptide. The polypeptide has an apparent molecular weight less than about 30,000 daltons under nonreducing conditions and has the property of inhibiting the growth of human tumor cells and of an established mink lung cell line (CCL64) while stimulating the growth of normal human foreskin fibroblasts. The inhibitory activity against human tumor cell growth is not destroyed upon increasing the temperature of the acidified, ethanol extract to about 100° C. for about 3 minutes or upon adding acetic acid until the acidified, ethanol extract is up to about 1.0 molar in acetic acid.

Various components of the acidified, ethanol extract may be prepared using techniques known to those skilled in the art, e.g., high performance liquid chromatography and cation exchange chromatography. Thus, a composition of matter designated tissue-derived growth inhibitor-1 (TGI-1) which comprises at least one polypeptide having the property of inhibiting the growth of human tumor cells and of an established mink lung cell line (CCL64) but not the growth of normal human foreskin fibroblasts and having an apparent molecular weight in the range from about 5,000–16,000 daltons is recoverable as a defined activity on high performance liquid chromatography of the acidified, ethanol extract with a linear gradient of acetonitrile containing 0.05% trifluroacetic acid at about 26–34% acetonitrile and is recoverable as a defined activity on high performance liquid chromatography of the acidified, ethanol extract with a linear gradient of 2-propanol containing 0.05% trifluroacetic acid at about 17–23% 2-propanol. TGI-1 is further separable into two components when eluted on high performance liquid chromatography with a linear gradient of 2-propanol containing 0.05% trifluroacetic acid into two activities, one of which elutes at about 26% 2-propanol and preferentially inhibits the growth of human tumor cells but not the growth of an established mink lung cell line (CCL64) and the other of which elutes at about 23% 2-propanol and preferentially inhibits the growth of an established mink lung cell line (CCL64) but not the growth of human tumor cells.

Another composition of matter designated tissue-derived growth inhibitor (TGI) which comprises at least one polypeptide having the property of inhibiting the growth of human tumor cells and of an established mink lung cell line (CCL64) but not the growth of normal human foreskin fibroblasts is described. TGI has an apparent molecular weight in the range from about 20,000–30,000 daltons, is recoverable as a defined activity on high performance liquid chromatography of an acidified, ethanol extract with a linear gradient of acetonitrile containing 0.05% trifluroacetic acid at about 28–34% acetonitrile and is resolved as a single peak of defined activity from a cation exchange resin, e.g., CM-TRISACRYL resin when eluted by a linear NaCl gradient at about 06.–0.7 M NaCl.

Another composition of matter designated tissue-derived growth inhibitor-2 (TGI-2) which comprises at least one polypeptide having the property of inhibiting the growth of human tumor cells and of an established mink lung cell line (CCL64) but not the growth of normal human foreskin fibroblasts and having an apparent molecular weight in the range from about 5,000–16,000 daltons is recoverable as a defined activity on high performance liquid chromatography of an acidified, ethanol extract with a linear gradient of acetonitrile containing 0.05% trifluroacetic acid at about 35–39% acetonitrile and is recoverable as a defined activity on high performance liquid chromatography of an acidified, ethanol extract with a linear gradient of 2-propanol containing 0.05% trifluroacetic acid at about 23–27% 2-propanol.

Additionally, a heterogeneous population of polypeptides designated CM-I, CM-II, CM-III and CM-IV, each of which has the property of inhibiting the growth of human tumor cells, all of which except CM-I have the property of substantially inhibiting the growth of an established mink lung cell line (CCL64) and none of which inhibits the growth of normal human foreskin fibroblasts, is recoverable by cation exchange chromatography of the acidified, ethanol extract.

TGI-1, TGI, TGI-2 or the heterogeneous population of polypeptides designated CM-I, CM-II, CM-II and CM-IV or various combinations thereof, may be used in pharmaceutical compositions which comprise an effective amount of TGI-1, TGI, TGI-2 or the heterogeneous population of polypeptides designated CM-I, CM-II, CM-III and CM-IV together with a suitable pharmaceutical carrier. Effective amounts may vary among the various tumor growth inhibitors depending on the indication to be treated, the patient or the stage of tumor development, by methods well known to those skilled in the art. Similarly, suitable carriers such as saline or other aqueous solutions, gels, creams and the like are well known to those skilled in the art.

TGI-1, TGI, TGI-2 or the heterogeneous population of polypeptides designated CM-I, CM-II, CM-II and CM-IV may be used to inhibit the growth of human tumor cells, e.g., carcinoma, melanoma or leukemia cells, by contacting the cells with an effective growth inhibiting amount of TGI-1, TGI, TGI-2 or the heterogeneous population of polypeptides designated CM-I, CM-II, CM-II and CM-IV. TGI-1, TGI, TGI-2 or the heterogeneous population of polypeptides designed CM-I, CM-II, CM-II and CM-IV may also be used to treat burns or to facilitate the healing of wounds by contacting the burn or wound with a pharmaceutical composition which includes an effective amount of TGI-1, TGI, TGI-2 or the heterogeneous population of polypeptides designated CM-I, CM-II, CM-II and CM-IV and a suitable pharmaceutical carrier.

A method is disclosed for preparing the acidified, ethanol extract from human tissue, the acidified, ethanol extract comprising a plurality of polypeptides, each of which has a molecular weight less than about 20,000 daltons and each has the property of inhibiting the growth of human tumor cells and of an established mink lung cell line (CCL64) while stimulating the growth of normal human foreskin fibroblasts, the method comprising under suitable conditions treating the tissue e.g., by freeze-thawing or homogenization of the tissue, to produce lysed cells and solubilized proteins derived from the cells, recovering the solubilized proteins, separately recovering from the solubilized proteins polypeptides having an apparent molecular weight less than about 20,000 daltons, assaying the separately recovered polypeptides to identify those which either inhibit the growth of human tumor cells or inhibit the growth of an established mink lung cell line (CCL64) or enhance the growth of normal human foreskin fibroblasts and recovering an acidified, ethanol extract containing the polypeptides so identified.

In a presently preferred embodiment, treating the tissue comprises thawing the frozen tissue at about 4° C. for a suitable period of time, e.g. six hours, suspended the tissue in a suitable acidic extraction buffer containing ethanol at about 4° C. and homogenizing the tissue for a suitable period of time to form homogenized tissue, stirring the homogenized tissue for a suitable period, e.g., overnight, about 4° C., to produce lysed cells and to solubilize proteins derived from the cells.

A presently preferred acidic extraction buffer comprises about 375 ml of 95% (v/v) ethanol, 7.5 ml of concentrated HCl, 33 mg. of phenylmethylsulfonyl fluoride (PMSF) and 1 ml of Aprotinin (Sigma A6012 with 9.8 Trypsin inhibitor units per ml in 0.9% NaCl and 0.9% benzyl alcohol) mixed with about 192 ml of distilled water at 4° C.

In a presently preferred embodiment, recovering the solubilized proteins comprises separating the solubilized proteins from the lysed cells, e.g., by centrifugation, raising the pH to about 5.0, e.g., by adding ammonium hydroxide, removing the precipitate, e.g., by centrifugation, precipitating the proteins from the supernatant, e.g., by adding alcohol, an ether, or both, removing the precipitate from the solution, e.g., by allowing the solution to stand at about 4° C. for about 48 hours and by centrifugation, removing the organic phase from the precipitate, allowing the precipitate to dry, e.g., in a fume hood, redissolving the dried precipitate in a suitable solvent, e.g., 1 M acetic acid, and removing low molecular weight solutes from the solution, e.g., by dialysis.

A method is also disclosed for preparing an acidified, ethanol extract from human umbilical cord, the acidified, ethanol extract comprising tissue-derived growth inhibitor (TGI) which has an apparent molecular weight less than about 20,000–30,000 daltons and which has the property of inhibiting the growth of human tumor cells and of an established mink lung cell line (CCL64) while stimulating the growth of normal human foreskin fibroblasts. The method comprises under suitable conditions, removing veins and arteries from the umbilical cord tissue and washing the tissue to remove all traces of blood, treating the tissue to produce lysed cells and removing the soluble proteins derived from the cells, solubilizing and isolating the remaining proteins by acidified ethanol extraction to produce solubilized proteins, separately recovering from the solubilized proteins TGI having an apparent molecular weight of about 20,000–30,000 daltons, assaying the separately recovered TGI to identify the activity which inhibits the growth of human tumor cells, inhibits the growth of an established mink lung cell line (CCL64) and enhances the growth of normal human foreskin fibroblasts, and recovering an acidified, ethanol extract containing the TGI so identified.

In a presently preferred embodiment, treating the tissue comprises thawing the frozen tissue at about 4° C. for a suitable period of time, e.g. two hours, removing the veins and arteries by dissection at about 4° C., suspending the tissue in a suitable buffer at about 4° C. and homogenizing the tissue for a suitable period of time to form lysed cells and soluble proteins, separating the soluble proteins from the lysed cells, e.g. by centrifugation and stirring the lysed cells in extraction buffer for a suitable period, e.g. overnight at about 4° C. to produce solubilized proteins.

A presently preferred acidic extraction buffer comprises about 375 ml of 95% (v/v) ethanol, 7.5 ml of concentrated HCl, 33 mg. of phenylmethylsulfonyl fluoride (PMSF) and 1 ml of Aprotinin (Sigma A6012 with 9.8 Trypsin inhibitor units per ml in 0.9% NaCl and 0.9% benzyl alcohol) mixed with about 192 ml of distilled water at 4° C.

In a presently preferred embodiment, recovering the solubilized proteins comprises separating the solubilized proteins from the lysed cells, e.g., by centrifugation, raising the pH to about 5.0, e.g., by adding ammonium hydroxide, removing the precipitate, e.g., by centrifugation, precipitating the proteins from the supernatant, e.g., by adding and alcohol, an ether, or both, removing the precipitate from the solution, e.g., by allowing the solution to stand at about 4° C. for about 48 hours and by centrifugation, removing the organic phase from the precipitate, allowing the precipitate to dry, e.g., in a fume hood, redissolving the dried precipitate in a suitable solvent, e.g., 1 M acetic acid, and removing low molecular weight solutes from the solution, e.g., by dialysis.

In a presently preferred embodiment the separate recovery of polypeptides from the solubilized proteins comprises gel filtration chromatography of the proteins, e.g., on Bio-Gel P-10 resin.

In a presently preferred embodiment, assaying the polypeptides comprises separately contacting the human tumor cells, e.g., human lung carcinoma line (A549), or an established mink lung cell line (CCL64), or normal human foreskin fibroblasts (HuF), under suitable conditions for a suitable period of time with the polypeptides so as to identify polypeptides which inhibit to growth of the human tumor cells or inhibit the growth of an established mink lung cell line (CCL64) or which stimulate the growth of normal human foreskin fibroblasts.

A method for preparing a composition of matter designated tissue-derived growth inhibitor-1 (TGI-1) which comprises first preparing the acidified, ethanol extract and then recovering TGI-1 from the acidified, ethanol extract as a defined activity by high performance liquid chromatography, e.g., reverse phase HPLC of the acidified, ethanol extract with either i) a linear gradient of acetonitrile containing 0.05% trifluroacetic acid at about 26–34% acetonitrile or ii) a linear gradient of 2-propanol containing 0.05% trifluroacetic acid at about 17–23% 2-propanol.

A method for preparing a composition of matter designated tissue-derived growth inhibitor (TGI) which comprises first preparing the acidified, ethanol extract and then recovering TGI from the acidified, ethanol extract as a defined activity by high performance liquid chromatography, e.g., reverse phase HPLC of the acidified, ethanol extract with a linear gradient of acetonitrile containing 0.05% trifluroacetic acid at about 28–34% acetonitrile, or as a single peak of activity from a cation exchange resin, e.g., CM-TRISACRYL resin when eluted with a linear NaCl gradient at about 0.6–0.7 M NaCl.

A method for preparing a composition of matter designated tissue-derived growth inhibitor-2 (TGI-2) which comprises first preparing the acidified, ethanol extract and then recovering TGI-2 from the acidified, ethanol extract as a defined activity by high performance liquid chromatography, e.g., reverse phase HPLC of the acidified, ethanol extract with either i) a linear gradient of acetonitrile containing 0.05% trifluroacetic acid at about 35–39% acetonitrile or ii) a linear gradient of 2-propanol containing 0.05% trifluroacetic acid at about 23–27% 2-propanol.

A method of preparing a heterogeneous population of polypeptides designated CM-I, CM-II, CM-III and CM-IV which comprises first preparing the acidified, ethanol extract and then recovering the heterogenous population of polypeptides from the acidified, ethanol extract by ion exchange chromatography, e.g. cation exchange chromatography.

A method for detecting the presence of a tumor is disclosed. The method comprises quantitatively determining the amount of TGI-1, TGI or TGI-2, or of the heterogeneous population of polypeptides designated CM-I, CM-II, CM-III or CM-IV present in a sample, e.g., blood, amniotic fluid, peritoneal fluid, ascites fluid, cerebrospinal fluid or urine, from a subject and comparing the amount so determined with the amount present in a sample from a normal subject, the pressure of a significantly different amount, e.g. a significantly higher amount, indicating the presence of a tumor.

Another method for detecting the presence of a tumor is disclosed. The method comprises separately quantitatively determining both the amount of TGI-1, TGI or TGI-2, or of the heterogeneous population of polypeptides designated CM-I, CM-II, CM-III or CM-IV and of transforming growth factor alpha (TGF-alpha) present in a sample from a subject, determining the ratio of the amount of TGI-1, TGI or TGI-2, or the heterogenous population of polypeptides designated CM-I, CM-II, CM-III, and CM-IV present in the sample to the amount of TGF-alpha present in the sample from a subject, determining the comparable ratio for a sample from a normal subject and comparing the ratio for the sample from the subject to the ratio for the sample from the normal subject, a significant variation in the ratio indicating the presence of a tumor.

A method for typing tumors is disclosed which comprises determining for a sample from a subject with a tumor the presence of one or more of TGI-1, TGI, TGI-2, or the heterogeneous population of polypeptides designated CM-I, CM-II, CM-III and CM-IV, the presence or absence of a specific combination thereof, e.g., TGI and CM-II or TGI-1 and TGI-2 being indicative of a specific tumor type, e.g., a melanoma or a carcinoma.

Finally, a method for typing tumors is disclosed which comprises quantitatively determining for a sample from a subject with a tumor the amount of each of TGI-1, TIF, TGI-2 or the heterogeneous population of polypeptides designated CM-I, CM-II, CM-III and CM-IV present in the sample, the presence of specific amounts or relative amounts thereof, e.g., a significant increase in the amount of TGI or a significant variation in a ratio such as the ratio of TGI-1 to CM-II.

EXPERIMENTAL DETAILS
First Series of Experiments
Materials and Methods

Under First Series of Experiments, "TGI activity" refers to the activity of TGI-1, TGI-2, CM-I, CM-II, CM-III and CM-IV unless otherwise noted.

Isolation of Tissue-Derived Tumor Growth Inhibitors (TGIs) From Tissue Extracts

Human umbilical cord or placenta tissues were extracted using a modification of the acid/ethanol extraction procedure described by Davoren et al. (Biochem. Biophys. Acta. 63:150 (1962) and Roberts et al., Proc. Natl. Acad. Sci. USA 77:3494 (1980).

The buffer for extraction consisted of 375 ml of 95% (v/v) ethanol (punctilious, 190 proof, U.S. Industrial Chemicals, #UN1170), 7.5 of concentrated HCl, 33 mg of phenylmethylsulfonyl fluoride (PMSF) (Sigma P-7627) and 1 ml of Aprotinin (Sigma A6012 with 19.8 Trypsin inhibitor units per ml in 0.9% NaCl and 0.9% benzyl alcohol) mixed with 192 of distilled water at 4° C. Four hundred to six hundred grams of frozen human umbilical cords or placentas (Advanced Biotechnologies) (stored at −80° C.) were thawed at 4° C. for six hours. The thawed tissue was placed in a 4° C. chilled Cuisinart food processor (Model DLC-7-PRO) and suspended in 200 ml of 4° C. extraction buffer. The suspended tissue was homogenized by food processor. After the first minute of homogenization, the suspension became creamy white. Another 200 ml of 4° C. extraction buffer was added to this white suspension. The suspension changed to a dark coffee brown color. The tissue suspension was homogenized for a total of 10 min. at 4° C. Extraction buffer was added to this homogenized tissue mixture to a final volume of 6 ml per gram of tissue homogenate.

The homogenized tissue suspension was transferred to a large 4 liter beaker with a 3 inch stir bar and stirred at half of the maximum stirring capacity of a Lab-line Multimagnestir multi-mixer, Model #1278. After overnight extraction with stirring at 4° C., the homogenate was transferred to 1 liter centrifuge bottles (Sorvall) and centrifuged at 3500 rpm (RCF=350) for 30 minutes at 4° C. in a Sorvall RC-3B centrifuge equipped with a Sorvall H-6000A rotor. The supernatant was transferred to a large 4 liter beaker and adjusted to pH 5.0 with the slow addition of concentrated ammonium hydroxide. With increasing pH, the color of the supernatant changed from brown to an orange solution. The solution was precipitated following the addition of 2.0 M ammonium acetate, pH 5.2, added at an amount of 1% of the total volume. This precipitate was removed following centrifugation at 4500 rpm (RCF=5900) for 4 hours in a Sorvall RC-3B at 4° C. The supernatant was transferred to large 6 liter flasks to which four volumes of anhydrous ether (−20° C.) (Baker 9244-3) and two volumes of 95% ethanol (4° C.) were added. The mixture was allowed to stand undisturbed at −20° C. for 48 hours to allow the resulting precipitate to settle.

At the end of the 48 hr precipitation, the etherized material was brought to ambient temperature in a fume hood. Warming of the acidified, ethanol extract to ambient temperature enhances the aggregation of the precipitate. The clear organic phase of ether and ethanol was removed by a water aspirator and the precipitate was left in the fume hood for several hours to allow the residual organic phase to evaporate. The "dried" precipitate was dissolved in 1.0 M acetic acid and dialyzed extensively against 1.0 M acetic acid (Baker #9507-5) using dialysis membranes with a molecular cutoff of 3500 (Spectropor 3, Spectrum Medical Industries, Los Angeles, Calif.). The dialyzed acidified ethanol extract was lyophilized in 250 ml Corning conical centrifuge tubes (Corning 25350) and stored as crude acidified, ethanol extract.

An alternative procedure for precipitating TGIs from the acidified, ethanol extract replaces the addition of four volumes of ether and two of ethanol with the addition of only the two volumes of ethanol at 4° C. The advantage of eliminating ether from the acidified, ethanol extract precipitation step was the elimination of a step requiring the use of a highly flammable solvent which makes the procedure and any scale-up of the processing of large amounts of materials difficult.

Gel Filtration Chromatography

Lyophilized crude acidified, ethanol extract was resuspended in 1.0 M acetic acid (10–30 mg/ml) and clarified by centrifugation at 3500 rpm for 30 min at 4° C. in a Sorvall RC-3B centrifuge equipped with a Sorvall H-6000A rotor before sample application to the column. Sample volumes of one hundred to 150 ml were chromatographed on Bio-Gel P-10, 100–200 mesh (Bio-Rad; 150–1040) in 1.0 M acetic acid at either 23° or 4° C.

The column (14×100 cm) (Amicon; #86012) contained 13.8 liters of equilibrated and degassed Bio-Gel P-10 in 1.0 M acetic acid at either 23° C. or 4° C. The void volume was determined by the addition of 50 ml of blue dextran (Sigma #D5751) at 2 mg/ml in 1.0 M acetic acid. After calibration, the column was "conditioned" with 100 ml of bovine serum albumin (Sigma #A-4503) at 100 mg/ml in 1.0 M acetic acid followed by extensive washing with 1.0 M acetic acid.

Following sample application, 1 liter fractions were collected using a SuperRac (LKB 2211) equipped with a type C collection rack, at a flow rate of 7 ml/min into 2 liter plastic tissue culture roller bottles (Falcon; 3207). Fractions were monitored by a Uvicord S (LKB 2138) at 280 nm set at an absorbance range of 2.0 AUFS and recorded by a single channel chart recorder (LKB 2210). One ml aliquots were removed from each fraction, lyophilized and assayed for TGI activity as described. The remainder of each fraction was lyophilized in 2 liter lyophilization jars (Virtis #6503-2050) using a Virtis freeze-model 24.

High Performance Liquid Chromatography (HPLC)

Individual fractions containing TGI activity from the Bio-Gel P-10 column were lyophilized and resuspended in 1 to 10 ml of 0.05% trifluoroacetic acid (TFA) (Pierce #28901) depending upon the amount of protein in each fraction. Water used for HPLC was generated using a Milli-Q water purification system. Starting buffer in all HPLC chromatography runs consisted of Milli-Q water containing 0.05% TFA. Prior to injection, the sample was centrifuged in a Beckman tabletop centrifuge (Beckman TJ-6) at 3000 rpm for 20 min to remove insoluble material. The supernatant was injected into either a Waters uBondapak analytical $C_{18}$ column (0.39×30 cm) (Waters PN27324) or semipreparative column (0.78×30 cm) (Waters PN84176) as specified in individual experiments. A Waters automated gradient controller (Waters Model 510) was utilized for column elution monitored by a variable u.v. detectors (Waters Lambda-Max, Model 481) set at 206 nm. The solvent used for elution was either acetonitrile (Baker 9017-3) or 2-propanol (Fisher, A452) containing 0.05% TFA. Fractions were collected by a SuperRac (LKB 2211) equipped with a type B collection rack into siliconized (Pierce, Aquasil #42799) 13×100 mm or 16×100 mm test tubes. Aliquots from each collected fraction were assayed for TGI activity as described below.

Ion Exchange Chromatography

Both the lyophilized material from the acidified, ethanol and ether extractions and various lyophilized fractions derived from the Bio-Gel P-10 gel filtration chromatography were separately subjected to ion exchange chromatography. CM, SP, and DEAE-TRISACRYL (LKB) ion exchange resins were used in these procedures. The samples for chromatography were diluted to a final concentration of approximately 20 mg/ml in 1.0 M acetic acid. The samples wre dialyzed at 4° C. until both the pH and conductivity were equal to the starting (equilibration) buffer. All ion exchange chromatographic procedures were performed at 4° C.

a. Chromatography using CM- and SP-TRISACRYL ion Exchange Results

The resins, as aqueous suspensions, were suspended in an equal volume of 0.1 M ammonium acetate, pH 4.0, containing 1.0 M NaCl. The resin was allowed to equilibrate for at least 3 hours and was degassed at 4° C. Twenty ml of resin was packed into a 1.6×20 cm column (Pharmacia; #19-0362-01) and washed with 2 column volumes of 1.0 M ammonium acetate, pH 4.0, followed by 0.01 M ammonium acetate, pH 4.0. The column was washed until the effluent exactly matched the conductivity of the equilibrating buffer (i.e., 0.01 M ammonium acetate, Fisher A637), pH 4.0. The sample was applied to the resin (1 gm/20 ml resin) at a flow rate of 1 ml/min, the column was washed with equilibration buffer until the optical density leveled (e.g., approaching zero optical density) and 200 ml of an ascending molarity linear gradient (Pharmacia gradient mixer GM-1, #19-0495-01) was applied a column flow adapter of concentrations 0.01 to 1.0 M ammonium acetate, pH 4.0. In certain experiments, a second gradient was applied to the same column. This second gradient ranged from 1.0 M ammonium acetate, pH 4.0, to 50% acetonitrile in 1.0 M ammonium acetate, pH 4.0. Two ml fractions were collected in polystyrene tubes, 13×100 mm, (Columbia Diagnostics; B2564) in a SuperRac Fraction collector (LKB 2211), equipped with an A type collection rack. All column chromatography was performed with the aid of a Uvicord S with a 280 nm filter (LKB 2138) and a single channel recorder (LKB 2210). Fractions were aliquoted based upon optical density ranging from 100 µl to 1 ml, and assayed for TGI activity.

b. Chromatography using DEAE-TRISACRYL

The chromatographic resin preparation and procedure was performed exactly as described for CM- and SP-TRISACRYL chromatography, except the equilibration buffer used was 0.1 M ammonium acetate, pH 6.0, the gradient elution ranged from 0.1 M to 1.0 M ammonium acetate, pH 6.0, and the sample was equilibrated in the above mentioned equilibration buffer.

Monolayer Assay for TGI Activity

Test cells were sub-cultured on 96-well tissue culture plates (Nunc 167008) in 50 µl of Dulbecco's modified Eagle's medium (Whittaker M. A. Bioproducts 12-6143) containing 10% fetal bovine serum (Whittaker M. A. Bioproducts 14-501B), 2% L-glutamine (Whittaker, M. A. Bioproducts 17-605-A), 1% penicillin and 1% streptomycin. Human lung carcinoma cells, A549, and normal human fibroblasts (HuF) required a seeding density of $5\times10^3$ cells per well. Mink cells (ATCC: CCL64) required a seeding density of $4.5\times10^3$ cells per well.

Aliquots from column fractions to be assayed for TGI activity were transferred to sterile 12×75 mm tubes (Falcon 2058) containing 50 µl of 1 mg/ml solution of bovine serum albumin (BSA; Sigma A-6003) in 1 M acetic acid and lyophilized. Immediately prior to the assay, the lyophilized sample was resuspended in 400 µl, for each cell type tested. One hundred µl aliquots of the resuspended sample were added to wells containing test cells. Each sample was assayed in triplicate. The cells were incubated for 72 hours at 37° in a humidified 5% $CO_2$/95% air atmosphere. At the end of the incubation period, each well was pulsed with 100 µl of complete medium containing 1 µCi/ml 5-[$^{125}$I] Iodo-2'deoxyuridine ($^{125}$IUdR) (New England Nuclear; NEX-072) for 24 hours. The monolayers were washed once with wash buffer A (Dulbecco's phosphate buffered saline, with 10 mM $MgCl_2$, containing 1 mg/ml BSA, pH 6.8), fixed for 10 minutes in methanol (Fisher A452), and air dried for 15 minutes. The $^{125}$IUdR incorporated by the cells was solubilized with 200 µl of 1.0 M NaOH and the plates incubated for 20 minutes at 60° C. Solubilized $^{125}$IUdr was collected using the Titertek Supernatant Collection System (Skatron Inc., 7072). The amount of cell growth is approximated by the extent of $^{125}$IUdR incorporated into the DNA of cells in the log phase of growth. Before the assay was harvested each wall was observed using a Zeiss inverted microscope to visually note the amount of cell growth. Inhibition or stimulation of growth was expressed as a ratio of $^{125}$IUdR incorporated by test cells (e.g. human tumor cells) containing the test aliquots relative to $^{125}$IUdR incorporated by the untreated control cells. The inhibition or stimulation observed by microscopic examination of treated cells corresponded well with decreased or increased incorporation of $^{125}$IUdR respectively.

Characterization of TGI Activities a. Heat Treatment

One ml aliquots from fractions 2, 4, and 6 obtained from gel filtration chromatography on Bio-Gel P-10, were lyophilized in 12×75 mm polystyrene tubes (Falcon 2034) and resuspended in 1 ml of 1.0 M acetic acid. The samples were heated for 3 minutes in a boiling water bath, lyophilized, and assayed for TGI activity as described above.

b. Treatment with Dithiothreitol (DTT)

Three ml aliquots from fraction 2, 4, and 6 obtained from gel filtration chromatography on Bio-Gel P-10, were lyophilized in 17×125 mm polystyrene screw cap tubes (Columbia Diagnostics #2570). Treated samples received 200 μl of 0.1 M ammonium bicarbonate containing a final concentration 0.1 M DTT (Calbiochem #233-153), pH 7.4. Control samples contained 200 μl 0.1 M ammonium bicarbonate (Fisher, A643), pH 7.4. The samples were incubated for one hour at 23° C., diluted to 1 ml with 1.0 M acetic acid, and dialyzed in 18 mm dialysis membranes with molecular weight cutoff of 3,500 daltson (Spectropor 3, Spectrum Medical Industries), against four changes of 4 liters of 0.1 M acetic acid. The samples were lyophilized in 12×75 mm polystyrene tubes (Falcon #2304) and assayed for TGI activity as describe above.

SDS-Polyacrylamide Slab Gel Electrophoresis

Aliquots from samples from each chromatographic procedure were lyophilized for electrophoresis. Samples were diluted in 80 μl of sample buffer containing 0.1 M Tris-HCl (Sigma; T-1503), pH 6.8, 15% glycerol (Kodak; 114-9939), 2% sodium dodecyl sulfate (SDS) (Bio-Rad; 116-0302), and 5% 2-mercapto-ethanol (Bio-Rad; 161-0710), and electrophoresed on a 5–20% acrylamide monomer gradient essentially as described (Laemmli, U.K. (1970) Nature 227, 680–685). The samples were boiled for 2 minutes prior to application to a 1.5 mm wide slab gel in a Bio-Rad Model 155 Vertical Electrophoresis Cell (Bio-Rad 165–1420) under constant current at 30 mA per gel for 4 hours (Hoeffer power supply; PS 1200 DC) at 9° C. Constant temperature was maintained by a water bath circulator (Haake, A81). Gels were stained with 0.5% Coomassie Blue R250 (Bio-Rad #16-0400) in 5.7% acetic acid and 47% methanol overnight and destained in the same solution without stain. Specific gels demonstrating low concentrations of proteins were restrained by a silver technique as described by Merril (Merril, C. R., Goldman, D. Sedman, S. and Ebert, M. H. (1981) 211:1437–1438), (Bio-Rad silver straining kit; #161–0443).

Results

Comparison of TGI Activities from Gel Filtration chromatography on Bio-Gel P-10 at room temperature and at 4° C.

The growth inhibitory activity derived from acidified, ethanol extracts of human umbilical cords eluted by gel filtration chromatography using Bio-Gel P-10 resin with apparent molecular weights ranging from 5,000–16,000 daltons. Occasionally, another peak of activity has been observed at molecular weights ranging from 3000–5000 daltons. The molecular weight calculations are based on the elution profiles of molecular weight standards (i.e., carbonic anhydrase—29,000; RNase—14,400; insulin—6,000) chromatographed on 1 liter of resin in a column of 4×100 cm. The elution profile derived from the column and from the large 14×100 cm column were superimposable. Acidified, ethanol extracts from human placenta identically chromatographed demonstrated elution profiles very similar to the umbilical cord extracts.

Fractions 1 to 3 from the umbilical cord acidified, ethanol extract are a very intense brown color; and color gradually disappears as the fractions progress. Fortunately, although tumor cell growth inhibitory activity (TGI) eluted in fractions 1, 2, and 3 containing the highest protein concentrations, the majority of activity extends past the observed protein peaks as is clearly demonstrated in FIGS. 1 and 2. Extracts from human placental material showed a greater overlap of TGI with the major protein peaks than was observed with material from human umbilical cords (data not shown). Aliquots of identical volumes form gel filtration chromatography electrophoreses by SDS-PAGE on a 5–20% polyacrylamide gradient also illustrate that by fraction 4, considerably less protein is found than in fractions 1 to 3. In fractions 5 and 6, major protein bands of 5,600 and 14,000 band are observed and by fraction 7 very little protein remains, although inhibitory activity extends into fraction 10 as shown in FIG. 2. The obvious advantage of the majority of activity eluting in regions of less protein is that it facilitates further purification of TGIs.

Figure 1:
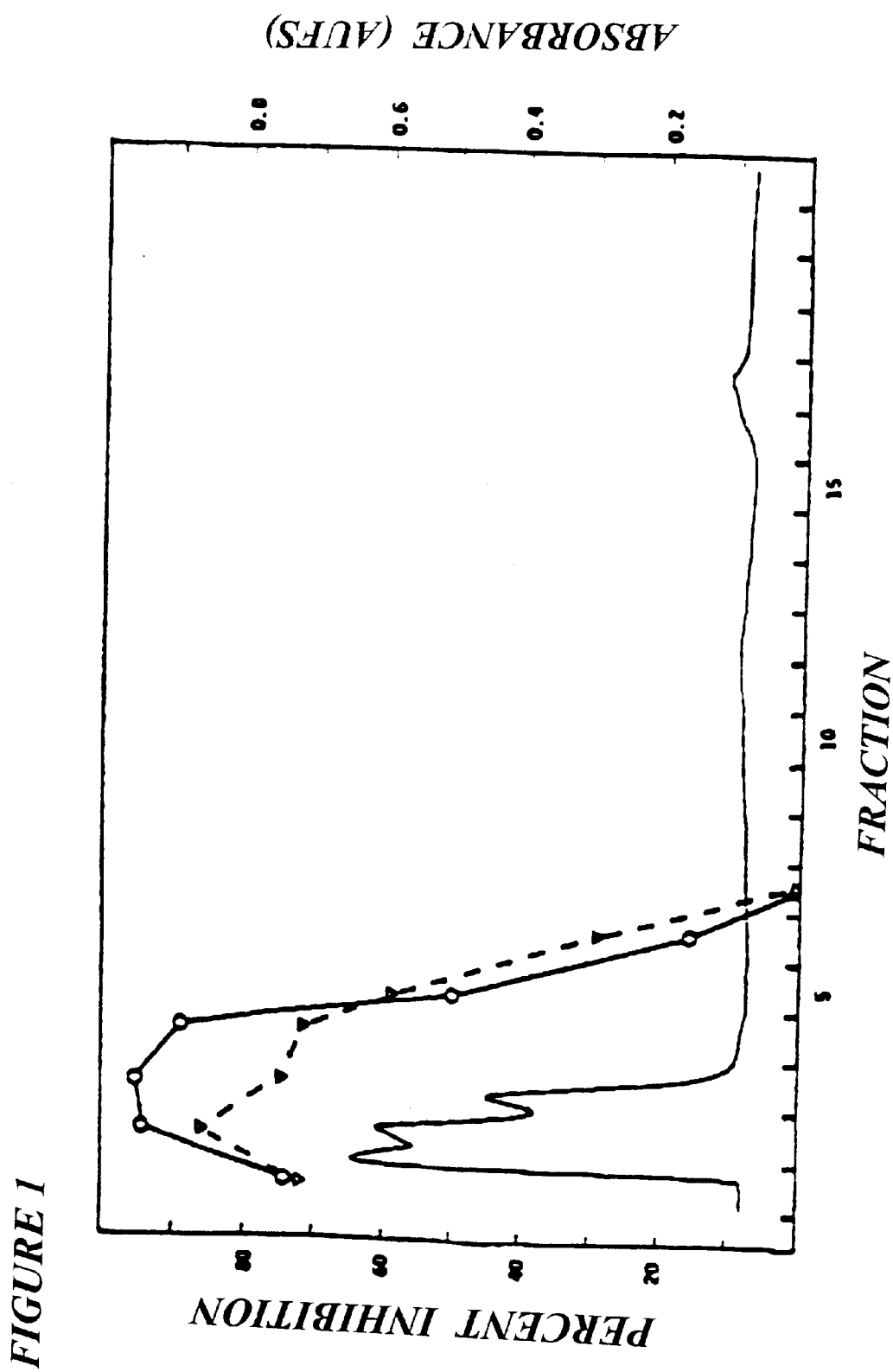
FIG. 1. Gel filtration chromatography at 23° C.

A comparison of Bio-Gel P-10 chromatograms performed at room temperature and 4° C., illustrated in FIGS. 1 and 2, respectively, clearly indicates that inhibitory activity is better preserved at 4° C. At 23° C., no activity is observed past fraction 6 (FIG. 1), while at 4° C., activity is extended for 4 more fractions to fraction 10. Most importantly, the net amount of activity recovered is at least two-fold higher when extracts are chromatographed at 4° C., since 80% or more TGI activity is obtained in 7 fractions at 4° C. (FIG. 2) and in only 3 fractions at 23° C. This was not due to a concentration of the same quantity of activity eluting in 3 fractions (23° C.) rather than being spread over 7 fractions (4° C.), but apparently to actual increase in the yield of TGI activity. One ml aliquots of fraction 5 from both columns separately and dilutions of these fractions to $\frac{1}{5}$ to $\frac{1}{125}$ was tested on both the human lung adenocarcinoma (A549) and mink lung cells (CCL64) (Table 1). The TGI activity of the undiluted fraction was 2-fold higher in the fraction 5 obtained from chromatography at 4° C. Moreover, a 25-fold dilution of fraction 5 from chromatography at 4° C. continued to yield maximum TGI activity against the human tumor cell line. A fraction of equivalent dilution from chromatography at 23° C. showed no detectable activity. A similar observation was made with the mink cell line.

This information was not based on activities observed in FIGS. 1 and 2 but from two separate columns which demonstrated equivalent TGI activities in their respective fifth fraction.

Comparison of the Effects of TGIs on Normal Human Fibroblasts (HuFs) and Transformed Human Lung Carcinoma Cells (A549)

Aliquots of fractions obtained from human umbilical cord acidified, ethanol extracts chromatographed on a Bio-Gel P-10 resin, (4° C.), were tested for TGI activity on human normal and transformed cells as described in Materials and Methods. As illustrated in FIG. 3, TGI activity against human A549 cells (open triangles) ranged from fractions 3 to 12, while these same fractions induced as much as an 85% increase in growth stimulation of the normal human fibroblasts. Thus, the inhibitory activity is specific for human tumor cells. This observed inhibitory activity is not due to cytotoxicity, as demonstrated by light microscopic studies and indirectly by its stimulatory effect on normal human fibroblasts. The TGIs have previously been tested on "normal" epithelial derived cells and similar results were observed.

High Performance Liquid Chromatography (HPLC)

TGIs from acid ethanol extracts of human umbilical cords partially purified by gel filtration on a Bio-Gel P-10 column followed by further purification using reverse phase HPLC (uBondapack $C_{18}$ resin) inhibited the growth of both A549 human carcinoma and an established mink lung cell line, CCL64, but did not inhibit the growth of normal human fibroblasts. FIG. 4 illustrates an elution profile of the TGI activity obtained by HPLC using a linear profile of the TGI activity obtained by HPLC fraction 4 (19.8 mg/3 ml 0.05% trifluoracetic acid) derived from the Bio-Gel P-10 chromatographic step.

Evidence of two distinct peaks of growth inhibitory activities against both the A549 human carcinoma and the mink cells were observed. The fractions eluting between 28–34% (fractions 13–22) acetonitrile and 35–39% (fractions 25–31) acetonitrile were pooled separately and rechromatographed on a $C_{18}$ uBondapak column using a linear gradient of 2-propanol.

TABLE 1

EFFECT OF TEMPERATURE ON THE RECOVERY OF TGI
ACTIVITY FROM GEL FILTRATION CHROMATOGRAPHY

| TEMPERATURE OF COLUMN RUN | PERCENT INHIBITION OF THE TEST CELL | |
|---|---|---|
| | 4° C. | 23° C. |
| TEST CELL LINE | | |
| A549 (Human Carcinoma) | | |
| Undiluted | 57 | 30 |
| 1/5 | 62 | 25 |
| 1/25 | 54 | 0 |
| 1/125 | 15 | 7 |
| Mink lung (CCL 64) | | |
| Undiluted | 91 | 43 |
| 1/5 | 90 | 13 |
| 1/25 | 70 | 9 |
| 1/125 | 31 | 2 |

One ml aliquots from gel filtration on fraction 5 (FIGS. 1 & 2) containing 120 micrograms were used to assay TGI activity.

The first peak of TGI activity was designated TGI-1 and the second TGI-2. FIG. 5 demonstrates the elution profile and TGI activity of TGI-1 (FIG. 4). The concentration of injected material was 1.5 mg/1.5 ml of 0.05% trifluroacetic acid (TFA). TFI-1 activity elutes between 17–23% using a linear gradient of 2-propanol. Similarly, FIG. 6 indicates that TGI-2 (0.8 mg/1.8 ml 0.05% TFA) (FIG. 5) rechromatographed between 23–27% (fraction 17–23) using a linear gradient of 2-propanol. The TGI activity presented in FIGS. 4 and 5 are consistently 20% higher against the mink cells than against the A549 human carcinoma cells.

Another total fraction from the Bio-Gel P-10 chromatographic step, fraction 5 (see FIG. 3), was chromatographed by HPLC using a linear acetonitrile gradient (FIG. 7). Fraction 5, which was a later fraction than the material used in FIG. 4 (fraction 4), predominantly contained inhibitory activity eluting as TGI-1. In FIG. 7, TGI-1 eluted between 29–34% acetonitrile. Growth inhibitory activity was 35% higher against the mink cells than the A549 human carcinoma cells. The majority of TGI activity has now been separated from the peaks of protein. The active fractions (14–25) were pooled, lyophilized, and rechromatographed by reverse phase HPLC using a linear gradient of 2-propanol (FIG. 8). Evidence of differential growth inhibitory activity was observed. The TGI activities were separated into a growth inhibitory activity specific for mink cells eluting at a peak activity of 23% 2-propanol (fractions 22–25) and one specific for the A549 human carcinoma cells at 26% 2propanol (fractions 25–26). Therefore, a fraction eluting later from gel filtration chromatography that has less contaminating proteins [lower absorbence at 280 nm (FIG. 2) and less protein by gel electrophoresis] has two different cell-specific inhibitory activities.

Acid ethanol extracts of human placenta contained TGI activities which, following a gel filtration chromatographic step, also eluted between 26–34% acetonitrile of a $C_{18}$ column using a linear acetonitrile gradient containing 0.05% TFA.

In a subsequent experiment, the tissue derived growth inhibitor (TGI) corresponding to Fraction 4 of the BioGel P10 eluate described above was rechromatographed by HPLC on a C18 support, first with an acetonitrile gradient and then on a C18 support with a gradient of 2-propanol, as described above. The gel was stained and destained, and then washed extensively with deionized water. The lane containing the sample was cut into 42 approximately equal slices of 3 mm width. The slices were transferred to 1.5 ml siliconized polypropylene tubes, 0.1 ml of 50% acetonitrile/ 10 mM HCl added (at 25° C.), and the gel slice ground using a Teflon pestle. The tubes were then shaken on a rotary shaker overnight at 4° C., the gel fragments pelletted by centrifugation for 5 min on a microfuge (~15000×g), and the supernatant analyzed for bioactivity in the mink cell inhibition assay as described above. Bioassays of this material indicated that TGI activity was associated with a 25 kD band. The TGI activity was not detected in other gel slices. Approximately 25% of the TGI activity applied was recoverable from this gel slice. This amounted to an estimated 25 ng of the 25 kD MW protein.

Amino Acid Sequence from the N-terminus of TGI

The protein from the biologically active band was recovered and submitted to the Edman degradation procedure (see for example Creighton, Thomas E., "Proteins" W. H. Freeman and Co. 1984). The biologically active at band 25 kD was clearly resolved from other proteins. This band was excised and a portion was subjected to N-terminal sequencing by the Edman degradation procedure using an Applied BioSystems (ABI) 475 Automatic Protein Sequencer according to standard procedures as recommended by the manufacturer. Samples were sequenced with and without prior reduction and alkylation to allow detection of cysteine residues. The N-terminal amino acid sequence was determined to be Ala-Leu-Asp-Thr-Asn-Tyr-Cys-Phe-Arg-Asn-Leu-Glu-Glu-Asn-Cys-Cys-Val. The sequence obtained identifies the TGI protein as TGF-β3 (FIG. 15: sequence alignment).

Ion Exchange Chromatography

One gram of a lyophilized acidified, ethanol extract of human umbilical cords was directly subjected to ion exchange chromatography on CM-TRISACRYL in 0.01 M ammonium acetate, pH 4.0. A linear gradient was applied from 0.01 to 1.0 M ammonium acetate, pH 4.0. FIG. 9 demonstrates at least 4 separate TGI activities designated CM-I, CM-II, CM-III, and CM-IV. CM-I presently inhibited only the A549 human carcinoma cells at 60% inhibition (Table 2). CM peaks II and III have similar levels of growth inhibiting activity against both A549 human carcinoma (80 and 63%, respectively) and mink cells (61 and 76%, respectively). The last peak of activity (CM-IV) demonstrates a specificity in activity against mink (i.e. mink cells were more inhibited (95%) than were the A549 carcinoma cells (69%)). CM-I was not retained and CM-II was slightly retarded by the negatively charged resin since they both eluted before the gradient was started by 0.01 M ammonium acetate, pH 4.0.

Although all the proteins that have inhibitory activity are acidic proteins, since they are soluble at pH 4.0 and bind to a negatively charged resin, peaks CM-III and IV are probably slightly more basic they bind more tightly to the CM-TRISACRYL resin (eluting at greater than 0.5 M ammonium acetate). This is substantiated by the fact that no TGI activity was retained by a positively charged resin (i.e. DEAE-TRISACRYL) (data not shown). The more acidic inhibitory factors appear to be more specific for the A540 human carcinoma cells in their respective activities. These 4 peaks of TGI activities (CM-I, CM-II, CM-III, and CM-IV) have been repeatedly observed (6 separate chromatographic procedures with CM-TRISACRYL). To ensure that the TGI activities observed in CM-III and CM-IV would not yield material that could be eluted earlier from the column, and also to provide support for the notion that each peak of activity is a separate entity, material from CM-III and CM-IV was pooled, lyophilized, and rechromatographed using CM-TRISACRYL under the same conditions as the column from which it was derived. CM-III and CM-IV eluted (greater than 0.5 M ammonium acetate) in exactly the same position as did the original column fractions from which they were derived, (FIG. 10). The higher TGI inhibitory activity against mink cells was preserved and the difference between the inhibitory activity against the two cell line remained exactly the same at 25–30% around the peak or activity.

Physical and Biological Characterization of Tissue Derived Tumor Cell Growth Inhibitory Activity (TGIs)

Fractions 2, 4, and 6 derived from gel filtration chromatography by Bio-Gel P-10 were either heat treated (Table 3) or reduced by dithiothreitol (DTT) treatment (Table 4). All fractions tested retained TGI activity following either heat or acid treatment (see Table 5). Fractions 2, 4 and 6 were found to inhibit human cancer cell growth and stimulate normal human cell growth. TGI activity in fractions 2 and 6 was decreased by treatment with DTT, while the TGI activity in fraction 4 was actually slightly increased (Table 4). This information further substantiates the existence of separate TGIs.

TABLE 2

TGI ACTIVITY FROM CATION EXCHANGE CHROMATOGRAPHY

| PEAK OF TGI ACTIVITY | PERCENT INHIBITION OF THE TEST CELL | |
| --- | --- | --- |
| | A549 | Mink |
| CM I | 60 | 0 |
| CM II | 80 | 61 |

TABLE 2-continued

TGI ACTIVITY FROM CATION EXCHANGE CHROMATOGRAPHY

| PEAK OF TGI ACTIVITY | PERCENT INHIBITION OF THE TEST CELL | |
| --- | --- | --- |
| | A549 | Mink |
| CM III | 63 | 76 |
| CM IV | 69 | 95 |

Protein concentrations for the fractions tested for TGI activity ranged from 15–300 $\mu$g.

TABLE 3

EFFECT OF HEAT TREATMENT ON TGI ACTIVITY OF FRACTIONS FROM GEL FILTRATION CHROMATOGRAPHY

| | A549 | | MINK | |
| --- | --- | --- | --- | --- |
| COLUMN FRACTION | CONTROL PERCENT INHIBITION | AFTER HEAT TREATMENT PERCENT INHIBITION | CONTROL PERCENT INHIBITION | AFTER HEAT TREATMENT PERCENT INHIBITION |
| 2 | 16 | 32 | 54 | 68 |
| 4 | 63 | 65 | 78 | 80 |
| 6 | 70 | 63 | 82 | 71 |

Protein concentrations for the fractions tested for TGI activity ranged from 15–300 $\mu$g.

TABLE 4

EFFECT OF DTT TREATMENT ON TGI ACTIVITY OF FRACTIONS FROM GEL FILTRATION CHROMATOGRAPHY

| | A549 | | MINK | |
| --- | --- | --- | --- | --- |
| COLUMN FRACTION | CONTROL PERCENT INHIBITION | AFTER HEAT TREATMENT PERCENT INHIBITION | CONTROL PERCENT INHIBITION | AFTER HEAT TREATMENT PERCENT INHIBITION |
| 2 | 31 | 8 | 69 | 17 |
| 4 | 63 | 69 | 79 | 69 |
| 6 | 71 | 34 | 78 | 26 |

Protein concentrations for the fractions tested for TGI activity ranged from 5–300 $\mu$g.

TABLE 5

PHYSICAL AND BIOLOGICAL PROPERTIES OF TISSUE-DERIVED TUMOR CELL GROWTH INHIBITORY ACTIVITY (TGI)

| | Column Fraction | | |
| --- | --- | --- | --- |
| | Fraction 2 | Fraction 4 | Fraction 6 |
| Stable to 1.0 M acetic acid | + | + | + |
| Stable to boiling at 100° C. | + | + | + |
| Inhibits human cancer cells | + | + | + |
| Inhibits normal human cells | − | − | − |
| Inactivated by dithiothreitol | + | − | + |

Second Series of Experiments
Materials and Methods

Isolation of Tissue-Derived Tumor Growth Inhibitors (TGIs) from Tissue Extracts Depleted of Blood, Veins, and Arteries Veins and arteries were removed from umbilical cord tissues and the remaining tissues were extensively washed to remove blood prior to acid/ethanol extraction as described under First Series of Experiments.

The buffer for washing and homogenizing the tissue (PBS-PA) consisted of 2 liters of water containing 16 gm NaCl, 2.5 gm $Na_2HPO_4$ $H_2O$, 0.4 gm $Na_2HPO_4$ $7H_2O$, 116 mg phenylmethylsulfonyl fluoride (PMSF) (Sigma P7627) and 3.3 ml of Aprotinin (Sigma A6012 with 19.8 units Trypsin inhibitor per ml in 0.9% NaCl and 0.9% benzyl alcohol) adjusted to pH 7.4 with HCl and NaOH. The extraction buffer consisted of 375 ml of 95% (v/v) ethanol (punctilious, 190 proof, U.S. Industrial Chemicals, #UN1170), 7.5 ml of concentrated HCl, 33 mg of phenylmethylsulfonyl fluoride (PMSF) (Sigma P-7627) and 1 ml of Aprotinin (Sigma A6012) mixed with 192 ml of distilled water at 4° C. Eight hundred to one thousand grams of frozen human umbilical cords (Advanced Biotechnologies; stored at −80° C.) were thawed by immersion in PBS-PA for two hours at 4° C. Individual umbilical cords were removed and rinsed with PBS-PA. Veins and arteries were removed from the umbilical cords by dissection at 4° C. The dissected umbilical cord was washed with fresh PBS-PA to remove residual blood and vascular depris.

The tissue was placed in a 4° C. chilled Cuisinart food processor (Model DLC-7-PRO) and suspended in 200 ml of 4° C. PBS-PA. The suspended tissue was homogenized by food processor. After the first minute of homogenization, an additional 200 ml of 4° C. PBS-PA was added. The tissue suspension was homogenized for a total of 10 min. at 4° C. The homogenate was transferred to 200 ml centrifuge bottles (Sorvall) and centrifuged and 9000 rpm (RCF=13,000) for 5 minutes at 4° C. in a Sorvall RC5B centrifuge equipped with a Sorvall GSA rotor. The supernatant fluid was removed and discarded and the pellet resuspended to the original homogenate volume with fresh PBS-PA.

The pellet was washed by repeated centrifugation and resuspension as described until the supernatant fluid was clear with no tint of red from contaminating blood or blood products. The resulting washed pellet was white. The washed pellet was resuspended in the buffer for extraction to a final volume of 6 ml per gram of original dissected tissue. The homogenate was transferred to a large 4 liter beaker with a 3 inch stirred at half of the maximum stirring capacity of a LAB-line Multimagnestir multimixer, Model #1278. After overnight extraction with stirring at 4° C., the homogenate was transferred to 1 liter centrifuge bottles (Sorvall) and centrifuged at 3500 rpm (RCF=3570) for 30 minutes at 4° C. in a Sorvall RC-3B centrifuge equipped with a Sorvall H-6000A rotor. The supernatant was transferred to a large 4 liter beaker and adjusted to pH 5.0 with the slow addition of concentrated ammonium hydroxide. With increasing pH, the supernatant remained clear with a slight yellowish tint. A 2.0 M solution of ammonium acetate, pH 5.2, was added in an amount 1% of the total volume. Any precipitate formed by this step was removed by centrifugation at 4500 rpm (RCF=5900) for 4 hours in a Sorvall RC-3B at 4° C. The supernatant was transferred to large 6 liter flasks to which four volumes of anhydrous ether (−20° C.) (Baker #9244-3) and two volumes of 95% ethanol (4° C.) were added. The mixture was allowed to stand undisturbed at −20° C. for 48 hours to allow the resulting precipitate to settle.

At the end of the 48 hr precipitation, the material was brought to ambient temperature in a fume hood. Warming of the acidified, ethanol extract to ambient temperature enhances the aggregation of the precipitate. The clear organic phase of ether and ethanol was removed by a water aspirator and the precipitate remained in the fume hood for several hours to allow the residual organic phase to evaporate. A gentle stream of dried nitrogen gas over the extract accelerated the evaporation of the remaining organic solvent present with the precipitate. The "dried" precipitate was dissolved in 1.0 M acetic acid and dialyzed extensively against 1.0 M acetic acid (Baker #9507-5) using dialysis membranes with a molecular weight cutoff of 3500 (Spectropor 3, Spectrum Medical Industries, Los Angeles, Calif.). The dialyzed acidified extract was lyophilized in 250 ml Corning conical centrifuge tubes (Corning 25350) and stored at crude acidified, ethanol extract or dialyzed extensively against 20 mM $NH_4O_2C_2H_3$, pH 4.5.

Comparison of TGI activity in the initial acid/ethanol extract from tissue prepared as described in the First Series of Experiments with tissue prepared as described above.

The improvement in the specific activity and total recovered activity seen when the tissue was prepared as described above is shown in Table 6. The table compares the yields of protein and TGI activity from frozen umbilical cord when it was processed according to the procedures detailed in the First Series of Experiments (hereinafter "initial procedure") and when it was processed as described above (hereinafter "modified procedure").

There are several obvious differences in the two procedures which are of importance for the subsequent purification of TGI. For example, based on the wet weight of the tissue, acidified ethanol extraction by the initial procedure resulted in the recovery of 0.33% as protein (3.3 g from 1000 g tissue) whereas only 0.015% as protein (0.05 g from 340 g tissue) was extracted when following the modified procedure. Because the yield of activity was 50% greater ($3.3 \times 10^6$ units) by the modified procedure than in the initial procedure ($2 \times 10^6$ units) from 66% less tissue (349 g vs 1000 g) the overall efficiency of extraction was improved. The initial procedure yielded 2000 units of TGI activity per gram of umbilical cord (wet weight). The modified procedure yielded 9700 units of TGI activity per gram of umbilical cord (wet weight). The overall efficiency of extraction was improved 5-fold by the modified procedure. Furthermore, since less protein was extracted by acidified ethanol, the volumes of ether and ethanol required to precipitate the extracted proteins are less. Finally, the amounts of protein and the numbers of different proteins extracted by the modified procedure are fewer and therefore the subsequent purification procedures to be employed will require less chromatographic materials, shorter processing times and fewer steps to obtain a pure product.

Fractionation of TGI extracted using the modified procedure on the cation exchange resin CM-TRISACRYL was resolved as a single peak from the bulk of the applied protein when the bound material was eluted by a linear salt gradient from 0–1.0 M NaCl. FIG. 11 shows that following application of TGI to a CM-TRISACRYL column no inhibitory activity was

TABLE 6

Comparison of TGI Activity in the Initial Acid/Ethanol Extract
from Tissue Prepared as Described in the Initial Procedure
with that Prepared as Described in the Modified Procedure

| Tissue[1] (wet weight) | Procedure | Protein (extracted) | Total[2] Activity | Specific[2] Activity |
|---|---|---|---|---|
| 1000 g | initial | 3.0 g | $2 \times 10^6$ u | 0.67 u/µg protein |
| 340 g | modified | 50 mg | $3 \times 10^6$ u | 67 u/µg protein |

[1]Human umbilical cord
[2]A unit of activity is defined as that amount of material which results in 50% of the maximal inhibition seen with a given cell line, e.g., the A549 (as used for this table) cell line is maximally inhibited 60%, therefore a unit of activity is equivalent to 30% inhibition.

detectable from material not bound to the resin (i.e., fractions 1–24). The linear addition of increasing amounts of NaCl (- - -) removed the majority of protein bound to the resin (fractions 25–38) prior to the removal of significant amounts of inhibitory activity ($^\triangledown$- - -$^\triangledown$, fractions 39–49). The NaCl concentration most effective in removing bound TGI was approximately 0.6 M (fraction 44). Comparison of FIG. 11 with FIG. 10 suggests that the inhibitory activity eluted in the experiment of FIG. 11 most closely corresponds to the elution of CM-III and CM-IV from the CM-TRISACRYL resin as depicted in FIG. 9 since the salt concentrations (NaCl, FIG. 11; $NH_4O_2$—$C_2H_3$, FIG. 10) for elution are similar (0.6 M, FIG. 11; 0.6–0.7 M, FIG. 10). The above information also suggests that treatment of the tissue by the modified procedure allows the preferential isolation of a single type of TGI, thus improving subsequent characterization of the factor.

Another property of the TGI extracted from the tissue by the modified procedure is its failure to bind to anion exchange resin. FIG. 12 shows that following adjustment of the pH to 8.0 as described in the figure legend and application of the extract (an identical amount to that used in FIG. 11) to the anion exchange resin DEAE-TRISACRYL resulted in the majority of inhibitory activity associating with nonbinding material (fractions 1–30), whereas the bulk of the applied protein (as determined by absorbance at 280 nm, _____) bound to the column resin. These results show that under the conditions of FIG. 12, contaminating proteins can be removed from TGI and, therefore, that it is a useful procedure for purification of TGI. In addition, these results show that the pH 8.0, TGI is a cation since it does not bind the anion exchange resin. Finally, the results of FIG. 12 show that TGI as extracted by the modified procedure is similar in ionic character to those polypeptides (TGI-1, TGI-2, CM-I, CM-II, CM-III and CM-IV) extracted by ion exchange resin in the initial procedure since none of these bound to the anion exchange resin.

Large amounts of sample can be reproducibly fractionated by CM-TRISACRYL, thus furnishing more TGI for subsequent purification procedures. In FIG. 13, 9.9 mg of tissue extract were applied to a CM-TRISACRYL column (15 ml) under the same chromatographic conditions as shown in FIG. 12 for a smaller sample size (2.65 mg protein) on a smaller CM-TRISACRYL column (5 ml). Resolution of TGI activity from the majority of proteinaceous material by a linear gradient of NaCl was essentially the same in both experiments.

FIG. 14 shows fractionation of pooled samples (FIG. 13, fractions 59–78) from a CM-TRISACRYL column by HPLC on a uBondapac $C_{18}$ column. Following application of the sample, no significant inhibitory activity was observed by linearly increasing acetonitrile concentrations from 0–25%. However, TGI activity against both A549 (human lung carcinoma) and CCL64 (mink lung, 0—0) eluted a single peak between 28–34% acetonitrile (fractions 21–31) while the majority of material absorbing at 206 nm was eluted at lower (fractions 11–19) and at higher (fractions 37–50) acetonitrile concentrations. The similarities in the activity profile, absorbance at 206 nm, and the concentrations of acetonitrile which effectively elute TGI activity between FIG. 7 and FIG. 14 offer strong evidence that TGI isolated by the modified procedure is similar to or identical to that termed TGI-1 under the first Series of Experiments.

An apparent molecular weight of TGI (termed TGI-1 and CM-III and CM-IV in the initial procedure) was determined by gel filtration chromatography (Sephadex G-50, data not shown) using suitable protein standards of known molecular weights. Thus, in the absence of certain interfering proteins (e.g., hemoglobin) the apparent molecular weight of TGI has been determined to be between 20 kDa and 30 kDa under nondenaturing conditions.

The modified procedure detailed herein describes a powerful and simple procedure for removing inert or interfering compounds from the TGI-containing extracts prepared as described in the initial procedure. Furthermore, the modified procedure improves the efficacy of the various chromatographic steps employed in the isolation of TGI by reducing the amount of chromatographic material required thus reducing the preparation time of TGI. In addition, and as shown, extraction of TGI from the umbilical cord as described herein allows TGI and other proteins to chromatograph more reproducibly than in the procedure previously described.

TGI isolated according to the modified procedure has been characterized with respect to the chromatographic features on both reverse phase high performance liquid chromatography and CM-TRISACRYL ion exchange chromatography. TGI has been found to behave similarly to or identically with TGI-1 (compare FIGS. 7 and 14) by rp-HPLC, and thus has similar or identical hydrophobic properties and is shown also to behave similarly to or identically with CM-III and CM-IV (compare FIGS. 9 and 11) on a cation exchange resin, thus having similar or identical ionic properties. It is therefore concluded that TGI as isolated in the modified procedure and TGI-1 and CM-III and CM-IV are similar or identical compounds having similar or identical ionic and hydrophobic properties and thus are of similar or identical composition. Therefore, the modified procedure described herein provides a more efficacious method of obtaining a purer form of TGI for further analysis and characterization.

DETAILED DESCRIPTION OF THE INVENTION

An acidified, ethanol extract derived from human tissue has been produced. This extract comprises a plurality of proteins. Each of the proteins has an apparent molecular weight less than about 30,000 daltons, specifically about 26,000 daltons, is a dimer composed of two polypeptides each which has an apparent molecular weight of about 13,000 daltons and each dimer is joined to the other by disulfide bonds under nonreducing conditions. The extract has the property of inhibiting the growth of human tumor cells and of an established mink lung cell line (CCL64) while stimulating the growth of normal human foreskin fibroblasts. The inhibitory activity of the extract against human tumor cell growth is not destroyed upon increasing the temperature of the acidified, ethanol extract to about 100° C. for about 3 minutes or upon adding acetic acid until the extract is up to about 1.0 molar in acidic acid. The inhibitory activity of the acidified, ethanol extract is enhanced when it is prepared at about 4° C. rather than at about 23° C. In a preferred embodiment the human tissue is human umbilical cord, although other tissues, e.g. human placenta, may be used.

An acidified, ethanol extract derived from human umbilical cord which has been treated to remove substantially all blood and all extracellular soluble components has also been produced which comprises at least two acidic proteins. Each of the proteins has an apparent molecular weight less than about 30,000 daltons, and specifically about 26,000 daltons, is a dimer of two polypeptides each of which has an apparent molecular weight of about 13,000 daltons and is joined by disulfide bonds under non reducing conditions. The extract has the property of inhibiting the growth of human tumor cells and of an established mink lung cell line (CCL64) while stimulating the growth of normal human foreskin fibroblasts. The inhibitory activity against human tumor cell growth is not destroyed upon increasing the temperature of the acidified, ethanol extract to about 100° C. for about 3 minutes or upon adding acetic acid until the acidified, ethanol extract is up to about 1.0 molar in acetic acid.

Various components of the acidified, ethanol extract may be prepared using techniques known to those skilled in the art, e.g., high performance liquid chromatography and cation exchange chromatography. Thus, a protein designated tissue-derived growth inhibitor-1 (TGI-1) has the property of inhibiting the growth of human tumor cells and of an established mink lung cell line (CCL64) but not the growth of normal human foreskin fibroblasts. TGI-1 has an apparent molecular weight of about 26,000 daltons and is a dimer composed of two polypeptides each of which has an apparent molecular weight of about 13,000 daltons and each is joined to the other by disulfided bonds under nonreducing conditions. TGI-1 is recoverable, as a defined activity on hydrophobic interaction chromatography on phenyl-Sepharose after ether ethanol precipitation at about 1.5M ammonium acetate and 31% ethelene glycol and on high performance liquid chromatography of the acidified, ethanol extract with a separating gradient of acetonitrile on a C18 column containing 0.05% trifluoroacetic acid at about 26–34% and preferably 27% acetonitrile and is recoverable as a defined activity on high performance liquid chromatography on the acidified, ethanol extract with a separating gradient on a CN column of 2-propanol containing 0.05% trifluoroacetic acid at about 40–41% 2-propanol.

Another composition of matter designated tissue-derived growth inhibitor (TGI) which comprises at least two polypeptides having the property of inhibiting the growth of human tumor cells and of an established mink lung cell line (CCL64) but not the growth of normal human foreskin fibroblasts is described. TGI has an apparent molecular weight in the range from about 20,000–30,000 daltons and preferably about 26,000 daltons. TGI is resolved as a single peak of defined activity from a cation exchange resin, e.g., CM-TRISACRYL resin when eluted by a linear NaCl gradient at about 0.6–0.7 M NaCl, is recoverable as a defined activity on high performance liquid chromatography of an acidified, ethanol extract with a linear gradient of acetonitrile containing 0.05% trifluoroacetic acid at about 28–34% acetonitrile, and is recoverable as a defined activity on high performance liquid chromatography of an acidified, ethanol extract from human umbilical cord with a separating gradient of phenyl-Sepharose.

Another composition of matter designated tissue-derived growth inhibitor-2 (TGI-2) which is a protein which has the property of inhibiting the growth of human tumor cells and of an established mink lung cell line (CCL64) but not the growth of normal human foreskin fibroblasts. TGI-2 has an apparent molecular weight of about 26,000 daltons and is a dimer composed of two polypeptides each of which has an apparent molecular weight of about 13,000 daltons and each is joined to the other by disulfide bonds under nonreducing conditions. TGI-2 is recoverable, as a defined activity on high performance liquid chromatography of an acidified, ethanol extract with a separating gradient of acetonitrile on a C18 column containing 0.05% trifluoroacetic acid at about 35–39% acetonitrile and as a defined activity on hydrophobic interaction chromatography on phenyl-Sepharose after ether ethanol precipitation of about 1.5M ammonium acetate and 31% ethelene glycol and on high performance liquid chromatography of the acidified, ethanol extract with a separating gradient of 2-propanol on a CN column containing 0.05% trifluoroacetic acid at about 43–45% and preferably 44% 2-propanol.

Additionally, a polypeptide designated CM-I, having the property of inhibiting the growth of human tumor cells, but not the growth of an established mink lung cell line (CCL 64) and being recoverable by cation exchange chromatography of the acidified, ethanol extract.

Finally, a polypeptide recoverable from condition media of A431 cells having an apparent molecular weight of less than about 30,000 daltons and having the property of substantially inhibiting the growth of a human cell line (CCL 64) but not of an established mink lung cell line (CCL 64).

A protein having the characteristics of an apparent molecular weight of about 26,000 daltons. The protein is a dimer composed of two polypeptides having an apparent molecular weight of about 13,000 daltons and being joined by disulfide bonds. The protein demonstrates tumor growth inhibitory activity of human tumor cell line (A549) and of an established mink lung cell line (CCL 64). It is acid soluble in 1.0 M acetic acid; and 0.1% trifluoracetic acid and is stable in heat to about 100° C.; and is stable in up to 39% acetonitrile and 45% 2-propanol. The protein is designated TGI-1 or TGI-2.

TGI-1, TGI, TGI-2, CM-I, or the polypeptide recoverable from condition media of A431 cells or various combinations thereof, may be used in pharmaceutical compositions which comprise an effective amount of TGI-1, TGI, TGI-2, CM-I, or the polypeptide recoverable from condition media of A431 cells together with a suitable pharmaceutical carrier. Effective amounts may vary among the various tumor growth inhibitors depending on the indication to be treated, the patient or the stage of tumor development, by methods well known to those skilled in the art. Similarly, suitable carriers such as saline or other aqueous solutions, gels, creams and the like are well known to those skilled in the art.

TGI-1, TGI, TGI-2, CM-I, or the polypeptide recoverable from condition media of A431 cells may be used to inhibit the growth of human tumor cells, e.g., carcinoma, melanoma or leukemia cells, by contacting the cells with an effective growth inhibiting amount of TGI-1, TGI, TGI-2, CM-I, or the polypeptide recoverable from condition media of A431 cells. TGI-1, TGI, TGI-2, CM-I, or the polypeptide recoverable from condition media of A431 cells may also be used to treat burns or to facilitate the healing of wounds by contacting the burn or wound with a pharmaceutical composition which includes an effective amount of TGI-1, TGI, TGI-2, CM-I, or the polypeptide recoverable from condition media of A431 cells and a suitable pharmaceutical carrier.

A method is disclosed for preparing the acidified, ethanol extract from human tissues, the acidified, ethanol extract comprising a plurality of proteins, each of which has a molecular weight less than about 30,000 daltons and preferably about 26,000 daltons and each of which has the property of inhibiting the growth of human tumor cells and of an established mink lung cell line (CCL64) while stimulating the growth of normal human foreskin fibroblasts, the method comprising under suitable conditions treating the tissue e.g., by treating the tissue to solubilize the proteins and removing the solubilized proteins derived from the tissue, recovering the solubilized proteins, separately recovering from the solubilized tissue, proteins having an apparent molecular weight of less than about 30,000 daltons, assaying the separately recovered proteins to identify those which either inhibit the growth of human tumor cells or inhibit the growth of an established mink lung cell line (CCL 64) or enhance the growth of normal human foreskin fibroblasts, and recovering an acidified, ethanol extract containing the proteins so identified.

In a present embodiment, treating the tissue comprises suspending the tissue in a suitable acidic extraction buffer containing ethanol of about 4° C. and homogenizing the tissue for a suitable period of time to form homogenized tissue, stirring the homogenized tissue for a suitable period at about 4° C. to produce solubilized proteins.

In a present embodiment the separate recovery of polypeptides from the solubilized proteins comprises molecular sieve chromatography of the proteins.

In a present embodiment, assaying the proteins comprises separately contacting the human tumor cells, an established mink lung cell line (CCL 64) or normal human foreskin fibroblasts under suitable conditions for a suitable period with the polypeptides so as to identify polypeptides which inhibit the growth of human tumor cells, inhibit the growth of the established mink lung cell line (CCL 64) or which enhances the growth of normal human foreskin fibroblasts.

A method is also disclosed for preparing an acidified, ethanol extract from human umbilical cord, the acidified, ethanol extract comprising tissue-derived growth inhibitor (TGI) comprised of at least two proteins which have an apparent molecular weights of about 20,000–30,000 daltons and preferably about 26,000 and which has the property of inhibiting the growth of human tumor cells and of an established mink lung cell line (CCL64) while stimulating the growth of normal human foreskin fibroblasts. The method comprises under suitable conditions, removing veins and arteries from the umbilical cord tissue and washing the tissue to remove all traces of blood, treating the tissue to produce solubilized proteins and removing the soluble containing proteins derived from the cells. Then separately recovering from the solubilized proteins TGI having an apparent molecular weight of about 26,000 daltons and assaying the separately recovered TGI to identify the activity of which inhibits the growth of human tumor cells, inhibits the growth of an established mink lung cell line (CCL64) and enhances the growth of normal human foreskin fibroblasts. Finally, recovering the acidified, ethanol extract containing the TGI so identified.

In a present embodiment, treating the tissue comprises suspending the tissue in a suitable buffer at about 4° C. and homogenizing the tissue for a suitable period of time to produce soluble proteins.

In a present embodiment, treating the tissue comprises suspending the homogenized, washed tissue in acidified ethanol for a suitable period of time to extract acid soluble proteins.

In a present embodiment, assaying the TGI comprises separately contacting the human tumor cells, e.g, human lung carcinomal line (A549), or an established mink lung cell line (CCL64), or normal human foreskin fibroblasts (HuF), under suitable conditions for a suitable period of time with the TGI so as to identify the activity which inhibit the growth of the human tumor cells or inhibit the growth of the established mink lung cell line (CC164) or which stimulates the growth of normal human foreskin fibroblasts.

A method is disclosed for preparing an acidified, ethanol extract from human umbilical cord, the acidified, ethanol extract comprising tissue-derived growth inhibitor 1 (TGI-1) and tissue-derived growth inhibitor 2 (TGI-2) which have a molecular weight of about 26,000 daltons and which have the property of inhibiting the growth of human tumor cells and of an established mink lung cell line (CCL 64) while stimulating the growth of normal human foreskin fibroblasts. The method comprises under suitable conditions, removing the blood constituent by washing, treating the tissue to produce solubilized proteins and removing contaminating proteins derived from the tissue; recovering the solubilized proteins; separately recovering from the solubilized proteins TGI-1 and TGI-2 having a molecular weight of about 26,000 daltons. Then assaying the separately recovered TGI to identify the activity which inhibits the growth of human tumor cells, inhibits the growth of an established mink lung cell line (CCL 64) and enhances the growth of normal human foreskin fibroblasts. Finally, recovering the acidified, ethanol extract containing the TGI so identified.

In a present embodiment, treating the tissue comprises suspending the tissue in a suitable acidic extraction buffer and homogenizing the tissue at about 4° C. for a suitable period of time to form homogenized tissue.

In a present embodiment, recovering the acid solubilized proteins comprises suspending washed tissue in a suitable acidic extraction buffer containing ethanol at about 4° C. for a suitable period of time.

In a present embodiment the assaying the TGI-1 and TGI-2 comprises separately contacting the human tumor cells, an established mink lung cell line (CCL 64) or normal human foreskin fibroblasts under suitable conditions for a suitable period with the polypeptides so as to identify the TGI-1 and TGI-2 which inhibit the growth of the established mink lung cell line (CCL 64) or which enhance the growth of normal human foreskin fibroblasts.

In a present embodiment the separate recovery of polypeptides from the solubilized proteins comprises hydrophobic interaction chromatography using phenyl-Sepharose.

A method for preparing a composition of matter designated tissue-derived growth inhibitor-1 (TGI-1) which comprises first preparing the acidified, ethanol extract and then recovering TGI-1 from the acidified, ethanol extract as a defined activity by high performance liquid chromatography, e.g., purification of the acidified, ethanol extract by hydrophobic intersection chromatography in a phenyl-Sepharose column followed by reverse phase HPCL with either i) a separation gradient of acetonitrile on a C18 column containing 0.05% trifluoroacetic acid at about 25–34% acetonitrile and preferably 27% acetonitrile or ii) a separation gradient of 2-propanol containing 0.05% trifluoroacetic acid at about 40–41% 2-propanol.

A method for preparing a composition of matter designated tissue-derived growth inhibitor (TGI) which comprises first preparing an acidified, ethanol extract and then recovering TGI from the acidified, ethanol extract as a defined cavity on high performance liquid chromatography, e.g. reverse phase of HPLC of the acidified, ethanol extract with a linear gradient of acetonitrile containing 0.05% trifluoroacetic acid at about 28–34% acetonitrile, or as a single peak of activity from a cation exchange resin, e.g., CM-TRISACRYL resin when eluted with a linear NaCl gradient at about 0.6–0.7 M NaCl.

A method for preparing a composition of matter designated tissue-derived growth inhibitor-2 (TGI-2) which comprises first preparing the acidified, ethanol extract and then recovering TGI-1 from the acidified, ethanol extract as a defined activity by high performance liquid chromatography, e.g., purification of the acidified, ethanol extract by hydrophobic interaction chromatography in a phenyl-Sepharose column followed by reverse phase HPLC with either i) a separation gradient of acetonitrile on a C18 column containing 0.05% trifluoroacetic acid at about 28–30% acetonitrile or ii) a seperation gradient of 2-propanol containing 0.05% trifluoroacetic acid at about 43–45% and preferably about 44% 2-propanol.

A method of preparing a polypeptide designated CM-I, which comprises first preparing the acidified, ethanol extract and then recovering the CM-1 from the acidified, ethanol extract by ion exchange chromatography, e.g. cation exchange chromatography.

A method for detecting the presence of a tumor is disclosed. The method comprises quantitatively determining the amount of TGI-1, TGI, TGI-2, CM-I, or the polypeptide recoverable from conditioned media of A431 cells present in a sample, e.g., blood, amniotic fluid, peritoneal fluid, ascites fluid, cerebrospinal fluid or urine, from a subject and comparing the amount so determined with the amount present in a sample from a normal subject, the presence of a significantly different amount, e.g. a significantly higher amount, indicating the presence of a tumor.

Another method for detecting the presence of a tumor is disclosed. The method comprises separately quantitatively determining both the amount of TGI-1, TGI, TGI-2, CMI-I, or the polypeptide recoverable from condition media of A431 cells and of transforming growth factor alpha (TGF-alpha) present in a sample from a subject, determining the ratio of the amount of TGI-1, TGI, TGI-2, CM-I, or the polypeptide recoverable from condition media of A431 cells present in the sample to the amount of TGF-alpha present in the sample from a subject, determining the ratio of the amount of TGI-1, TGI, TGI-2, CM-I, or the polypeptide recoverable from conditioned media of A431 cells present in the sample, determining the comparable ratio for a sample from a normal subject and comparing the ratio for the sample from the subject to the ratio for the sample from the normal subject, a significant variation in the ratio indicating the presence of a tumor.

A method for typing tumors is disclosed which comprises determining for a sample from a subject with a tumor the presence of one or more TGI-1, TGI, TGI-2, CM-I, or the polypeptide recoverable from conditioned media of A431 cells, the presence or absence of a specific combination thereof, e.g., TGI and CM-I or TGI-1 and TGI-2 being indicative of a specific tumor type, e.g., a melanoma or a carcinoma.

Finally, a method for typing tumors is disclosed which comprises quantitatively determining for a sample from a subject with a tumor the amount of each of TGI-1, TGI, TGI-2, CM-I, or the polypeptide recoverable from conditioned media of A431 cells present in the sample, the presence of specific amounts or relative amounts thereof, e.g. a significant increase in the amount of TGI or a significant variation in a ratio such as the ratio of TGI-1 to CM-I.

EXPERIMENTAL DETAILS

Three sets of experiments are discussed below. Each series of experiments comprises a means of isolating proteins exhibiting tumor growth inhibitory activity. In the first series of experiments six discrete proteins are purified that demonstrated tumor growth inhibitory activity. These proteins were designated TGI, TGI-1, TGI-2 and CM I-IV. The second and third series of experiments are improvements of the purification process resulting in more purified proteins demonstrating tumor growth inhibitory activity.

Third Series of Experiments
Materials and Methods

Isolation of Tissue-Derived Tumor Growth Inhibitors (TGIs) from Tissue Extracts

Human umbilical cord or placenta tissues were extracted using a modification of the acid/ethanol extraction procedure described by Davoren et al (Biochem. Biophys. Acta. 63:150 (1962) and Roberts et al, Proc. Natl. Acad. Sci. USA. 77:3494 (1980).

The buffer for extraction consisted of 375 ml of 95% (v/v) ethanol (punctilious, 190 proof, U.S. Industrial Chemicals, #UN1170), 7.5 ml of concentrated HCl, 33 mg of phenylmethylsulfonyl fluoride (PMSF) (Sigma P-7627) and 1 ml of Aprotinin (Sigma A6012 with 19.8 Trypsin inhibitor units per ml in 0.9% NaCl and 0.9% benzyl alcohol) mixed with 192 ml of distilled water at 4° C. Four hundred to six hundred grams of frozen human umbilical cords or placentas (Advanced Biotechnologies) (stored at −80° C.) were thawed at 4° C. for six hours. The thawed tissue was placed in a 4° C. chilled Cuisinart food processor (Model DLC-7-PRO) and suspended in 200 ml of 4° C. extraction buffer. The suspended tissue was homogenized by the food processor. After the first minute of homogenization, the suspension became creamy white. Another 200 ml of 4° C. extraction buffer was added to this white suspension. The suspension changed to a dark coffee brown color. The tissue suspension was homogenized for a total of 10 min at 4° C. Extraction buffer was added to this homogenized tissue mixture to a final volume of 6 ml per gram of tissue homogenate.

The homogenized tissue suspension was transferred to a large 4 liter beaker with a 3 inch stir bar and stirred at half of the maximum stirring capacity of a Lab-line Multimagnestir multi-mixer, Model #1278. After overnight extraction with stirring at 4° C., the homogenate was transferred to 1 liter centrifuge bottles (Sorvall) and centrifuged at 3500 rpm (RCF=350) for 30 minutes at 4° C. in a Sorvall RC-3B centrifuge equipped with a Sorval H-6000A rotor. The supernatant was transferred to a large 4 liter beaker and adjusted to pH 5.0 with the slow addition of concentrated ammonium hydroxide. With increasing pH, the color of the supernatant changed from brown to an orange solution. The solution was precipitated following the addition of 2.0 M ammonium acetate, pH 5.2, added at an amount of 1% of the total volume. This precipitate was removed following centrifugation at 4500 rpm (RCF=5900) for 4 hours in a Sorvall RC-3B at 4° C. The supernatant was transferred to large 6 liter flasks to which four volumes of anhydrous ether (−20° C.) (Baker 9244-3) and two volumes of 95% ethanol (4° C.) were added. The mixture was allowed to stand undisturbed at −220° C. for 48 hours to allow the resulting precipitate to settle.

At the end of the 48 hr precipitation, the etherized material was brought to ambient temperature in a fumehood. Warming of the acidified, ethanol extract to ambient temperature enhances the aggregation of the precipitate. The clear organic phase of ether and ethanol was removed by a water aspirator and the precipitate was left in the fume hood for several hours to allow the residual organic phase to evaporate. The "dried" precipitate was dissolved in 1.0 M acetic acid and dialyzed extensively against 1.0 M acetic acid (Baker #9507-5) using dialysis membranes with a molecular cutoff of 3500 (Spectropor 3, Spectrum Medical Industries, Los Angeles, Calif.). The dialyzed acidified ethanol extract was lyophilized in 250 ml Corning conical centrifuge tubes (Corning 25350) and stored as crude acidified, ethanol extract.

An alternative procedure for precipitating TGIs from the acidified, ethanol extract replaces the addition of four volumes of ether and two of ethanol with the addition of only the two volumes of ethanol at 4° C. The advantage of eliminating ether from the acidified, ethanol extract precipitation step was the elimination of a step requiring the use of a highly flammable solvent which makes the procedure and any scale-up of the processing of large amounts of materials difficult.

Gel Filtration Chromatography

Lyophilized crude acidified, ethanol extract was resuspended in 1.0 M acetic acid (10–30 mg/ml) and clarified by centrifugation at 3500 rpm for 30 min at 4° C. in a Sorval RC-3B centrifuge equipped with a Sorvall H-6000A rotor before sample application to the column. Sample volumes of one hundred to 150 ml were chromatographed on Bio-Gel® P10, 100–200 mesh (Bio-Rad); 150–1040) in 1.0 M acetic acid at either 23° or 4° C.

The column (14×100 cm) (Amicon; #86012) contained 13.8 liters of equilibrated and degassed Bio-Gel® P10 in 1.0 M acetic acid at either 23° C. or 4° C. The void volume was determined by the addition of 50 ml of blue dextran (Sigma #D5751) at 2 mg/ml in 1.0 M acetic acid. After calibration, the column was "conditioned" with 100 ml of bovine serum albumin (Sigma #A-4503) at 100 mg/ml in 1.0 M acetic acid followed by extensive washing with 1.0 M acetic acid.

Following sample application, 1 liter fractions were collected using a SuperRac® (LKB 2211) equipped with a type C collection rack, at a flow rate of 7 ml/min into 2 liter plastic tissue culture roller bottles (Falcon; 3207). Fractions were monitored by a Uvicord® S (LKB 2138) at 280 nm set at an absorbance range of 2.0 AUFS and recorded by a single channel chart recorder (LKB 2210). One ml aliquots were removed from each fraction, lyophilized and assayed for tumor growth inhibitory activity as described. The remainder of each fraction was lyophilized in 2 liter lyophilization jars (Virtis® #6503-2050) using a Virtis freeze-model 24.

High Performance Liquid Chromatography (HPLC)

Individual fractions containing TGI activity from the Bio-Gel® P-10 column were lyophilized and resuspended in 1 to 10 ml of 0.05% trifluoracetic acid (TFA) (Pierce #28901) depending upon the amount of protein in each fraction. Water used for HPLC was generated using a Milli-Q water purification system. Starting buffer in all HPLC chromatography runs consisted of Milli-Q water containing 0.05% TFA. Prior to injection, the sample was centrifuged in a Beckman tabletop centrifuge (Beckman TJ-6) at 3000 rpm for 20 min to remove insoluble material. The supernatant was injected into either a Waters uBondpak® analytical $C_{18}$ column (0.39×30 cm) (Waters PN27324) or semipreparative column (0.78×30 cm) (Waters PN84176) as specified in individual experiments. A Waters automated gradient controller (Waters Model 510) was utilized for column elution monitored by a variable wavelength u.v. detectors (Waters Lambda-Max, Model 481) set at 206 nm. The solvent used for elution was either acetonitrile (Baker 9017-3) or 2-propanol (Fischer, A452) containing 0.05% TFA. Fractions were collected by a SuperRac® (LKB 2211) equipped with a type B collection rack into siliconized (Pierce, Aquasil #42799) 13×100 mm or 16×100 mm test tubes. Aliquots from each collected fraction were assayed for tumor growth inhibitory activity as described below.

Ion Exchange Chromatography

Both the lyophilized material from the acidified, ethanol and ether extractions and various lyophilized fractions derived from the Bio-Gel® P-10 gel filtration chromatography were separately subjected to ion exchange chromatography. CM, SP, and DEAE-TRISACRYL (LKB) ion exchange resins were used in these procedures. The samples for chromatography were diluted to a final concentration of approximately 20 mg/ml in 1.0 M acetic acid. The samples were dialyzed at 4° C. until both the pH and conductivity were equal to the starting (equilibration) buffer. All ion exchange chromatographic procedures were performed at 4° C.

a. Chromatography Using CM- and SP-TRISACRYL® Ion Exchange Results

The resins, as aqueous suspensions, were suspended in an equal volume of 0.1 M ammonium acetate, pH 4.0, containing 1.0 M NaCl. The resin was allowed to equilibrate for at least 3 hours and was degassed at 4° C. Twenty ml of resin was packed into a 1.6×20 cm column (Pharmacia; #19-0362-01) and washed with 2 column volumes of 1.0 ammonium acetate, pH 4.0, followed by 0.01 M ammonium acetate, pH 4.0. The column was washed until the effluent exactly matched the conductivity of the equilibrating buffer (i.e., 0.01M ammonium acetate, Fisher A637), pH 4.0. The sample was applied to the resin (1 gm/20 ml resin) at a flow rate of 1 ml/min, the column was washed with equilibration buffer until the optical density leveled (e.g., approaching zero optical density) and 200 ml of an ascending molarity linear gradient (Pharmacia gradient mixer GM-1, #19-0495-01) was applied through a column flow adaptor of concentrations 0.01 to 1.0 M ammonium acetate, pH 4.0. In certain experiments, a second gradient was applied to the same column. This second gradient ranged from 1.0 M ammonium acetate, pH 4.0, to 50% acetonitrile in 1.0 M ammonium acetate, pH 4.0. Two ml fractions were collected in polystyrene tubes, 13×100 mm, (Columbia Diagnostics; B2564) in a SuperRac® Fraction Collector (LKB 2211), equipped with an A type collection rack. All column chromatography was performed with the aid of a Uvicord S with a 280 nm filter (LKB 2138) and a single channel recorder (LKB 2210). Fractions were aliquoted based upon optical density ranging from 100 μl to 1 ml, and assayed for tumor growth inhibitory activity.

b. Chromatography Using DEAE-TRISACRYL

The chromatographic resin preparation and procedure was performed exactly as described for CM- and SP-TRISACRYL chromatography, except the equilibration buffer used was 0.1 M ammonium acetate, pH 6.0, the gradient elution ranged from 0.1 M to 1.0 M ammonium acetate, pH 6.0, and the sample was equilibrated in the above mentioned equilibration buffer.

Monolayer Assay for Tumor Growth Inhibitory Activity

Test cells were sub-cultured on 96-well tissue culture plates (Nunc 167008) in 50 ul of Dulbecco's® modified Eagle's medium (Whittaker M. A. Bioproducts 12-6143) containing 10% fetal bovine serum (Whittaker M. A. Bioproducts 14-501B), 2% L-glutamine (Whittaker M. A. Bioproducts 17-605-A), 1% penicillin and 1% streptomycin. Human lung carcinoma cells, A549, and normal human fibroblasts (HuF) required a seeding density of $5\times10^3$ cells per well. Mink cells (ATCC: CCL64) required a seeding density of $4.5\times10^3$ cells per well.

Aliquots from column fractions to be assayed for tumor growth inhibitory activity were transferred to sterile 12×75 mm tubes (Falcon 2058) containing 50 of microliters 1 mg/ml solution of bovine serum albumin (BSA; Sigma A-6003) in 1 M acetic acid and lyophilized. Immediately prior to the assay, the lyophilized sample was resuspended in 400 $\mu$l, for each cell type tested. One hundred microliter aliquots of the resuspended sample were added to wells containing test cells. Each sample was assayed in triplicate. The cells were incubated for 72 hours at 37° C. in a humidified 5% $CO_2$/95% air atmosphere. At the end of the incubation period, each well was pulsed with 100 microliters of complete medium containing 1 uCi/ml 5-[$^{125}$I]Iodo-2'-deoxyuridine ($^{125}$IUdR) (New England Nuclear; NEX-072) for 24 hours. The monolayers were washed once with wash buffer A (Dulbeco's phosphate buffered saline, with 10 mM $MgCl_2$, containing 1 mg/ml BSA, pH 6.8), fixed for 10 minutes in methanol (Fisher A452), and air dried for 15 minutes. The $^{125}$IUdR incorporated by the cells was solubilized with 200 microliters of 1.0 N NaOH and the plates incubated for 20 minutes at 60° C. Solubilized $^{125}$IUdR was collected using the Titertek Supernatant Collection System® (Skatron Inc., 7072). The amount of cell growth is approximated by the extent of $^{125}$IUdR incorporated into the DNA of cells in the log phase of growth. Before the assay was harvested each well was observed using a Zeiss® inverted microscope to visually note the amount of cell growth. Inhibition or stimulation of growth was expressed as a ratio of $^{125}$IUdR incorporated by test cells (e.g. human tumor cells) containing the test aliquots relative to $^{125}$IUdR incorporated by the untreated control cells. The inhibition or stimulation observed by microscopic examination of treated cells correspond well with decreased or increased incorporation of $^{125}$IUdR, respectively.

Characterization of TGI Activities
a. Heat Treatment

One ml aliquots from fractions 2, 4, and 6 obtained from gel filtration chromatography on Bio-Gel® P-10, were lyophilized in 12×75 mm polystyrene tubes (Falcon 2034) and resuspended in 1 ml of 1.0 M acetic acid. The samples were heated for 3 minutes in a boiling water bath, lyophilized, and assayed for tumor growth inhibitor activity as described above.

SDS-Polyacrylamide Slab Gel Electrophoresis

Aliquots from samples from each chromatography procedure were lyophilized for electrophoresis. Samples were diluted in 80 microliters of sample buffer containing 0.1 M Tris-HCl (Sigma; T-1503), pH 6.8, 15% glycerol (Kodak; 114-9939), 2% sodium dodecyl sulfate (SDS) Bio-Rad; 116-0302), and 5% 2-mercapto-ethanol (Bio-Rad; 161-0710), and electrophoressed on a 5–20% acrylamide monomer gradient essentially as described (Laemmli, U.K. (1970) Nature 227, 680–685). The samples were boiled for 2 minutes prior to application to a 1.5 mm wide slab gel in a Bio-Rad Model 155 Vertical Electrophoresis Cell (BioRad® 165-1420) under contant current at 30 mA per gel for 4 hours (Hoeffer power supply; PS 1200 DC) at 9° C. Constant temperature was maintained by a water bath circulator (Haake, A81). Gels were stained with 0.5% Coomassie Blue R250 (Bio-Rad #16-0400) in 5.7% acetic acid and 47% methanol overnight and destained in the same solution without stain. Specific gels demonstrating low concentrations of proteins were restained by a silver technique as described by Merril (Merril, C. R., Goldman, D., Sedman, S. and Ebert, M. H. (1981) 211:1437–1438), (Bio-Rad silver staining kit; #161-0443).

Results

Comparison of Tumor Growth Inhibitory Activities from Gel Filtration Chromatography on Bio-Gel P10 at Room Temperature and at 4° C.

The growth inhibitory activity derived from acidified, ethanol extracts of human umbilical cords eluted by gel filtration chromatography using Bio-Gel® P10 resin with apparent molecular weights ranging from 5,000–16,000 daltons. Occasionally, another peak of activity has been observed at molecular weights ranging from 3000–5000 daltons. The molecular weight calculations are based on the elution profiles of molecular weight standards (i.e., carbonic anhydrase-29,000; RNase-14,400; insulin-6,000) chromatographed on 1 liter of resin in a column of 4×100 cm. The elution profile derived from the column and from the large 14×100 cm column were superimposable. Acidified, ethanol extracts from human placenta identically chromatographed demonstrated elution profiles very similar to the umbilical cord extracts.

Fractions 1 to 3 from the umbilical cord acidified, ethanol extract are a very intense brown color; the color gradually disappears as the fractions progress. Fortunately, although (TGI) eluted in fractions 1, 2, and 3 containing the highest protein concentrations, the majority of activity extends past the observed protein peaks as is clearly demonstrated in FIGS. 16 and 17. Extracts from human placental material showed a greater overlap of TGI with the major protein peaks than was observed with material from human umbilical cords (data not shown). Aliquots of identical volumes from gel filtration chromatography electrophoresed by SDS-PAGE on a 5–20% polyacrylamide gradient also illustrated that by fraction 4, considerably less protein is found than in fractions 1 to 3. In fractions 5 an 6, major bands of 5,600 and 14,000 band are observed and by fraction 7 very little protein remains, although inhibitory activity extends into fraction 10 as shown in FIG. 17. The obvious advantage of the majority of activity eluting in regions of less protein is that it facilitates further purification of TGIs.

A comparison of Bio-Gel® P-10 chromatograms performed at room temperature and 4° C., illustrated in FIGS. 1 and 2, respectively, clearly indicate that inhibitory activity is better preserved at 4° C. At 23° C., no activity is observed past fraction 6 (FIG. 16), while at 4° C., activity is extended for 4 more fractions to fraction 10. Most importantly, the net amount of activity recovered is at least two-fold higher when extracts are chromatographed at 4° C., since 80% or more tumor growth inhibitory activity is obtained in 7 fractions at 4° C. (FIG. 16) and in only 3 fractions at 23° C. This was not due to a construction of the same quantity of activity eluting in 3 fractions (23° C.) rather then being spread over 7 fractions (4° C.), but apparently to actual increase in the yield of tumor growth inhibitory activity. One ml aliquots of fraction 5 from both columns separately and dilutions of these fractions to ⅕ to ¹⁄₁₂₅ were tested on both the human lung adenocarcinoma (A549) and mink lung cells (CCL64) (Table 7). The tumor growth inhibitory activity of the undiluted fraction was 2-fold higher in the fraction 5 obtained from chromatography at 4° C. Moreover, a 25-fold dilution of fraction 5 from chromatography at 4° C. continued to yield maximum tumor growth inhibitory activity against the human tumor cell line. A fraction of equivalent dilution from chromatography at 23° C. showed no detectable activity. A similar observation was made with the mink cell line. This information was not based on activities observed in FIGS. 16 and 17 but from two separate columns which demonstrated equivalent TGI activities in their respective fifth fraction.

Comparison of the Effects of TGIs on Normal Human Fibroblasts (HuFs) and Transformed Human Lung Carcinoma Cells (A549).

Aliquots of fractions obtained from human umbilical cord acidified, ethanol extracts chromatographed on a Bio-Gel® P-10 resin, (4° C.), were tested for tumor growth inhbitory activity on human normal and transformed cells as described in Materials and Methods. As illustrated in FIG. 18, tumor growth inhibitory activity against human A549 cells (open triangles) ranged from fractions 3 to 12, while these same fractions induced as much as an 85% increase in growth stimulation of the normal human fibroblasts. Thus, the inhibitory activity is specific for human tumor cells. This observed inhibitory activity is not due to cytotoxicity, as demonstrated by light microscopic studies and indirectly by its stimulatory effect on normal human fibroblasts. The TGI's have previously been tested on "normal" epithelial derived cells and simlar results were observed.

TABLE 7

EFFECT OF TEMPERATURE ON THE RECOVERY OF TUMOR GROWTH INHIBITORY ACTIVITY FROM GEL FILTRATION CHROMATOGRAPHY

| TEMPERATURE OF COLUMN RUN | PERCENT INHIBITION OF THE TEST CELL | |
|---|---|---|
| | 4° C. | 23° C. |
| TEST CELL LINE | | |
| A549 (Human Carcinoma) | | |
| Undiluted | 57 | 30 |
| 1/5 | 62 | 25 |
| 1/25 | 54 | 0 |
| 1/125 | 15 | 7 |
| Mink lung (CC1 64) | | |
| Undiluted | 91 | 43 |
| 1/5 | 90 | 13 |
| 1/25 | 70 | 9 |
| 1/125 | 31 | 2 |

One ml aliquots from gel filtration on fraction 5 (FIGS. 16 and 17) containing 120 micrograms were used to assay TGI activity.

High Performance Liquid Chromatography (HPLC)

TGIs from acid ethanol extracts of human umiblical cords partially purified by gel filtration on a Bio-Gel® P-10 column followed by further purification using reverse phase HPLC (uBondapak® $C_{18}$ resin) inhibited the growth of both A549 human carcinoma and an established mink lung cell line, CCL 64, but did not inhibit the growth of normal human fibroblasts. FIG. 19 illustrates an elution profile of the tumor growth inhibitory activity obtained by HPLC using a linear acetonitrile gradient of lyophilized fraction 4 (19.8 mg/3 ml 0.05% trifluroacetic acid) derived from the Bio-Gel® P-10 chromatographic step.

Evidence of two distinct peaks of growth inhibitory activities against both the A549 human carcinoma and the mink cells were observed. The fractions eluting between 28–34% (fractions 13–22) acetonitrile and 35–39% (fractions 25–31) acetonitrile were pooled separately and rechromatographed on a $C_{18}$ uBondapak® column using a linear gradient of 2-propanol.

The first peak of tumor growth inhibitory activity was designated TGI-1 and the second TGI-2. FIG. 20 demonstrates the elution profile and tumor growth inhibitory activity of TGI-1 (FIG. 19). The concentration of injected material was 1.5 mg/1.5 ml of 0.05% trifluroacetic acid (TFA). TGI-1 activity elutes between 17–23% using a linear gradient of 2-propanol. Similarly, FIG. 21 indicates that TGI-2 (0.8 mg/1.8 ml 0.05% TFA) (FIG. 20) rechromatographed between 23–27% (fraction 17–23) using a linear gradient of 2-propanol. The tumor growth inhibitory activity presented in FIGS. 19 and 20 are consistently 20% higher against the mink cells than against the A549 human carcinoma cells.

Acid ethanol extracts of human placenta contained TGI activities which, following a gel filtration chromatographic step, also eluted between 26–34% acetonitrile of a $C_{18}$ column using a linear acetonitrile gradient containing 0.05% TFA.

Ion Exchange Chromatography

One gram of a lyophilyzed acidified, ethanol extract of human umbilical cords was directly subjected to ion exchange chromatography on CM-TRISACRYL® in 0.01 M ammonium acetate, pH 4.0. A linear gradient was applied from 0.01 to 1.0 M ammonium acetate, pH 4.0. FIG. 22 demonstrates at least 4 separate tumor growth inhibitory activities designated CM-I, CM-II, CM-II, and CM-IV. CM-I was presently inhibited only the A549 human carcinoma cells at 60% inhibition (Table 8). CM peaks II and III have similar levels of growth inhibiting activity against both A549 human carcinoma (80 and 63%, respectively) and mink cells (61 and 76%, respectively). The last peak of activity (CM-IV) demonstrates a specificity in activity against mink (i.e. mink cells were more inhibited (95%) than were the A549 human carcinoma cells (69%)). CM-I was not retained and CM-II was slightly retarded by the negatively charged resin since they both were eluted before the gradient was started by 0.01 M ammonium acetate, pH 4.0.

Although all the proteins that have inhibitory activity are acidic proteins, since they are soluble at pH 4.0 and bind to a negatively charged resin, peaks CM-III and IV are probably slightly more basic since they bind more tightly to the CM-TRISACRYL® resin (eluting at greater than 0.5M ammonium acetate). This is substantiated by the fact that no TGI activity was retained by a

TABLE 8

TGI ACTIVITY FROM CATION EXCHANGE CHROMATOGRAPHY

| PEAK OF TGI | PERCENT INHIBITION OF THE TEST CELL | |
|---|---|---|
| ACTIVITY | A549 | Mink |
| CM I | 60 | 0 |
| CM II | 80 | 61 |

TABLE 8-continued

TGI ACTIVITY FROM CATION EXCHANGE CHROMATOGRAPHY

| PEAK OF TGI | PERCENT INHIBITION OF THE TEST CELL | |
|---|---|---|
| ACTIVITY | A549 | Mink |
| CM III | 63 | 76 |
| CM IV | 69 | 95 |

Protein concentrations for the fractions tested for TGI activity ranged from 15–300 μg.

positively charged resin (i.e. DEAE-TRISACRYL®) (data not shown). The more acidic inhibitory factors appear to be more specific for the A549 human carcinoma cells in their respective activities. These 4 peaks of TGI activities (CM-I, CM-II, CM-III, and CM-IV) have been repeatedly observed (6 separate chromatographic procedures with CM-TRISACRYL®). To ensure that the tumor growth inhibitory activities observed in CM-III and CM-IV would not yield material that could be eluted earlier from the column, and also to provide support for the notion that each peak of activity is a separate entity, material from CM-III and CM-IV was pooled, lyophilized, and rechromatographed using CM-TRISACRYL under the same conditions as the column from which it was derived. CM-III and CM-IV eluted (greater than 0.5 M ammonium acetate) in exactly the same position as did the original column fractions from which they were derived (FIG. 25). The higher tumor growth inhibitory inhibitory activity against mink cells was preserved and the difference between the inhibitory activity against the two cell lines remained exactly the same at 25–30% around the peak of activity.

Physical and Biological Characterization of Tissue Derived Tumor Cell Growth Inhibitory Activity (TGIs)

Fractions 2, 4 and 6 derived from gel filtration chromatography by Bio-Gel P-10 were either heat treated (Table 9). All fractions tested retained tumor growth inhibitory activity following either heat or acid treatment (see Table 10). Fractions 2, 4 and 6 were found to inhibit human cancer cell growth and stimulate normal human cell growth.

TABLE 9

EFFECT OF HEAT TREATMENT ON TGI ACTIVITY OF FRACTIONS FROM GEL FILTRATION CHROMATOGRAPHY

| | A549 | | MINK | |
|---|---|---|---|---|
| COLUMN FRACTION | CONTROL PERCENT INHI- BITION | AFTER HEAT TREATMENT PERCENT INHIBITION | CONTROL PERCENT INHI- BITION | AFTER HEAT TREAT- MENT PERCENT INHIBI- TION |
| 2 | 16 | 32 | 54 | 68 |
| 4 | 63 | 65 | 78 | 80 |
| 6 | 70 | 63 | 82 | 71 |

Protein concentrations for the fractions tested from TGI activity ranged from 15–300 ug.

TABLE 10

PHYSICAL AND BIOLOGICAL PROPERTIES OF TISSUE-DERIVED TUMOR CELL GROWTH INHIBITORY ACTIVITY (TGI)

| | Column Fraction | | |
|---|---|---|---|
| | Fraction 2 | Fraction 4 | Fraction 6 |
| Stable to 1.0 M acetic acid | + | + | + |
| Stable to boiling at 100° C. | + | + | + |
| Inhibits human cancer cells | + | + | + |
| Inhibits normal human cells | − | − | − |

Fourth Series of Experiments
Materials and Methods

Isolation of Tissue-Derived Tumor Growth Inhibitors (TGIs) From Tissue Extracts Depleted of Blood, Veins, and Arteries Veins and arteries were removed from human umbilical cord tissues and the remaining tissues were extensively washed to remove blood prior to acid/ethanol extraction as described under Third Series of Experiments.

The buffer for washing and homogenizing the tissue (PBS-PA) consisted of 2 liters of water containing 16 gm NaCl, 2.5 gm $Na_2HPO_4 \cdot H_2O$, 0.4 gm $NaH_2PO_4 \cdot 7H_2O$, 116 mg phenylmethylsulfonyl fluoride (PMSF) (Sigma P7627) and 3.3 ml Aprotinin (Sigma A6012 with 19.8 units Trypsin inhibitor per ml in 0.9% NaCl and 0.9% benzyl alcohol), adjusted to pH 7.4 with HCl and NaOH. The extraction buffer consisted of 375 ml of 95% (v/v) ethanol (punctilious, 190 proof, U.S. Industrial Chemicals, #UN1170), 7.5 ml of concentrated HCl, 33 mg of phenylmethylsulfonyl fluoride (PMSF) (Sigma P-7627) and 1 ml of Aprotinin (Sigma A6012) mixed with 192 ml of distilled water at 4° C. Eight hundred to one thousand grams of frozen human umbilical cords (Advanced Bio-technologies®; stored at −80° C.) were thawed by immersion in PBS-PA for two hours at 4° C. Individual umbilical cords were removed and rinsed with PBS-PA. Veins and arteries were removed from the umbilical cords by dissection at 4° C. The dissected umbilical cord was washed with fresh PBS-PA to remove residual blood and vascular debris.

The tissue was placed in a 4° C. chilled Cuisinart food processor (Model DLC-7-PRO) and suspended in 200 ml of 4° C. PBS-PA. The suspended tissue was homogenized by the food processor. After the first minute of homogenization, an additional 200 ml of 4° C. PBS-PA was added. The tissue suspension was homogenized for a total of 10 min. at 4° C. The homogenate was transferred to 200 ml centrifuge bottles (Sorvall) and centrifuged at 9000 rpm (RCF=13,000) for 5 minutes at 4° C. in a Sorvall RC5B centrifuge equipped with a Sorvall GSA rotor. The supernatant fluid was removed and discarded and the pellet resuspended to the original homogenate volume with fresh PBS-PA.

The pellet was washed by repeated centrifugation and resuspension as described until the supernatant fluid was clear with no tint of red from contaminating blood or blood products. The resulting washed pellet was white. The washed pellet was resuspended in the buffer for extraction to a final volume of 6 ml per gram of original dissected tissue. The homogenate was transferred to a large 4 liter beaker with a 3 inch stir bar and stirred at half of the maximum stirring capacity of a LAB-line Multimagnestir® multimixer, Model #1278. After overnight extraction with stirring at 4° C., the homogenate was transferred to 1 liter centrifuge bottles (Sorvall) and centrifuged at 3500 rpm (RCF=3570) for 30 minutes at 4° C. in a Sorvall RC-3B centrifuge equipped with a Sorvall H-6000A rotor. The supernatant was transferred to a large 4 liter beaker and adjusted to pH 5.0 with the slow addition of concentrated ammonium hydroxide. With increasing pH, the supernatant remained clear with a slight yellowish tint. A 2.0 M solution of ammonium acetate, pH 5.2, was added in an amount 1% of the total volume. Any precipitate formed by this step was removed by centrifugation at 4500 rpm (RCF=5900) for 4 hours in a Sorvall® RC-3B at 4° C. The supernatant was transferred to large 6 liter flasks to which four volumes of anhydrous ether (−20° C.) (Baker #9244-3) and two volumes of 95% ethanol (4° C.) were added. The mixture was allowed to stand undisturbed at −20° C. for 48 hours to allow the resulting precipitate to settle.

At the end of the 48 hr precipitation, the material was brought to ambient temperature in a fumehood. Warming of the acidified, ethanol extract to ambient temperature enhances the aggregation of the precipitate. The clear organic phase of ether and ethanol was removed by a water aspirator and the precipitate remained in the fume hood for several hours to allow the residual organic phase to evaporate. A gentle stream of dried nitrogen gas over the extract accelerated the evaporation of the remaining organic solvent present with the precipitate. The "dried" precipitate was dissolved in 1.0 M acetic acid and dialyzed extensively against 1.0 M acetic acid (Baker #9507-5) using dialysis membranes with a molecular weight cutoff of 3500 (Spectropor 3®, Spectrum Medical Industries, Los Angeles, Calif.). The dialyzed acidified extract was lyophilized in 250 ml Corning conical centrifuge tubes (Corning 25350) and stored as crude acidified, ethanol extract or dialyzed extensively against 20 mM $NH_4O_2C_2H_3$, pH 4.5. Comparison of tumor growth inhibitory activity in the initial acid/ethanol extract from tissue prepared as described in the Third Series of Experiments with tissue prepared as described above.

The improvement in the specific activity and total recovered activity seen when the tissue was prepared as described above is shown in Table 11. The table compares the yields of protein and tumor growth inhibitory activity from frozen umbilical cord when it was processed according to the procedures detailed in the Third Series of Experiment (hereinafter "initial procedure") and when it was processed as describe above (hereinafter "modified procedure").

There are several obvious differences in the two procedures which are of importance for the subsequent purification of TGI. For example, based on the wet weight of the tissue, acidified ethanol extraction by the initial procedure resulted in the recovery of 0.33% as protein (3.3 g from 1000 g tissue) whereas only 0.015% as protein (0.05 g from 340 g tissue) was extracted when following the modified procedure. Because the yield of activity was 50% greater ($3.3 \times 10^6$ units) by the modified procedure than in the initial procedure ($2 \times 10^6$ units) from 66% less tissue (340 g vs 1000 g) the overall efficiency of extraction was improved. The initial procedure yielded 2000 units of tumor growth inhibitory activity per gram of umbilical cord (wet weight). The modified procedure yielded 9700 units of tumor growth inhibitory activity per gram of umbilical cord (wet weight). The overall efficiency of extraction was improved 5-fold by the modified procedure. Furthermore, since less protein was extracted by acidified ethanol, the volumes of ether and ethanol required to precipitate the extracted proteins are less. Finally, the amounts of protein and the numbers of different proteins extracted by the modified procedure are fewer and therefore the subsequent purification procedures to be employed will require less chromatographic materials, shorter processing times and fewer steps to obtain a pure product.

TABLE 11

Comparison of Tumor Growth Inhibitory Activity in the Initial Acid/Ethanol Extract from Tissue Prepared as Described in the Initial Procedure with that Prepared as Described in the Modified Procedure

| Tissue[1] (wet weight) | Procedure | Protein (extracted) | Total[2] Activity | Specific[2] Activity |
|---|---|---|---|---|
| 1000 g | initial | 3.0 g | $2 \times 10^6$ u | 0.67 u/ug protein |
| 340 g | modified | 50 mg | $3 \times 10^6$ u | 67 u/ug protein |

[1]Human umbilical cord
[2]A unit of activity is defined as that amount of material which results in 50% of the maximal inhibition seen with a given cell line, e.g., the A549 (as used for this table) cell line is maximally inhibited 60%, therefore a unit of activity is equivalent to 30% inhibition.

Fractionation of TGI extracted using the modified procedure on the cation exchange resin CM-TRISACRYL was resolved as a single peak from the bulk of the applied protein when the bound material was eluted by a linear salt gradient from 0–1.0 M NaCl. FIG. 24 shows that following application of TGI to a CM-TRISACRYL column no inhibitory activity was detectable from material not bound to the resin (i.e., fractions 1–24). The linear addition of increasing amounts of NaCl (- - -) removed the majority of protein bound to the resin (fractions 25–38) prior to the removal of significant amounts of inhibitory activity (∇- - -∇) fractions 39–49). The NaCl concentration most effective in removing bound TGI was approximately 0.6 M (fraction 44). Comparison of FIG. 24 with FIG. 23 suggests that the inhibitory activity eluted in the experiment of FIG. 24 most closely corresponds to the elution of CM-III and CM-IV from the CM-TRISACRYL resin as depicted in FIG. 22 since the salt concentrations (NaCl, FIG. 24; $NH_4O_2$—$C_2H_3$, FIG. 23) for elution are similar (0.6 M, FIG. 26; 0.6–0.7 M, FIG. 23). The above information also suggests that treatment of the tissue by the modified procedure allows the preferential isolation of a single peak of TGI, thus improving subsequent characterization of the factor.

Another property of the TGI extracted from the tissue by the modified procedure is its failure to bind to anion exchange resin. FIG. 25 shows that following adjustment of the pH to 8.0 as described in the figure legend and application of the extract (an identical amount to that used in FIG. 24) to the anion exchange resin DEAE-TRISACRYL® resulted in the majority of inhibitory activity associating with nonbinding material (fractions 1–30), whereas the bulk of the applied protein (as determined by absorbance at 280 nm, (_____) bound to the column resin. These results show that under the conditions of FIG. 10, contaminating proteins can be removed from TFI and, therefore, that it is a useful procedure for purification of TGI. In addition, these results show that at pH 8.0, TGI is a cation since it does not bind the anion exchange resin. Finally, the results of FIG. 25 show that TGI as extracted by the modified procedure is similar in ionic character to those polypeptides (TGI-1, TGI-2, CM-I, CM-II, CM-III and CM-IV) extracted by ion exchange resin in the initial procedure since none of these bound to the anion exchange resin.

Large amounts of sample can be reproducibly fractionated by CM-TRISACRYL, thus furnishing more TGI for subsequent purification procedures. In FIG. 26, 9.9 mg of tissue extract were applied to a CM-TRISACRYL® column (15 ml) under the same chromatographic conditions as shown in FIG. 25 for a smaller sample size (2.65 mg protein) on a smaller CM-TRISACRYL® column (5 ml). Resolution of tumor growth inhibitory activity from the majority of proteinaceous material by a linear gradient of NaCl was essentially the same in both experiments.

FIG. 27 shows fractionation of pooled samples (FIG. 28, fractions 59–78) from a CM-TRISACRYL column by HPLC on a uBondapac® C18 column. Following application of the sample, no significant inhibitory activity was observed by linearly increasing acetonitrile concentrations from 0–25%. However, tumor growth inhibitory activity against both A549 (human lung carcinoma) and CCL64 (mink lung, 0—0) eluted in a single peak between 28–34% acetonitrile (fractions 21–31) while the majority of material absorbing at 206 nm was eluted at lower (fractions 11–19) and at higher (fractions 37–50) acetonitrile concentrations.

An apparent molecular weight of TGI (termed TGI-1 and CM-III and CM-IV in the initial procedure) was determined by gel filtration chromatography (Sephadex G-50, data not shown) using suitable protein standards of known molecular weights. Thus, in the absence of certain interfering proteins (e.g., hemoglobin) the apparent molecular weight of TGI has been determined to be between 20 kDa and 30 kDa under nondenaturing conditions.

The modified procedure detailed herein describes a powerful and simple procedure for removing inert or interfering compounds from the TGI extracts prepared as described in the initial procedure. Furthermore, the modified procedure improves the efficacy of the various chromatographic steps employed in the isolation of TGI by reducing the amount of chromatographic materials required thus reducing the preparation time of TGI. In addition, and as shown, extraction of TGI from the umbilical cord as described herein allows TGI and other proteins to chromatograph more reproducibly than in the procedure previously described. TGI isolated according to the modified procedure has been characterized with respect to the chromatographic features on both reverse phase high performance liquid chromatography and CM-TRISACRYL ion exchange chromatography. TGI has been found to behave similarly to or identically with TGI-1 (compare FIGS. 20 and 27) by RPHPLC, and thus has similar or identical hydrophobic properties and is shown also to behave similarly to or identically with CM-III and CM-IV (compare FIGS. 24 and 26) on a cation exchange resin, thus having similar or identical ionic properties. It is therefore concluded that TGI as isolated in the modified procedure and TGI-I and CM-III and CM-IV are similar or identical compounds having similar or identical ionic and hydrophobic properties and thus are of similar or identical composition. Therefore, the modified procedure described herein provides a more efficacious method of obtaining a purer form of TGI for further analysis and characterization.

Fifth Series of Experiments
Materials and Methods

Acidified Ethanol Extraction and Ether/Ethanol Precipitation

The buffers and equipment used were exactly as described in the second series of experiments, for each relevant step in the procedure. Two hundred to four hundred grams (200–400 gr.) of human umbilical cord, either dissected free of vasculature or left intact and chopped into ½ inch pieces were washed free of the majority of blood in PBS-PA at 4° C. The cord was drained by gravity through a sieve and transferred to a chilled food processor at 4° C. for homogenization in a maximum volume of 200 ml of PBS-PA. The tissue was homogenized for fifteen minutes and washed free of blood by repeated centrifugation in 200 ml plastic bottles at 5,000 RPM using an RC-5B centrifuge (Sorvall) equipped with a GSA rotor (Sorvall) for ten minutes with PBS-PA, until the optical density at 28 nm was less than 0.05 and the pellet obtained, was essentially white in color. The pellet was transferred to a 2 liter glass beaker and suspended in extraction buffer, as described in the third series of experiments, at a final volume of 3 ml per gram of the original wet weight of tissue and stirred for twenty-four hours at 4° C. The suspension was centrifuged in a 1.0 liter plastic centrifuge bottle using a RC-3B centrifuge (Sorvall) equipped with a H6000A rotor (Sorvall) for 30 minutes at 3,500 rpm. The resulting supernatant was transferred to a 2 liter beaker and the pH adjusted first to 5.0 with concentrated ammonium hydroxide, and then to 5.2 by the addition of 2 M ammonium acetate to a final concentration of 1% of the total volume. The solution retained a clear or very slightly yellow tinted appearance.

Following ether/ethanol precipitation, as described previously, the supernatant was siphoned from the flask to within ¾ of an inch above the bottom of the flask containing the flocculent precipitate. The precipitate and remaining ether/ethanol solution was centrifuged in a GSA rotor at 5,000 RPM for 20 minutes in 250 ml plastic conical bottles (Corning #25350) in a Sorvall RC-5B centrifuge. This step in the procedure was designed to decrease the loss of TGI's from the ether/ethanol supernatants immediately above the precipitate. The resulting pellet was suspended in 1.0 M acetic acid and the flask containing the ether/ethanol precipitate was also washed with 1.0 M acetic acid to remove any TGI protein remaining on the wall of the flask. The optical density at 280 nm was between 0.5 and 1.0 and the final volume did not exceed 100 ml for each preparation. The TGI containing protein solution was dialyzed for one day against 1.0 M acetic acid and for one to two days against two changes of 4.0 M ammonium acetate, pH 4.5 using dialysis membranes with a molecular weight cutoff of 3,500 (Spectropor 3).

It should be noted that tumor growth inhibitory activity can also be obtained from acidified ethanol extraction of the tissue with omission of the ether-ethanol precipitation step. However, the specific activity of these preparations is 50% less and the total yield of activity 10–30% less than "standard" preparation utilizing the ether-ethanol precipitation.

Hydrophobic Interaction Chromatography

The dialyzed protein was subjected to hydrophobic interaction chromatography using phenyl-Sepharose® (Pharmacia) as the chromatographic resin. The phenyl-Sepharose® was equilibrated with 4.0 M ammonium acetate, pH 4.5. Following dialysis (at least 24 to 48 hours), the conductivity and pH of the protein solution was measured and dialysis terminated when the conductivity of the dialysate and equilibration buffer were the same. The protein was pumped onto (Microperplex® pump #2132-LKB) the resin contained in a 1.6×2.0 cm chromatography column (K-20-Pharmacia) using 1 ml of resin per 2.0 mg of protein, at 1.0 ml per minute. The column was washed until the $OD_{280}$ was zero and tumor growth inhibitory activity eluted from the column using a decreasing gradient from 4.0 M to 0.04 M ammonium acetate, pH 4.5 containing an increasing concentration of ethylene glycol (Mallinkrodt) from 0 to 50%. The total volume of the eluting gradient was 10 times the total volume of the resin used for each individual preparation. The bound protein was eluted over approximately fifty fractions. Ten microliters of sample were transferred to a plastic tube (polystyrene) containing 50 micrograms of BSA, for assay of inhibitory activity against both the mink CCL64 and A549 cell lines, as described in the first series of experiments.

As seen in FIG. 28, the tumor growth inhibitory activity began eluting from the column at 1.5 M ammonium acetate 31% ethylene glycol and was completely eluted from the column by 40 mM ammonium acetate and 50% ethylene glycol. The biologically active fractions were pooed, dialyzed against 1.0 M acetic acid, and lyophilized in a polypropylene 50 ml tube (Scientific Products #C2390-50) or siliconized glass lyophilization flask (Virtis).

Reverse Phase High Pressure Liquid Chromatography

The lyophilized biologically active material was diluted in 1.0 to 3.0 ml of 0.05% trifluoracetic acid (TFA) containing 10% acetonitrile, placed in a 16×100 mm siliconized disposable glass tube, sonicated for two minutes, centrifuged at 3,000 rpm for 10 minutes (Beckman Model TJ-6) to remove insoluble material, and subjected to reverse phase, high pressure liquid chromatography (RPHPLC) using a Microbondapak® C18 resin (Waters Assoc. 0.39×30 cm, PN 27324). No more than 1 mg of TGI was applied to each column such that the number of column procedures necessary for each preparation depended on the total protein concentration of the active fraction obtained following chromatography by phenyl-Sepharose. This amount was approximated at $OD_{280}$ using a value of 1.0 optical density units equal to 1.0 mg/ml of protein. The protein was eluted from the column, at 1.0 ml per minute in a stepwise, gradient fashion using 100% acetonitrile containing 0.05% TFA as the eluting mobile phase. The gradient was increased to 25% acetonitrile ($CH_3CN$) in 15 minutes, eluted for 10 minutes at 25% ($CH_3CN$), increased to 27% in two minutes, 17% for 10 minutes, increased to 28% in two minutes, 28% for 10 minutes, increased to 30% over 10 minutes, resulting to 44% in 10 minutes, and to 100% in 10 minutes. The absorbance of protein was monitored at 210 nm and 0.005 ml aliquots were removed from every other 1.0 ml fraction to assay for tumor growth inhibitory activity against both CCL 64 and A549 cell lines. Tumor growth inhibitory activity eluted initially at 27% acetonitrile and continued to elute at 28–30% acetonitrile as shown in FIGS. 29A & 29B. At every step in the purification, the biologically active fractions were pooled and subsequently assayed for total tumor growth inhibitory activity by removing an aliquot and multiplying the activity obtained in the assay by the appropriate dilution factor. The quantity of tumor growth inhibitory activity present in the pool was compared to an aliquot of starting material. Thus, column recoveries of activity and protein (where measurable) could be obtained.

Figure 30A:
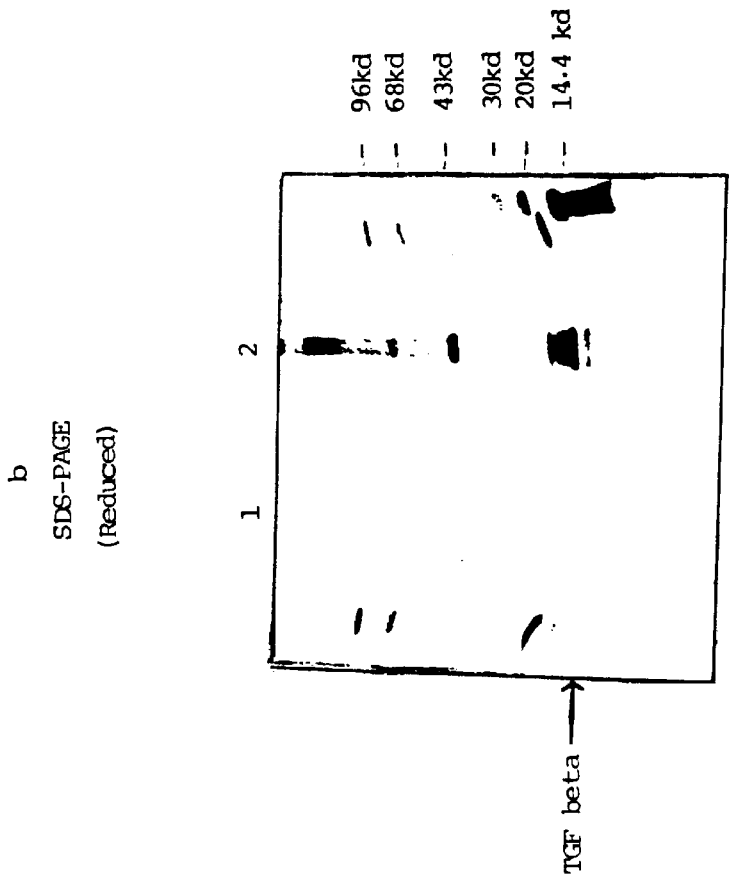
Figure 30B:
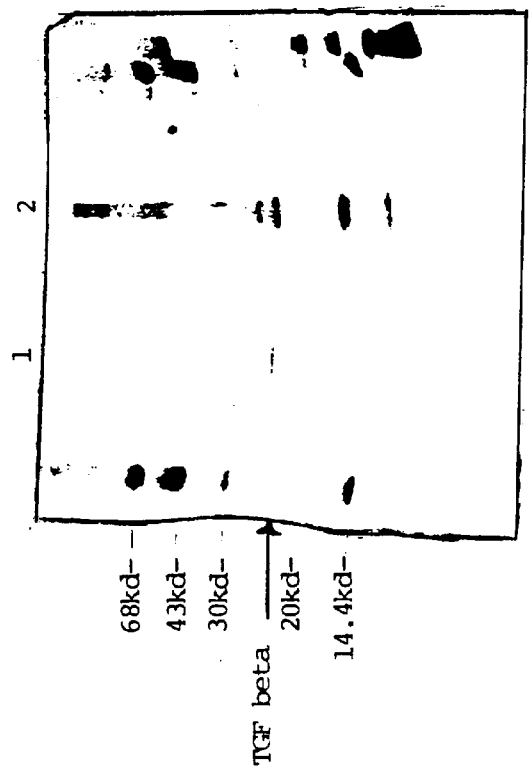

The area designated with arrows (fractions 47–51) in FIG. 29A derived from two separate C18 chromatographic procedures (derived from one phenyl-Sepharose column, from one isolation) was pooled and subjected to SDS-PAGE• both under non-reducing conditions (FIG. 30A) and in the presence of 0.5% B-Mercaptoethanol (reducing conditions) (FIG. 30B). This area of the chromatogram (FIG. 29A) demonstrated the highest biological activity and lowest amount of contaminating proteins (highest specific activity and lowest absorbance at 210 nm). Experimental details of SDS-PAGE are reported in FIGS. 30A & B In lane 2, under non-reducing conditions (FIG. 30A), the biologically active fractions are shown to contain at least 4 major protein bands. Lane 1 contains a purified preparation of TGF- derived from platelets (provided by Bruce Magun, Oregon State Health Science University, Portland, Oreg.). The biological activity that has been ascribed to this protein is the ability to confer anchorage independent growth to normal rat kidney cells (NRK) in a soft agar assay, only in the presence of a growth factor, such as EGF at 2.0–2.5 ng/ml. Thus, its growth promoting activity is directly dependent on other bioactive proteins (Roberts et al., Cold Spring Harbor Conf. Cell Proliferation, 9: 319–332 (1982)); Anzano et al., Anal. Biochem. 125: 217–224 (1982); Cancer Research 42: 4776–4778 (1982).

In our assay for tumor growth inhibitory activity, TGF- was shown to posses 1–30 units of inhibitory activity per ng of protein. By comparison it appears that one of the protein bands in the TGI preparation FIG. 30A (lane 2) also migrated in the same position of approximately $M_r$=25 kDa at the TGF-β, (lane 1). The same samples electrophoresed in the presence of 5% B-Mercapto-ethanol, showed that the protein band that had migrated at $M_r$ 26 kDa disappeared and a new band was evident at approximately 12.5 kDa FIG. 30B (lane 2). TGF-β FIG. 30B (lane 1 also changed its migratory position to 13 kDa following reduction. All other proteins in the TGI containing sample remained in the same position of migration and thus were insensitive to reduction. The units of inhibitory activity applied to the gel for each sample was approximately 1,000–1,500 (50 ng) for TGF-β in lane 1 and 10,000 to 20,000 for TFI in lane 2 (FIGS. 30A & B).

Further purification of the TGI biologically active fractions derived from the RPHPLC C18 chromatographic procedure was accomplished by RPHPLC using a CN Microbondapak• column (0.39×30 cm Waters PN 84042) (FIG. 31). The biologically active fractions were lyophilized in 16×100 mm siliconized glass tubes, dissolved in 1.0–3.0 ml 0.05% TFA containing 10% propanol and applied to the column. Column elution was achieved at 1.0 ml/minute by using a linear gradient of 2-propanol from 10 to 20% in ten minutes, followed by 20 to 50% in fifteen minutes (0.6%/min.), and finally from 50–100% in 20 minutes.

Iodination of Biologically Active Fractions for Analysis by SDS-PAGE

Active, lyophilized fractions 56, 58, 59–65, 66–68, illustrated in FIG. #18, and approximately 4 ng of TGF-β were iodinated by the chloramine T method (McConahey, P. J. and Dixon, F. J. (1966) Int. Arch. of Allergy 29, 185–189). Each fraction was resuspended in 100 microliters of 0.1M acetic acid, and 3 microliters of 1.5M Tris, pH 8.8 was added to adjust the pH to 7.0. Ten microcuries of carrier-free sodium iodide $I^{125}$ Na was added, followed by 2 microliters of chloramine T (Sigman #C9887) at 1.0 mg/ml. The tube was rocked for one minute and the reaction terminated by the addition of 2 microliters of sodium metabisulfite (Sigma #S9000) at 1.0 mg/ml. After two minutes 0.05 ml of each sample was transferred to a siliconized glass tube (10×75 mm) containing 0.05 ml of twice concentrated sample buffer plus 5% β-mercaptoethanol for SDS-PAGE slab gel electrophoresis.

The remainder of the sample was diluted in 0.05 ml of twice concentrated sample buffer and approximately 200,000 TCA precipitable radioactive counts were applied to individual lanes for SDS-PAGE, FIG. 32). The gel was stained with 0.125% Coomassie Blue for 10 minutes to fix the protein in the gel, and exhaustively destained to remove free radioactive iodine. When the destain solution did not contain detectable label as judged by counting 1.0 ml of destain solution in a gamma counter (Beckman, Riagamma #1294), the gel was dried using a gel dryer (Hoeffer-SE1150) and exposed to x-ray film (Kodak-XAR) for autoradiography (one week).

All lanes to which biologically active TGI was added contained a faint band of protein migrating at $M_r$ 24 kDa. This protein band also migrated directly in a horizontal plane with the $M_r$ 26 kDa band in lane 7 containing 256 inhibitory units of TGF-β derived from platelets (FIG. 32, lane 7 arrow).

In lanes 1, 2, 3 and 5 containing approximately 180, 2,000, 46 and 408 units of tumor growth inhibitory activity respectively, the $M_r$ 25 kDa band was observed while lanes 4 and 6, which did not possess tumor growth inhibitory activity, did not contain this protein band. Lane 2, which contained the most active fractions (from FIG. 16), showed two faint bands at $M_r$ 26 kDa and 30 kDa. Lane 3 appears to have only one band of $M_r$ 26 kDa.

Following the last step of purification of TGI, protein concentration could not be measured because it was below the detection level using standard means of measurement. Therefore, the bands migrating at $M_r$ 26 kDa (from lanes 2, 3 and 7) were excised from the dried gel and counted in a gamma counter in order to extrapolate the protein concentrations applied in lanes 2 and 3. Since it was known that 0.4 ng of TGF-β was applied to the gel which had 5,593 cpm at $M_r$ 26 kDa, then 362 (lane 2) and 195 (land 3) cpm at the position of 26 kDa equals 26 pg and 14 pg, respectively. These calculations assume that the number of tyrosines and extent of iodination of each tyorsine were the same.

Although the presence of the $M_r$ 26 kDa band was consistent with the presence of tumor growth inhibitory activity (FIG. 32), the quantity (units) of activity, especially in lane 2, did not correlate with the amount of TGF- protein, as judged by the intensity of iodinated protein applied to the gel (0.4 ng). Thus, TGI demonstrated at least one log more inhibitory activity than TGF-β.

Since a broad peak of activity was obtained by RPHPLC C18• chromatography, FIG. 29A; and in FIG. 29B it appeared that there may be two peaks of activity, one at 27% and at 28–30%, the area designated by these separate peaks were pooled and chromatographed separately by RPHPLC using a CN column. The slope of the propanol gradient was changed so that the increase in increments of 2-propanol was 0.375% per minute, instead of 0.6% per minute. The shallow gradient was devised to achieve a better separation of active proteins eluting between 40–45% 2-propanol.

FIG. #33 illustrates the elution profile of the CN column of active fractions pooled at 27% acetonitrile (Pool I) from the previous C18 column. The most active fraction (fraction #14) eluted at 40–41% 2-propanol. A lower amount of activity was seen eluting after this peak, as a double peak at approximately 44% 2-propanol. Similarly, rechromatography of the active material derived from the peak of activity pooled at 28–30% acetonitrile (Pool II) from the C18 column, demonstrated peak of activity corresponding to the elution from the CN column at 44% 2-propanol (FIG. 34). The first pool (Pool I) of activity eluting at 27% acetonitrile contained some active material from Pool II eluting at 28–30% acetonitrile, thus a small quantity of this peak of activity was revealed in the chromatogram of Pool I at 40–41% 2-propanol (FIG. 33). Most significantly the further purification of TGI has permitted resolutio of two major peaks of TGI activity, eluting at 40–41% for Pool I and 44% for Pool II.

Pool I from the C18 column contained 82% more total inhibitory activity than Pool II.

FIG. #35 is a tracing of the peaks of activity from the two separate chromatographs FIGS. 35 (Pool I), and 36 (Pool II). This FIG. (35) illustrates two distinct peaks of inhibitory activity as the different active fractions from the C18 column Pool I and Pool II.

It was found that preservation of TGI biological activity following chromatography through the C18 column was better achieved if the active fractions were not lyophilized prior to CN chromatography. Therefore, the samples were concentrated by partial lyophilization (not to completion) and stored at −20° C.

II. Tumor Growth Inhibitory Activity from the Conditioned Media of Various Tumor Cell Lines Effect of Dithiothreitol on TGI Activity from Tumor Cell Conditioned Media Human tumor A431 (epidermoid carcinoma), A673 (rhabdomyosarcoma) and T24 (bladder carcinoma) cells were grown to cofluence on T150 (150 cm$^2$) flasks in 20 ml of complete growth medium containing DMEM supplemented with 10% fetal bovine serum. The confluent monolayers were rinsed twice with Dulbecco's• phosphate buffered saline and incubated in 10–12 ml serum-free DMEM per flask for 24 h. Conditioned media (100–115 ml) was collected from 1–4×10$^8$ cells.

An erythroleukemia cell line, K562, was grown in suspension to a cell density of 10$^6$ cells per ml and one liter of serum-free conditioned media was collected. Cellular debris was removed from the conditioned media (RC-5B GSA rotor-Sorvall) by centrifugation at 800 rpm for 60 min. at 4° C. The supernatant was treated with 1 ml of 1M acetic acid per 100 ml of conditioned media, extensively dialyzed in Spectropor 3 dialysis tubing (Spectrum Medical Laboratories) against multiple changes of 1M acetic acid, and lyophilized. The lyophilized, acid-treated conditioned media was resuspended in 4 mm HCl at a volume of 5.0 ml for A431, A673 and T24, and 1.5 ml for K562 derived media. Insoluble material was removed by centrifugation in a Rc-5B centrifuge (Sorvall, SA 600 rotor) at 3400 rpm for 15 min. at 4° C. and the supernatants transferred to 1.5 ml microfuge tubes. Following centrifugation in an Eppendorf microfuge for 15 min. at 4° C., the supernatants were transferred to 1.5 ml microfuge tubes for storage at −20° C. Protein concentration was determined by absorbance at 280 nm. The tumor growth inhibitory activity of individual samples was tested for sensitivity to reduction by Dithiothreitol (DTT). An aliquot each of 0.5 ml was transferred to two tubes containing 4.5 ml of 0.1M NH$_4$HCO$_3$. One tube recived a final concentration of 65 mm DTT, and both tubes were incubated for 2 hours at room temperature. The incubated mixture was then transferred to Spectropor 6 dialysis tubing and dialyzed against 1M acetic acid for 2 days to removed DTT. The dialyzed samples were then assayed for tumor growth inhibitory activity as described in initial procedures. The effect of DTT on TGI activity derived from conditioned media from the A431, A673, K562 and T24 cell lines using mink cells, CLL 64, and A549 cells as target cells is summarized in Tables 12 and 13, respectively. The table shows the tumor growth inhibitory activity from conditioned media from A673, K562, and T24 against both mink and A549 cells was lost following reduction (Table 12), whereas the tumor growth inhibitory activity from the conditioned media of A431 cells, which showed preferential inhibitory activity against A549 cell, was only slightly reduced following reduction (First column, Table 13).

removal of blood and vasculature from umbilical cord yielded approximately a 100-fold increase in specific activ-

TABLE 12

EFFECT OF DITHIOTHREITOL (DTT) ON TUMOR GROWTH INHIBITORY ACTIVITY FROM TUMOR CELL CONDITIONED MEDIA USING MINK TARGET CELLS[1]

| | PERCENT INHIBITION (%) | | | | | | | |
|---|---|---|---|---|---|---|---|---|
| Protein | A431 | | A673 | | K562 | | T24 | |
| ug | -DTT | +DTT | -DTT | +DTT | -DTT | -DTT | +DTT | -DTT |
| 61.8 | 95 | 28 | 95 | 21 | 88 | 13 | 94 | 12 |
| 12.4 | 93 | 19 | 95 | 0 | 91 | 14 | 93 | 21 |
| 2.5 | 70 | 11 | 94 | 0 | 92 | 18 | 92 | 15 |
| 0.5 | 26 | 11 | 87 | 14 | 86 | 0 | 92 | 7 |
| 0.1 | 29 | 6 | 50 | 0 | 49 | 12 | 75 | 1 |

1 Conditioned media from A431, A673, K562 and T24 cells was treated with 65 mM Dithiothreitol (DTT) and tested for tumor growth inhibitory activity against target cells compared to control.

TABLE 13

EFFECT OF DITHIOTHREITOL ON TUMOR GROWTH INHIBITORY ACTIVITY FROM TUMOR CELL CONDITIONED MEDIA USING A549 TARGET CELLS

| | PERCENT INHIBITION (%) | | | | | | | |
|---|---|---|---|---|---|---|---|---|
| Protein | A431 | | A673 | | K562 | | T24 | |
| ug | -DTT | +DTT | -DTT | +DTT | -DTT | +DTT | -DTT | +DTT |
| 61.8 | 75 | 45 | 71 | 8 | 74 | 12 | 79 | 28 |
| 12.4 | 69 | 56 | 70 | 2 | 71 | 2 | 77 | 11 |
| 2.5 | 49 | 42 | 58 | 4 | 61 | 0 | 76 | 20 |
| 0.5 | 28 | 35 | 34 | 0 | 36 | 9 | 60 | 2 |
| 0.1 | 10 | 10 | 7 | 1 | 14 | 0 | 47 | 5 |

1 Conditioned media from A431, A673, K562 and T24 cells was treated with 65 mM Dithiothreitol (DTT) and tested for tumor growth inhibitory activity against A549 compared to control.

Reverse Phase HPLC of A431 Conditioned Media

Lyophilized conditioned media from $4 \times 10^8$ A431 cells (110 ml) was processed as previously described, except 5.0 ml of 4 mM HCl was used to solubilize the lyophilized material. The insoluble precipitate was removed by centrifugation as described and protein concentration determined. An aliquot of 0.2 ml (680 ug protein) was added to 1.8 ml of 0.1M ammonium bicarbonate or this same buffer containing 65 mm DTT. Following incubation for 2 hours at room temperature, both the reduced and non-reduced samples were lyophilized and resuspended in 2.0 ml of 0.05% trifluoracetic (FA) for RPHPLC. Following injection onto a C18 semi-preparative column, the proteins were eluted at 1.0 ml per minute using a linear gradient of acetontrile from 0–50% in 50 minutes. An aliquot of 1.0 ml was removed from each 2.0 ml fraction to assay for growth inhibitory activity against both mink and A549 cell lines as described in the initial procedures. FIG. 36 illustrates that there are two peaks of inhibitory activity, one that elutes at 25% acetonitrile, which inhibits both CCL64 and A549 cells, and one that elutes at 30–36% acetonitrile, which shows preferential inhibitory activity toward the A549 cell line. Following DTT treatment (FIG. 37), the first peak of activity (25% acetonitrile) is no longer present, while the activity that is selective for A549 cells retained activity.

Conclusions from the "Fifth Series of Experiments"

I. It was already demonstrated by the FOURTH Series of Experiments referred to as the "modification procedure" that ity of the TGI over Third Series of Experiments (Table 11). In the Fifth Series of Experiments, referred to as "alternate procedure", it was shown that only removal of blood, but not the vasculature was necessary to obtain TGI with the same average degree of specific activity as indicated by the Fourth Series of Experiments. In fact, the vascular tissue from umbilical cord, dissected free form the stromal tissue, demonstrated tumor growth inhibitory activity of similar to the umbilical stromal tissue alone (data not shown). It was further shown that tumor growth inhibitory activity could be recovered without ether/ethanol precipitation of the extracted material.

The volume of acidified ethanol per gram of tissue used for extraction was 50% less than described for both the initial procedure and modified procedure. Thus, the total volume of extracted protein was less, therefore requiring ½ the amount of ether and ethanol used for precipitation. This minimized amount of protein that would remain on the flask walls. Moreover, the amount of 1.0M acetic acid necessary to dissolve the precipitate and wash the flask was smaller so that final volumes were kept to a minimum. The obvious advantage is the minimization of protein/activity loss, thereby creating a more efficient method of extraction, including less reagents required. Also, chopping whole cord rather than dissecting cord shortened the tedious preparation time considerably. The average specific activity of the final preparation derived from 200–400 grams of umbilical cord (wet weight) prior to further purification by chromatographic techniques was approximately $1–3.0 \times 10^6$ units/ 40–50 mg (see Table 14).

TABLE 14

SUMMARY OF PURIFICATION OF TGI FROM UMBILICAL CORD

| Step | Protein (mg) | Units | Units/mg | Fold | % Recovery Units |
|---|---|---|---|---|---|
| 1. ether/ethanol* precipitate | 20–50 | $1–3 \times 10^6$ | $5 \times 10^4$ | 1 | 100 |
| 2. phenol Sepharose | 1–3 | $1–5 \times 10^6$ | $1–2 \times 10^6$ | 20–40 | 100 |
| 3. RPHPLC-C18 | 0.02 | $0.2–2.3 \times 10^6$ | $1–2 \times 10^{9}$*** | $2–4 \times 10^4$ | 60–100 |
| 4. RPHPLC-CN | N.D.** | $0.05–1.5 \times 10^6$ | $0.1–1 \times 10^{10}$*** | $2–4 \times 10^6$ | 1–10 |

*from 200–400 gr. wet tissue
**N.D., not detectable
***estimated because protein concentrations were undetectable These results are within the range of the experimental results reported for the "modified procedure" and therefore, represent the same range of improvement in protein recoveries and specific activities compared to the initial procedure (Table 11). Thus, the overall efficiency of extraction was improved approximately 5-fold as reported in the "modified procedure".

Table 8 summarizes the current procedure utilized to obtain active TGI from human umbilical cord. Between 60 to 100% recover of units of activity was observed through the firs two steps of purification (HIC and RPHPLC on C18). This represents a 40,000 increase in specific activity of $1. \times 10^6$ units/microgram. ($2.3 \times 10^6$ total units from 300 g wet umbilical cord). It was observed that contaminating proteins probably aided in the stabilization of biological activity of TGI, because as the purification ensued, activity became more labile. The greatest loss of recovery occurred following lyophilization of the active fraction obtained after RPHPLC on the C18 column. This greatly reduced the total number of units applied to the CN column in the final step of purification. This loss was ameliorated by concentrating the active fractions by lyophilization, but not to completion. The recovery of units from this final step of purification was between 60–100%.

Previously in the "initial procedure", chromatograms varied foremost of the preparations, thus, causing difficulty in devising subsequent steps for improvement. The current methodology described in both the modified and alternate procedure demonstrate reproducibility of all chromatograms, yields of proteins, and yields of activity at each step, utilizing material derived from individual umbilical cord preparations. This improvement is a direct result of the removal of hemoglobin (denatured), before acidified, ethanol extraction, and the more efficient removal of other contaminating proteins during the first chromatographic step using phenyl-Sepharose.

The use of hydrophobic interaction chromatography (HIC) using phenyl-Sepharose as the first chromatographic step in the purification procedure proved to be a major improvement in overall yield of activity (total units) and specific activity (units/mg). Following ion exchange chromatography by CM-Trisacryl, a specific activity of 4. $2 \times 10^4$ units per mg was obtained, while phenyl-Sepharose chromatography produced TGI with a specific activity of $1.07 \times 10^6$ u/mg. At this step, phenyl-Sepharose chromatography introduced approximately a 20-fold purification into the procedure. However, the TGI containing protein obtained by phenyl-Sepharose chromatography demonstrated 26 times greater specific activity than TGI containing material derived from CM-Trisacryl chromatography.

Experiments have been devised to improve the overall yield (inhibitory units) and specific activity of the TGI-containing protein so that there would be adequate biologically active material present to subject the protein to as many steps necessary for purification to homogeneity. Both the removal of blood in the "modification procedure" and the use of phenyl-Sepharose chromatography in the "alternate procedure" have aided greatly in accomplishment of this goal. The introduction of phenyl-Sepharose chromatography into the purification procedure has provided material with higher specific activity ($1–2 \times 10^6$ units/microgram) which permitted further purification of a minimal amount of starting material (wet tissue weight) and requiring less steps toward the final purification to homogeneity. One peak of TGI activity, eluting at 1.5M ammonium acetate, 37% ethylene glycol, was obtained following phenyl-Sepharose chromatography (FIG. 28). This was also a major improvement in the isolation of TGI in the "modification procedure" using CM Trisacryl, compared to the initial procedure (FIG. 22).

Another improvement introduced into the purification of TGI's by the "alternate procedure" was the use of a stepwise elution by acetontrile from C18 RPHHPLC (FIGS. 29A & 20B) rather than a linear gradient used in the "initial and modification procedures" (FIG. 27). Elution of the column in this fashion allows approximately 90% of the biologically inactive contaminants to be separated from the major peak of activity. Of most significance is that two hundred to fur hundred grams of wet cord material provides sufficiently less protein following chromatography on phenyl-Sepharose, to apply the entire preparation to a maximum of three and a minimum of two RPHPLC C18 and analytical columns using no more than 1.0 mg for each (FIGS. 29A & 29B).

The ability to obtain larger quantities of a more highly purified biologically active protein following RPHPLC on a C18 resin is directly related to the isolation of tumor growth inhibitory activity of high specific activity from phenyl-Sepharose chromatography. Following chromatography by CM-Trisacryl (modification procedure), only 20% of the total biologically active fraction could be subjected to one RPHPLC (C18), while generally 50% of the total biologically active, pooled fraction from phenyl Sepharose chromatography could be applied at one time to a C18 column. In these individual comparative experiments, the starting material for chromatography using CM Trisacryl was 9.9 mg and for phenyl-Sepharose was 42 mg, thus if the same amount of starting material was used for CM-Trisacryl, only 4.7% of the total preparation could have been utilized in the following C18 step. Because a greater amount of inhibitory activity could be applied to the C18 column 100 times less sample (0.005 ml compared to 0.5 ml), was used to achieve the same degree of inhibitory activity. At this point in the procedure, the most biologically active fractions were resolved into six major protein bands by SDS-PAGE using silver stain.

Following HPLC on the C18 column, protein concentration could not be determined because the amount of available protein was below the resolution of standard techniques ($OD_{280}$ or Lowry). Thus, it was assumed that protein concentration was less than 20 micrograms/ml. To further purify TGI, the active fractions were pooled, lyophilized and applied to a RPHPLC CN column. Using a 2-propanol gradient of 0.6% increase in solvent per minute, the activity was shown to be displaced to the right of most of the protein (FIG. 31). Various active fractions were iodinated and separated by SDS-PAGE. The fractions demonstrating the most biological activity (FIG. 31, Fractions 59–65) illustrated in lane 2, contained two isotopically labeled bands, one of 25 kDa and one of 30 kDa and in lane 3 fractions 66–68 contained a homogeneous band at 25 kDa. Fraction #58 lane 7 is active but contains at least 5 bands. Fractions #56 which is the major peak of protein and is not biologically active contained all of the protein bands in fraction #58 except that 26 kDa band (FIG. 32, lane 1).

Three major conclusions can be deduced from the gel presented in FIG. 32 One, a 26 kDa protein is always present in fractions containing biologically active material and similarly it is always absent in fractions that are not biologically active. Two, the TGI demonstrates a similar qualitative activity to an ubiquitous protein derived from platelets and other tissues designated as TGF-β, in that it migrates by SDS-PAGE as a protein of $M_r$ 26 kDa as shown in FIGS. 30B and FIG. 32. Three, the active fractions demonstrating the most biological activity in FIG. 32, lane 2, (2,068 units), does not compare intensity (iodinated protein) to the appearance of the 26 kDa band for TGF-β, observed in lane 7 containing 256 units of inhibitory activity. This implies a quantitative difference in specific activity.

The use of a stepwise gradient elution from the C18 column with acetonitrile resolved two peaks of activity, one eluting at 27% and one at 28–30% (FIGS. 29A & 29B). Following the combination of individual fractions into two separate pools, Pool I (27%) and Pool II (28–30%), from a column demonstrating a similar profile as shown in FIGS. 29A & 29B, the pools were applied to a RPHPLC CN column using a more shallow gradient than shown in FIG. 31 (0.37%/min. compared to 0.6%/min.). Pool I eluted at 40–41% 2-propanol (FIG. 33) and Pool II at 44% 2-propanol (FIG. 33). It is important to note that, as expected, the more hydrophobic protein eluting from the C18 column (Pool II) continued to elute more hydrophobically from the CN column. Thus, two distinct peaks of growth inhibitory activity have been obtained using the "alternate procedure" of protein purification. The first peak of activity, Pool I, contains 82% more inhibitory units than Pool II.

A purified protein, derived from platelets, designated as TGF-β, is biologically active in our inhibitory assay but consistently possesses 10–100 fold less activity than Pool I. Since activity in all cases, Pool I, Pool II, and TGF-B is consistent with presence of a protein band of $M_r$ 26 kDa (FIGS. 30 and 32), one can assume that all these proteins may be similar or belong to a family of growth inhibitory and/orowth modulating proteins. Alternatively, because of the differential elution of these proteins on both C18 and CN resins, and the greater specific activity of TGI's, TGI's may be entirely different than TGF-β (elevation of TGF-β profile not shown). Further biochemical characterization (amino acid sequencing) should resolve this question. In conclusion, it appears that TGI's are better than (inhibitor activity) and different from (eluting position) TGF-β derived from platelets used for comparison by this study.

The conditioned media from A431 contained two types of growth inhibitory activity. One TGI elutes at approximately 25% acetonitrile and inhibits both A549 and CCl 64 mink cells. The selectivity of inhibition of this TGI is similar to what is observed for TGI-1 and TGI-2 in human umbilical cord extracts. The second TGI eluting between 30–36% acetonitrile shows a greater specificity for inhibiting A549 cells over mink cells. The TGI eluting between 30–36% acetonitrile resembles the TGI in that both selectively inhibit A549 cells in this test system.

Applicants presently contemplate a family of discrete entities which share certain common characteristics. Each family member is a polypeptide dimer, bound by disulfide bonds, with a molecular weight of 26,000 daltons which demonstrates tumor growth inhibitory activity against both a mink lung cell line (CCL 64) and a human carcinoma cell line (A549) in monolayer cultures.

The family comprises the novel discrete factors TGI-1 and TGI-2 and the previously disclosed factors TIF-1 and TGF-β. It is presently contemplated that TIF-1 and TGF-β are the same polypeptide which may be distinct from both TGI-1 and TGI-2. TGI-1 and TGI-2 being discrete cannot both be the same as TGF-. TGI-1 and TGI-2 each have a specific activity greater than TGF-β. Both TGI-1 and TGI-2 elute differently from TGF-β on high pressure liquid chromatography on a CN column with 2-propanol. Further, TGFI-1 and TGFI-2 elute differently from each otehr on high pressure liquid chromatography on a CN column with 2-propanol.

Two separate factors CM-1 and a polypeptide derived from conditioned media of human tumor cell line (A549) are also disclosed. Because both have the property of substantially inhibiting the growth of a human tumor cell line (A549) but not of an established mink lung cell line (CCL 64) it is contemplated that CM-1 may be the same as the TGI derived from conditioned media from A431 cells. It is also contemplated that CM-1 may be similar to TIF-2 of an earlier patent.

What is claimed is:

1. A homogeneous polypeptide composition having a molecular weight of 25(26) kDa as determined by SDS-PAGE and having the property of inhibiting growth of a mink lung cell line, CCL64 (ATCC Accession Number PTA-3450) wherein said composition is prepared by a process comprising:
   (a) obtaining an acidified ethanol extract of human umbilical cord;
   (b) hydrophobic interaction chromatography of said extract;
   (c) reverse phase high pressure liquid chromatography on a $C_{18}$ column using an acetonitrile gradient;
   (d) rechromatography by reverse phase high pressure liquid chromatography on a CN column using a 2-propanol gradient;
   (e) recovery of fractions from step (d) having the property of inhibiting growth of a mink lung cell line, CCL64 (ATCC Accession Number PTA-3450); and
   (f) subjecting the fractions so recovered to SDS-PAGE.

* * * * *